United States Patent [19]
Fukuda

[11] Patent Number: 5,856,138
[45] Date of Patent: Jan. 5, 1999

[54] HUMAN PARATHYROID HORMONE MUTEINS AND PRODUCTION THEREOF

[75] Inventor: Tsunehiko Fukuda, Kyoto, Japan

[73] Assignee: Takeda Chemical Industries, Ltd., Osaka, Japan

[21] Appl. No.: 733,446

[22] Filed: Oct. 18, 1996

Related U.S. Application Data

[63] Continuation of Ser. No. 402,970, Mar. 10, 1995, abandoned, which is a continuation of Ser. No. 926,787, Aug. 5, 1992, abandoned.

[30] Foreign Application Priority Data

Aug. 7, 1991 [JP] Japan ................................ 3-198056
Jun. 26, 1992 [JP] Japan ................................ 4-169713

[51] Int. Cl.$^6$ .......................... C12N 15/16; C07K 14/635
[52] U.S. Cl. ................ 435/694; 435/320.1; 435/252.3; 435/325; 530/324; 536/23.51; 536/24.1
[58] Field of Search ........................ 530/324; 435/69.4, 435/320.1, 252.3, 325; 536/23.51, 24.1

[56] References Cited

U.S. PATENT DOCUMENTS

| | | | |
|---|---|---|---|
| 4,423,037 | 12/1983 | Rosenblatt et al. | 424/177.1 |
| 4,656,250 | 4/1987 | Morita et al. | 530/324 |
| 5,166,322 | 11/1992 | Shaw et al. | 530/351 |
| 5,393,869 | 2/1995 | Nakagawa et al. | 530/324 |

FOREIGN PATENT DOCUMENTS

| | | |
|---|---|---|
| 0139076 | 5/1985 | European Pat. Off. . |
| 0 341 963 | 11/1989 | European Pat. Off. . |
| 0 451 867 | 10/1991 | European Pat. Off. . |
| 0 483 509 A1 | 5/1992 | European Pat. Off. . |
| WO 88/03165 | 5/1988 | WIPO . |
| WO 90/14415 | 11/1990 | WIPO . |

OTHER PUBLICATIONS

Murray et al. Endocrinology 124(2), 1097–1099, abstract only, 1989.
Yen et al. (1983), Can. J. Physiol. Pharmacol. vol. 61, pp. 1324–1328.
Chorev et al. (1990) Biochemistry 29(6), 1580–6.
Rabbani et al. (1988) Endocrinology 123(6), 2709–16.
Wingender et al. (1989) GBF Monogr., 12(Adv. Protein Des.), 167–76.
J. Biol. Chem., Rabbani et al.; 263 1307 (1988).
Biochemistry, Rabbani et al.; 29, 10080 (1990).

*Primary Examiner*—Stephen Walsh
*Assistant Examiner*—Karen E. Brown
*Attorney, Agent, or Firm*—David G. Conlin; Cara Z. Lowen

[57] ABSTRACT

Disclosed are (1) a human parathyroid hormone mutein which comprises at least one modification selected from the group consisting of (i) deletion of 3 to 6 amino acid residues on the N-terminal side in the amino acid sequence of human parathyroid hormones, (ii) substitution of another lipophilic amino acid residue for at least one methionine residue in the amino acid sequence, and (iii) substitution of a cysteine residue for one amino acid residue within the region of amino acid residue Nos. 34 to 47 in the amino acid sequence; (2) a recombinant DNA having a nucleotide sequence coding for the human parathyroid hormone mutein described in (1); (3) a vector containing the recombinant DNA described in (2); (4) a vector in which the recombinant DNA described in (2) is inserted into a region controlled by an *E. coli* T7 promoter; (5) a transformant which is transformed by the recombinant DNA described in (2); and a process for producing a human parathyroid hormone mutein which comprises cultivating the transformant described in (5) in a culture medium.

7 Claims, 28 Drawing Sheets

Fig. 1

CGT.GTA.GAA.TGG.CTC.CGT.AAG.AAG.TTG.CAG.GAT.GTG.CAC.AAT.TTT.GTT.GCC.TTA.GGT.GCC
Arg-Val-Glu-Trp-Leu-Arg-Lys-Lys-Leu-Gln-Asp-Val-His-Asn-Phe-Val-Ala-Leu-Gly-Ala

R { ATG.CAT.AAC.CTT.GGC.AAA.CAT.TTG.AAC.TCC.ATG.GAG
    (-Met-His-Asn-Leu-Gly-Lys-His-Leu-Asn-Ser-MET-Glu

CCA.TTG.GCT.CCT.CGT.GAT.GCT.GCT.CCT.TCC.CAA.AGA.CCA.CGT.AAA.AAG.GAA.GAC.AAT.GTC.TTA
Pro-Leu-Ala-Pro-Arg-Asp-Ala-Gly-Ser-Gln-Arg-Pro-Arg-Lys-Lys-Glu-Asp-Asn-Val-Leu

GTT.GAG.AGC.CAT.GAA.AAA.TCC.CTA.GGC.GAG.GCA.GAC.AAG.GCC.CAT.GTC.AAT.GTA.TTA.ACT
Val-Glu-Ser-His-Glu-Lys-Ser-Leu-Gly-Glu-Ala-Asp-Lys-Ala-Asp-Val-Asn-Val-Leu-Thr

AAA.GCT.AAA.TCC.CAG
Lys-Ala-Lys-Ser-Gln

R = { TTA    { CAG TTA    { ATT CAG TTA    { GAG ATT CAG TTA    { TCT GTG TCC GAG ATT CAG TTA
      Leu      Gln Leu      Ile Gln Leu      Glu Ile Gln Leu      Ser Val Ser Glu Ile Gln Leu

Fig. 2

```
         10         20         30         40         50         60
                    ⎧TTAATGCA  ⎧TAACCTTGC  AAACATTTCA  ACTCCATGGA
                   Z⎨
                    ⎩AATTACGT  ⎩ATTGGAACCG  TTTGTAAACT  TGAGGTACCT
Nde I              Hinf I                                 Nco I
         70         80         90        100        110        120
GCCTGTAGAA  TGGCTCGTA  AGAAGTTGCA  GGATGTGCAC  AATTTTCTTG  CCTTAGGTGC
CGGACATCTT  ACCGAGCCAT  TCTTCAAGCT  CCTACACGTG  TTAAAACAAC  GGAATCCACG
                                    HgiA I                  Dde I
        130        140        150        160        170        180
CCCATTGGCT  CCTCGTGATC  CTGGTTCCCA  AAGACCACGT  AAAAAGGAAG  ACAATGTCTT
GGGTAACCGA  GGAGCACTAC  GACCAAGGGT  TTCTGGTGCA  TTTTCCTTC  TGTTACAGAA
Bg ℓ I                              HgiA I                   Dde I
        190        200        210        220        230        240
AGTTGAGAGC  CATGAAAAAT  CCCTAGGCGA  GGCAGACAAG  GCCGATCTGA  ATGTATTAAC
TCAACTCTCG  GTACTTTTTA  GGGATCCGCT  CCGTCTGTTC  CGGCTACACT  TACATAATTG
   Alu I               Avr II                     Hae III            Dde I
        250        260        270
TAAAGCTAAA  TCCCAGTAAT  GAG
ATTTCGATTT  AGGGTCATTA  CTCCTAG
  Alu I                BamH I Z : ⎧TATG     ⎧TATCCAG    ⎧TATGATTCAG   ⎧TATCCAGATTCAG    ⎧TATGTCTGTG TCCCAGATTC AG⎫
    ⎨         ⎨           ⎨              ⎨                ⎨                        ⎬
    ⎩AC       ⎩ACGTC      ⎩ACTAAGTC      ⎩ACCTCTAAGTC     ⎩ACAGACAC AGGCTCTAAG TC⎭
```

Fig. 3

```
#1     5'XTTAATGCA3'
#2     3'YTTACGTATTGGA5'

#3     5'TAACCTTGGCAAACATTTGAACTCCATGGAGCCGTGTAGAATGGCT3'
#4     3'ACCGTTTGTAAACTTGAGGTACCTCGCACATCTTACCGACGCATT5'

#5     5'GCGTAAGAAGTTGCAGGATGTGCACAATTT3'
#6     3'CTTCAACGTCCTACACGTGTTAAAACAACG5'

#7     5'TGTTGCCTTAGGTGCCCCATTGGCTCCTCCTGATGCTGGTTCCCAA3'
#8     3'GAATCCACGGGGTAACCGAGGAGGACTACGACCAAGGGTTTCTGGT5'

#9     5'AGACCACGTAAAAAGGAAGACAATGTCTTAGTTGAGAGCCA3'
#10    3'GCCATTTTTCCTTCTGTTACAGAATCAACTCTCGGTACTTTT5'

#11    5'TGAAAAATCCCTAGGCGAGGCAGACAAGCCGATGTGAATGT3'
#12    3'TAGGGATCCGCTCCGTCGTGTTCCGGCTACACTTACATAATTG5'

#13    5'ATTAACTAAAGCTAAATCCCAGTAATGAG3'
#14    3'ATTTCGATTTAGGGTCATTACTCCTAG5'

#1-a   X=5'TATG3'        #1-b   X=5'TATGCAG3'      #1-c   X=5'TATGATTCAG3'
#2-a   Y=  3'AC5'        #2-b   Y=3'    ACGTC5'    #2-c   Y=3'    ACTAAGTC5'

#1-d   X=5'TATGGAGATTCAG3'        #1-e   X=5'TATGTCTGTGTCCGAGATTCAG3'
#2-d   Y=3'    ACCTCTAAGTC5'      #2-e   Y=3'    ACAGACACAGGCTCTAAGTC5'
```

Fig. 6

ATT.CAG.TTA.ATG.CAT.AAC.CTT.GGC.AAA.CAT.TTG.AAC.TCC.ATG.GAG
Ile-Gln-Leu-Met-His-Asn-Leu-Gly-Lys-His-Leu-Asn-Ser-MET-Glu

CGT.GTA.GAA.TGG.CTG.CGT.AAG.AAG.TTG.CAG.GAT.GTG.CAC.AAT.TTT.GTT.GCC.TTA.GGT.GCC
Arg-Val-Glu-Trp-Leu-Arg-Lys-Lys-Leu-Gln-Asp-Val-His-Asn-Phe-Val-Ala-Leu-Gly-Ala

CCA.TTG.GCT.CCT.CGT.GAT.GCT.GGT.TCC.CAA.AGA.CCA.CGT.AAA.AAG.GAA.GAC.AAT.GTC.TTA
Pro-Leu-Ala-Pro-Arg-Asp-Ala-Gly-Ser-Gln-Arg-Pro-Arg-Lys-Lys-Glu-Asp-Asn-Val-Leu

GTT.GAG.AGC.CAT.GAA.AAA.TCC.CTA.GGC.GAG.GCA.GAC.AAG.GCC.GAT.GTG.AAT.GTA.TTA.ACT
Val-Glu-Ser-His-Glu-Lys-Ser-Leu-Gly-Glu-Ala-Asp-Lys-Ala-Asp-Val-Asn-Val-Leu-Thr

AAA.GCT.AAA.TCC.CAG
Lys-Ala-Lys-Ser-Gln

Fig. 9

TCT.GTG.TCC.GAG.ATT.CAG.TTA.ATG.CAT.AAC.CTT.GGC.AAA.CAT.TTG.AAC.TCC.ATG.GAG
Ser-Val-Ser-Glu-Ile-Gln-Leu-Met-His-Asn-Leu-Gly-Lys-His-Leu-Asn-Ser-Met-Glu

CGT.GTA.GAA.TGG.CTG.CGT.AAG.AAG.TTG.CAG.GAT.GTG.CAC.AAT.TTT.TGC.CCC.TTA.GGT.GCC
Arg-Val-Glu-Trp-Leu-Arg-Lys-Lys-Leu-Gln-Asp-Val-His-Asn-Phe-Cys-Pro-Leu-Gly-Ala

CCA.TTG.GCT.CCT.CGT.GAT.CCT.CCT.TCC.CAA.AGA.CCA.CCT.AAA.AAG.GAA.GAC.AAT.GTC.TTA
Pro-Leu-Ala-Pro-Arg-Asp-Ala-Gly-Ser-Gln-Arg-Pro-Arg-Lys-Lys-Glu-Asp-Asn-Val-Leu

GTT.GAG.AGC.CAT.GAA.AAA.TCC.CTA.GGC.GAG.CCA.GAC.AAG.GCC.GAT.CTG.AAT.GTA.TTA.ACT
Val-Glu-Ser-His-Glu-Lys-Ser-Leu-Gly-Glu-Ala-Asp-Lys-Ala-Asp-Val-Asn-Val-Leu-Thr

AAA.GCT.AAA.TCC.CAG
Lys-Ala-Lys-Ser-Gln

Fig. 12

TCT.GTG.TCC.GAG.ATT.CAG.TTA.ATG.CAT.AAC.CTT.GGC.AAA.CAT.TTG.AAC.TCG.CTG.GAG
Ser-Val-Ser-Glu-Ile-Gln-Leu-Met-His-Asn-Leu-Gly-Lys-His-Leu-Asn-Ser-Leu-Glu

CGT.GTA.GAA.TGG.CTG.CGT.AAG.AAG.TTG.CAG.GAT.GTG.CAC.AAT.TTT.GTT.CCC.TTA.GGT.GCC
Arg-Val-Glu-Trp-Leu-Arg-Lys-Lys-Leu-Gln-Asp-Val-His-Asn-Phe-Val-Pro-Leu-Gly-Ala

CCA.TTG.GCT.CCT.CGT.GAT.CCT.GGT.TCC.CAA.AGA.CCA.CGT.AAA.AAG.GAA.GAC.AAT.GTC.TTA
Pro-Leu-Ala-Pro-Arg-Asp-Ala-Gly-Ser-Gln-Arg-Pro-Arg-Lys-Lys-Glu-Asp-Asn-Val-Leu

GTT.GAG.AGC.CAT.GAA.AAA.TCC.CTA.GCC.GAG.GCA.GAC.AAG.GCC.GAT.GTG.AAT.GTA.TTA.ACT
Val-Glu-Ser-His-Glu-Lys-Ser-Leu-Gly-Glu-Ala-Asp-Lys-Ala-Asp-Val-Asn-Val-Leu-Thr

AAA.GCT.AAA.TCC.CAG
Lys-Ala-Lys-Ser-Gln

Fig. 21

TCT.GTG.TCC.GAG.ATT.CAG.CTG.CTG.CAT.AAC.CTT.GGC.AAA.CAT.TTG.AAC.TCC.ATG.GAG
Ser-Val-Ser-Glu-Ile-Gln-Leu-Leu-His-Asn-Leu-Gly-Lys-His-Leu-Asn-Ser-MET-Glu

CGT.GTA.GAA.TGG.CTG.CGT.AAG.AAG.TTG.CAG.GAT.GTG.CAC.AAT.TTT.TGC.GCC.TTA.GGT.GCC
Arg-Val-Glu-Trp-Leu-Arg-Lys-Lys-Leu-Gln-Asp-Val-His-Asn-Phe-Cys-Ala-Leu-Gly-Ala

CCA.TTG.GCT.CCT.CCT.GAT.GCT.GGT.TCC.CAA.AGA.CCA.CGT.AAA.AAG.GAA.GAC.AAT.GTC.TTA
Pro-Leu-Ala-Pro-Arg-Asp-Ala-Gly-Ser-Gln-Arg-Pro-Arg-Lys-Lys-Glu-Asp-Asn-Val-Leu

GTT.GAG.AGC.CAT.GAA.AAA.TCC.CTA.GGC.GAG.GCA.GAC.AAG.GCC.GAT.GTG.AAT.GTA.TTA.ACT
Val-Glu-Ser-His-Glu-Lys-Ser-Leu-Gly-Glu-Ala-Asp-Lys-Ala-Asp-Val-Asn-Val-Leu-Thr

AAA.GCT.AAA.TCC.CAG
Lys-Ala-Lys-Ser-Gln

Fig. 25

TTA.CTC.CAT.AAC.CTT.GGC.AAA.CAT.TTG.AAC.TCC.ATG.GAG
Leu-Leu-His-Asn-Leu-Gly-Lys-His-Leu-Asn-Ser-MET-Glu

CGT.GTA.GAA.TGG.CTG.CGT.AAG.AAG.TTG.CAG.GAT.GTG.CAC.AAT.TTT.TGC.GCC.TTA.GGT.GCC
Arg-Val-Glu-Trp-Leu-Arg-Lys-Lys-Leu-Gln-Asp-Val-His-Asn-Phe-Cys-Ala-Leu-Gly-Ala

CCA.TTG.GCT.CCT.CGT.GAT.GCT.GGT.TCC.CAA.AGA.CCA.CGT.AAA.AAG.GAA.GAC.AAT.GTC.TTA
Pro-Leu-Ala-Pro-Arg-Asp-Ala-Gly-Ser-Gln-Arg-Pro-Arg-Lys-Lys-Glu-Asp-Asn-Val-Leu

GTT.GAG.AGC.CAT.GAA.AAA.TCC.CTA.GGC.GAG.GCA.GAC.AAG.GCC.GAT.GTG.AAT.GTA.TTA.ACT
Val-Glu-Ser-His-Glu-Lys-Ser-Leu-Gly-Glu-Ala-Asp-Lys-Ala-Asp-Val-Asn-Val-Leu-Thr

AAA.GCT.AAA.TCC.CAG
Lys-Ala-Lys-Ser-Gln

Fig. 28

TCT.GTG.TCC.GAG.ATT.CAG.CTG.CTG.CAT.AAC.CTT.GGC.AAA.CAT.TTG.AAC.TGG.CTG.GAG
Ser-Val-Ser-Glu-Ile-Gln-Leu-Leu-His-Asn-Leu-Gly-Lys-His-Leu-Asn-Ser-Leu-Glu

CGT.GTA.GAA.TGG.CTG.CGT.AAG.AAG.TTG.CAG.GAT.GTG.CAC.AAT.TTT.TGC.GCC.TTA.GGT.GCC
Arg-Val-Glu-Trp-Leu-Arg-Lys-Lys-Leu-Gln-Asp-Val-His-Asn-Phe-Cys-Ala-Leu-Gly-Ala

CCA.TTG.GCT.CCT.CGT.GAT.GCT.GGT.TCC.CAA.AGA.CCA.CGT.AAA.AAG.GAA.GAC.AAT.GTC.TTA
Pro-Leu-Ala-Pro-Arg-Asp-Ala-Gly-Ser-Gln-Arg-Pro-Arg-Lys-Lys-Glu-Asp-Asn-Val-Leu

GTT.GAG.AGC.CAT.GAA.AAA.TCC.CTA.GGC.GAG.GCA.GAC.AAG.GCC.GAT.GTG.AAT.GTA.TTA.ACT
Val-Glu-Ser-His-Glu-Lys-Ser-Leu-Gly-Glu-Ala-Asp-Lys-Ala-Asp-Val-Asn-Val-Leu-Thr

AAA.GCT.AAA.TCC.CAG
Lys-Ala-Lys-Ser-Gln

Retention time (minutes)

Retention time (minutes)

HUMAN PARATHYROID HORMONE MUTEINS AND PRODUCTION THEREOF

This application is a continuation of application Ser. No. 08/402,970, filed on Mar. 10, 1995, now abandoned, which is a continuation of application Ser No. 07/926,787, filed on Aug. 5, 1992 now abandoned.

BACKGROUND OF THE INVENTION

The present invention relates to novel human parathyroid hormone derivatives useful as hormone remedies and the production thereof.

Parathyroid hormone (hereinafter also briefly referred to as PTH) is a polypeptide hormone consisting of 84 amino acids which is secreted from the parathyroid, and one of the most important regulators for calcium metabolism. Accordingly, the application of human PTH to various bone diseases such as hypoparathyroidism and osteoporosis and further the application of human PTH antagonists to hypercalcemia and the like have been strongly desired.

The DNA sequence of human PTH was first revealed by G. N. Hendy et al. [*Proc. Natl. Acad. Sci. U.S.A.*, 78, 7365–7369 (1981)]. Since then, many attempts have been made to obtain human PTH by genetic engineering techniques. Recently, it has been expressed in amounts satisfiable from the industrial viewpoint with much effort [for example, Wing L. Sung et al., *J. Biol. Chem.*, 266, 2831–2835 (1991) and European Patent Unexamined Publication No. 483509].

Human PTH has the following amino acid sequence:

Ser—Val—Ser—Glu—Ile—Gln—Leu—Met—His—Asn—Leu—
1                         5                              10
Gly—Lys—His—Leu—Asn—Ser—Met—Glu—Arg—Val—Glu—
              15                                      20
Trp—Leu—Arg—Lys—Lys—Leu—Gln—Asp—Val—His—Asn—
         25                              30
Phe—Val—Ala—Leu—Gly—Ala—Pro—Leu—Ala—Pro—Arg—
         35                              40
Asp—Ala—Gly—Ser—Gln—Arg—Pro—Arg—Lys—Lys—Glu—
    45                                        55
Asp—Asn—Val—Leu—Val—Glu—Ser—His—Glu—Lys—Ser—
              60                                    65
Leu—Gly—Glu—Ala—Asp—Lys—Ala—Asp—Val—Asn—Val—
              70                                    75
Leu—Thr—Lys—Ala—Lys—Ser—Gln (SEQ ID NO: 5).
    80

Its biological activity has previously been known to be reproducible by the fragment consisting of amino acid residues situated in the 1- to 34-positions on the N-terminal side (the positions of amino acid residues are hereinafter represented by the numbers corresponding to those of the sequence of human PTH (1–84) taking Ser as the 1-position) [G. W. Tregear et al., *Endocrinology*, 93, 1349–1353 (1973)], and many derivatives thereof have been synthesized. As to this (1–34) fragment, a peptide in which 2 to 6 amino acid residues on the N-terminal side are deleted is known to have PTH antagonist activity. Furthermore, the binding activity of a C-terminal portion, from the 35-position on, to a receptor [L. G. Rao et al., *Endocrinology*, 117, 1632–1636 (1985)] and the activating action thereof to alkaline phosphatase [T. M. Murray et al., *Endocrinology*, 124 1097–1099 (1989)] have recently been disclosed.

However, when natural type PTH (1–84) is actually used as a drug, it has some problems to be solved. For example, Met residues in a peptide chain are gradually oxidized even under ordinary conditions, and PTH whose Met residue is oxidized is significantly reduced in biological activity [A. L. Frelinger III and J. E. Zull, *J. Biol. Chem.*, 259, 5507–5513 (1984)]. Furthermore, it is generally preferred to use drugs as non-injection drugs from the simplicity and easiness of their administration. The modification of human PTH (1–84) is considered to make it possible to change the physicochemical properties of the drugs, for example, to allow the drugs to be easily absorbed from the mucous membrane.

It is the most common method to replace an amino acid(s) in a peptide chain by another amino acid(s) to attempt to improve the biological and physicochemical properties of a biologically active peptide, in order to solve such problems. Previously, the present inventors provided a high expression system of human PTH (1–84) in *Escherichia coli* (European Unexamined Patent Publication No. 483509), and succeeded in obtaining anti-oxidative derivatives by substituting other amino acid for Met residues of human PTH, utilizing this expression system. In addition, the present inventors obtained derivatives in which various amino acid residues in the center portion of the peptide chain are substituted by Cys residues. For example, a highly lipophilic group is specifically introduced into this SH group, or a dimer is formed through an S-S bond, whereby the derivative can be derived to an agonist having high affinity to a receptor or difficulty to undergo decomposition in vivo. Cyano-group can be introduced into the side-chain of the Cys residue followed by cleavage of the peptide bond to give an active fragment of PTH. Further, compounds in which several amino acid residues on the N-terminal side of PTH (1–34) are deleted are known to function as inhibitors [N. Horiuchi et al., *Science*, 220, 1053–1055 (1983)].

SUMMARY OF THE INVENTION

The present invention provides antagonists in which several amino acid residues on the N-terminal side of human PTH containing the C-terminal peptide chain are deleted, and peptides obtained by further subjecting the antagonists to the amino acid substitution mentioned above. These compounds have more desirable properties in clinical application.

In accordance with the present invention, there are provide (1) a human parathyroid hormone mutein comprising at least one modification which is selected from the group consisting of (i) deletion of 3 to 6 amino acid residues on the N-terminal side in the amino acid sequence of human parathyroid hormones, (ii) substitution of another lipophilic amino acid residue for at least one methionine residue in said amino acid sequence, and (iii) substitution of a cysteine residue for one amino acid residue within the region of amino acid residue Nos. 34 to 47 in said amino acid sequence; (2) a recombinant DNA having a nucleotide sequence coding for the human parathyroid hormone mutein described in (1); (3) a vector containing the recombinant DNA described in (2); (4) a vector in which the recombinant DNA described in (2) is inserted into the region controlled by an *E. coli* T7 promoter; (5) a transformant which is transformed by the recombinant DNA described in (2); and (6) a process for producing a human parathyroid hormone mutein which comprises cultivating the transformant described in (5) in a culture medium.

BRIEF DESCRIPTION OF THE DRAWINGS

FIG. 1 shows DNA sequences (SEQ ID NOS:24–31) and amino acid sequences (SEQ ID NOS:1–5) of the present invention corresponding to human PTH and human PTH analogues lacking its N-terminal portion;

FIG. 2 shows examples of cleavage of DNA fragments (SEQ ID NOS:24–33) in synthesizing genes coding for human PTH of the present invention and analogues lacking its N-terminal portion;

FIG. 3 shows examples of DNA fragments (SEQ ID NOS:42–55) for producing a synthetic gene corresponding to a human PTH analogue of the present invention;

FIG. 6 (SEQ ID NO:21) shows a DNA sequence and an amino acid sequence corresponding to human PTH (5–84) of Example 1;

FIG. 9 (SEQ ID NO:56) shows a DNA sequence and an amino acid sequence (SEQ ID NO:5) corresponding to [cys$^{35}$] human PTH obtained in Example 2;

FIG. 12 (SEQ ID NO:57) shows a DNA sequence and an amino acid sequence corresponding to [Leu$^{18}$] human PTH in Example 3;

Lane 1: Molecular weight marker

Figure 14:
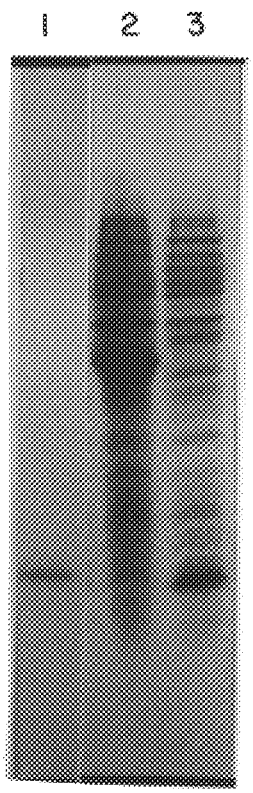

Lane 2: E. coli strain culture solution (10 μl) carrying plasmid pE-PTH (5–84) after induction of IPTG Lane 3: E. coli strain culture solution (10 μl) carrying plasmid pE-PTH (5–84) without induction of IPTG Lane 4: Human PTH expression strain culture solution (10 μl) after induction of IPTG Lane 5: Human PTH expression strain culture solution without induction of IPTG;

FIG. 14 shows results of SDS-PAGE after expression of a desired protein obtained in Example 2, together with results of control experiments:

Lane 1: Human PTH (1 μg)

Figure 15:
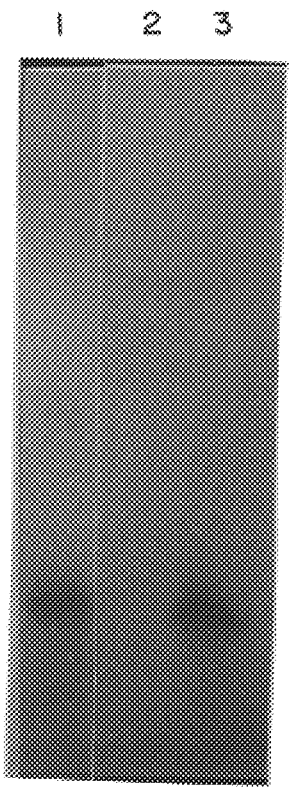
Figure 17:
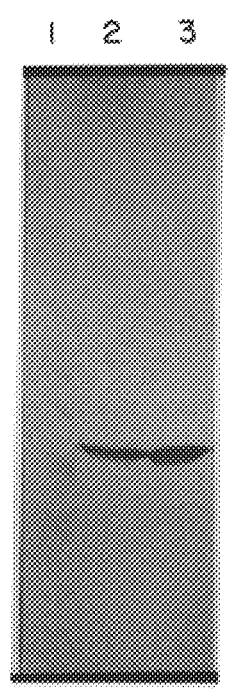
Figure 16:
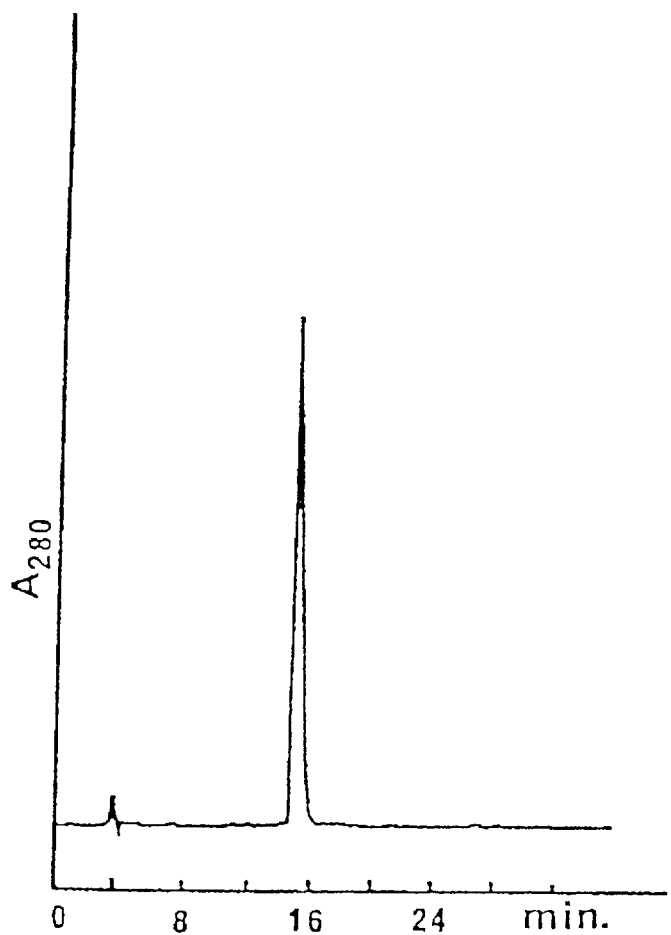

Lane 2: E. coli strain culture solution (10 μl) not carrying plasmid pE-C35PTH after addition of IPTG Lane 3: E. coli strain culture solution (10 μl) carrying plasmid pE-C35PTH after addition of IPTG;

FIG. 15 shows a western blotting of a desired protein obtained in Example 2;

FIG. 16 shows an HPLC chromatogram of purified [Cys$^{35}$] human PTH obtained in Example 2, column: YMC ODS A-303 4.6×250 mm, elution conditions: a linear gradient of 0 minute (30% acetonitrile containing 0.1% TFA) →30 minutes (38% acetonitrile containing 0.1% TFA), flow rate: 1 ml/minute;

FIG. 17 shows results of SDS-PAGE (18% polyacrylamide) of purified [Cys$^{35}$] human PTH obtained in Example 2:

Lane 1: Molecular weight marker

Lane 2: Human PTH

Figure 18:
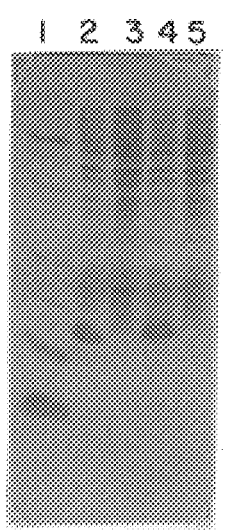

Lane 3: [Cys$^{35}$] human PTH;

FIG. 18 shows results of SDS-PAGE of expression [Leu 8] human PTH obtained in Example 3:

Lane 1: Molecular weight marker

Figure 23:
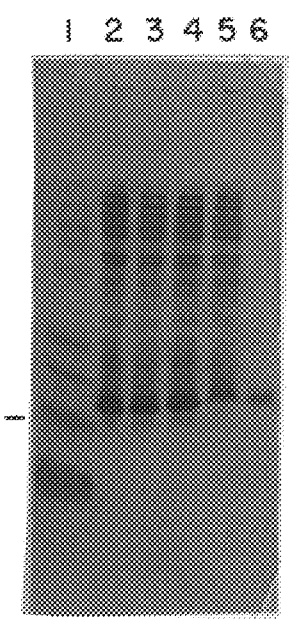
Figure 19:
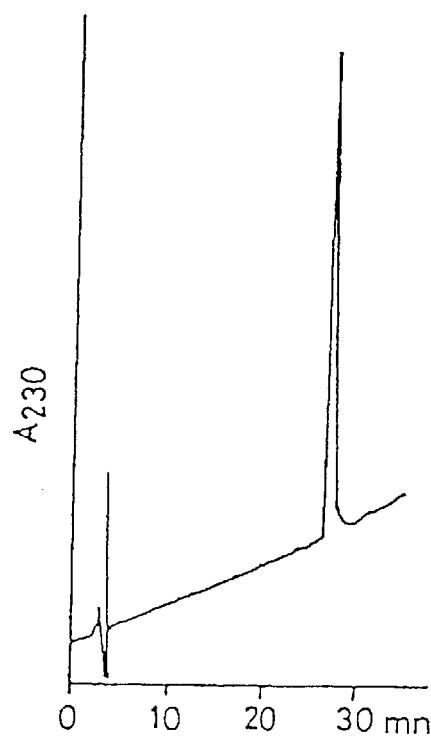
Figure 20:
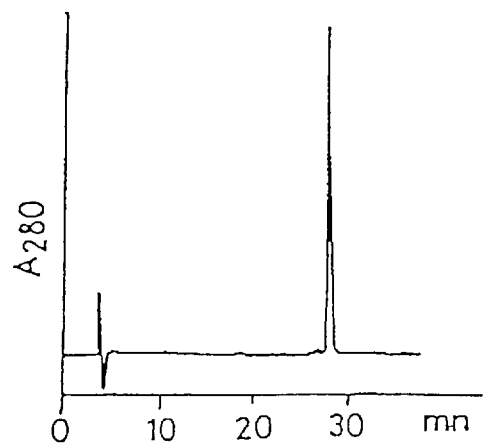
Figure 22:
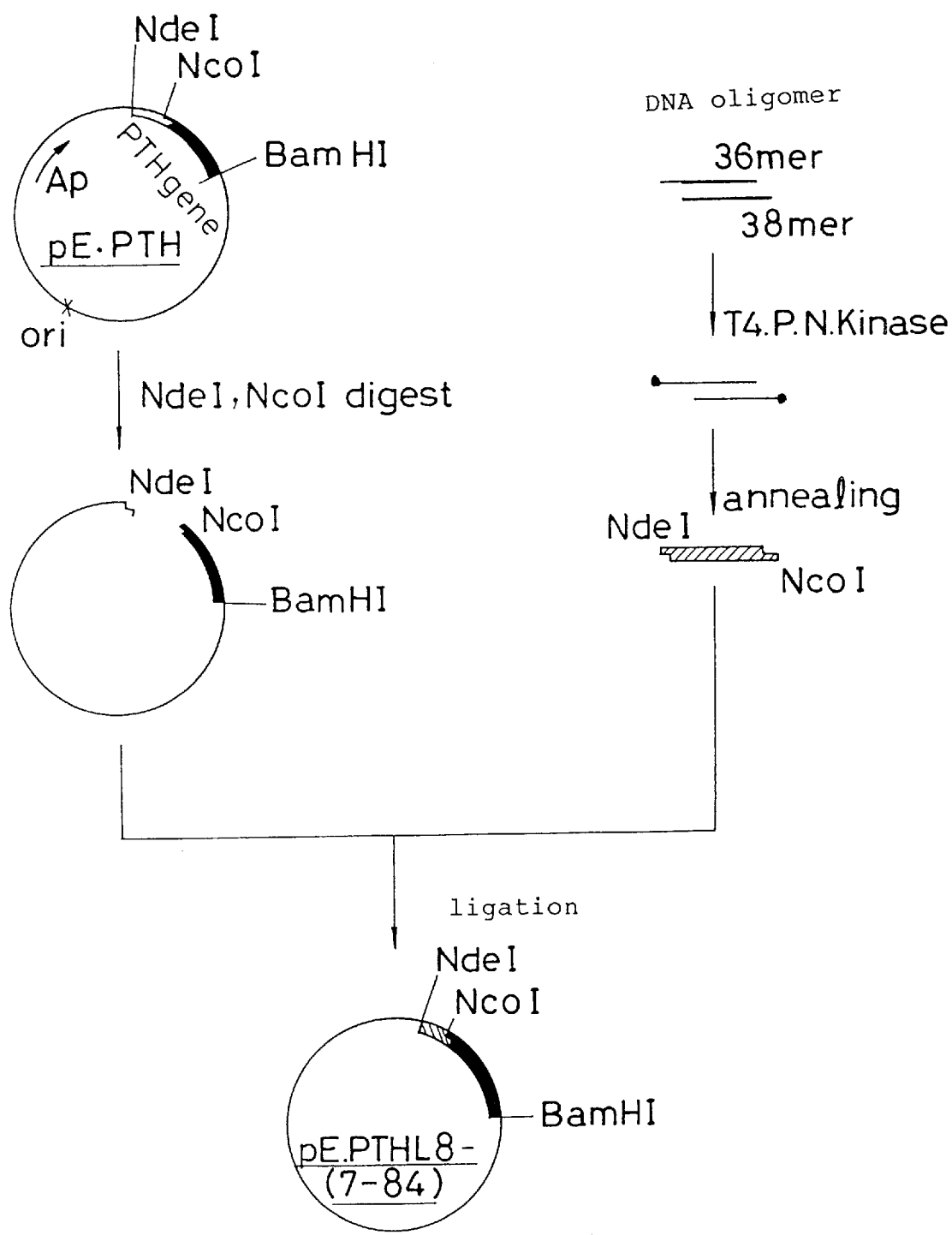

Lane 2: E. coli strain culture solution (10 82 l) carrying plasmid pE-L18PTH after addition of IPTG Lane 3: E. coli strain culture solution (10 μl) carrying plasmid pE-L18PTH without addition of IPTG;

FIG. 19 shows an HPLC chromatogram of purified [Leu$^{18}$] human PTH obtained in Example 3;

FIG. 20 shows an HPLC chromatogram of purified [Leu$^{8}$] human PTH obtained in Example 4;

FIG. 21 (SEQ ID NO:58)shows a DNA sequence and an amino acid sequence corresponding to [Leu$^{8}$] human PTH obtained in Example 4;

FIG. 22 shows the construction scheme for an expression plasmid of [Leu$^{8}$] human PTH (7–84) obtained in Example 5;

FIG. 23 shows results of SDS-PAGE after expression of a desired protein in Example 5:

Lane 1: Molecular weight marker,

Lanes 2 to 4: Whole cell lysate of MM294(DE3)/pE-L8PTH (7–84) induced by IPTG, in which [Leu$^{8}$] human PTH (7–84) is expressed, Lane 5: Whole cell lysate in which IPTG is added to E. coli having a gene coding for human PTH to express human PTH, Lane 6: Standard human PTH (1–84) (1 μg)

Figure 24:
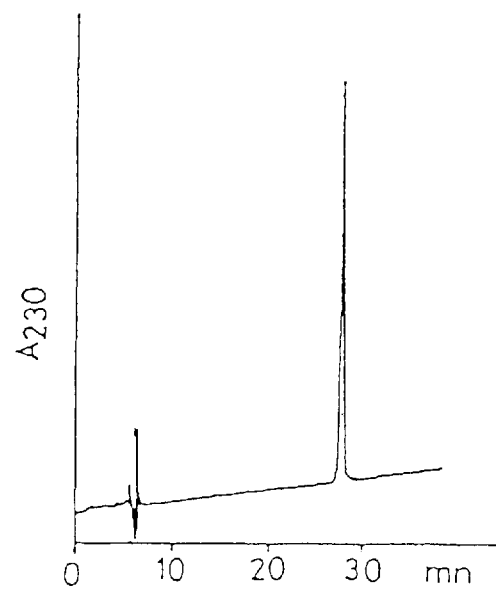
Figure 26:
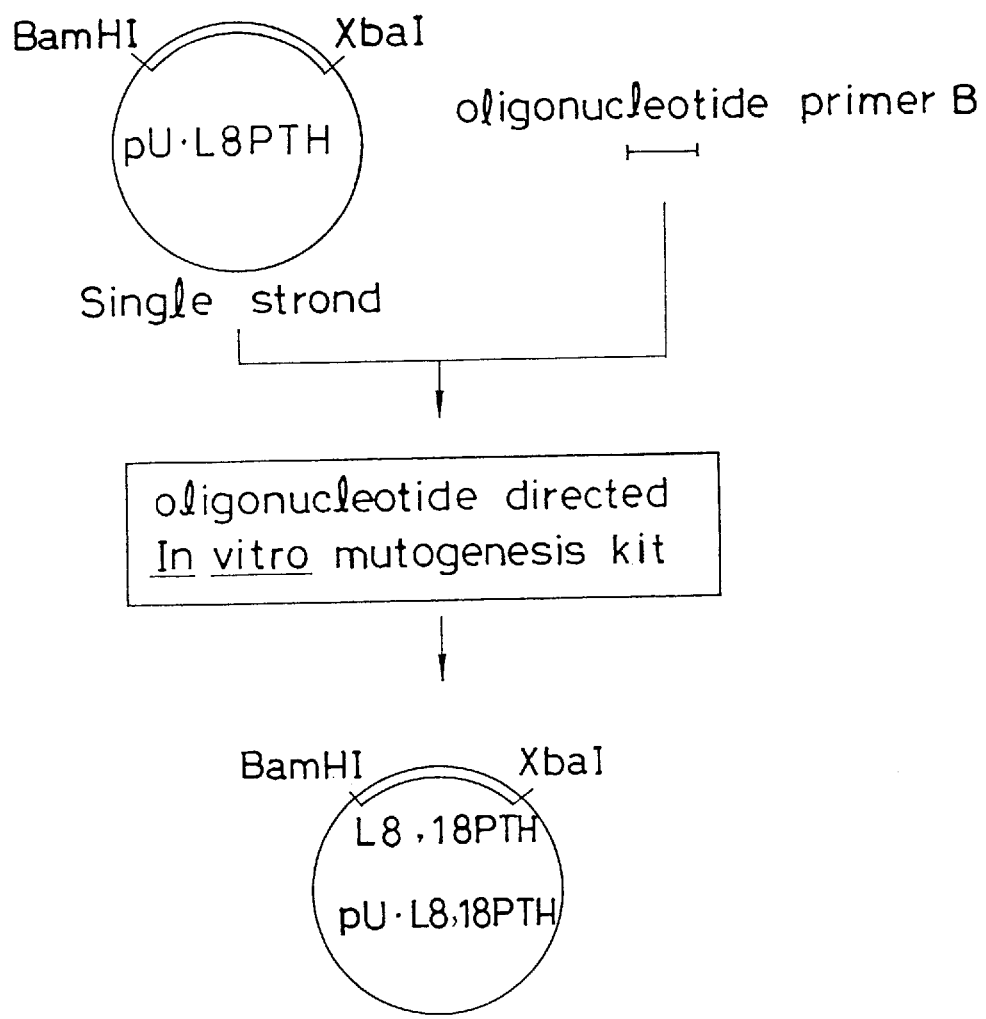
Figure 27:
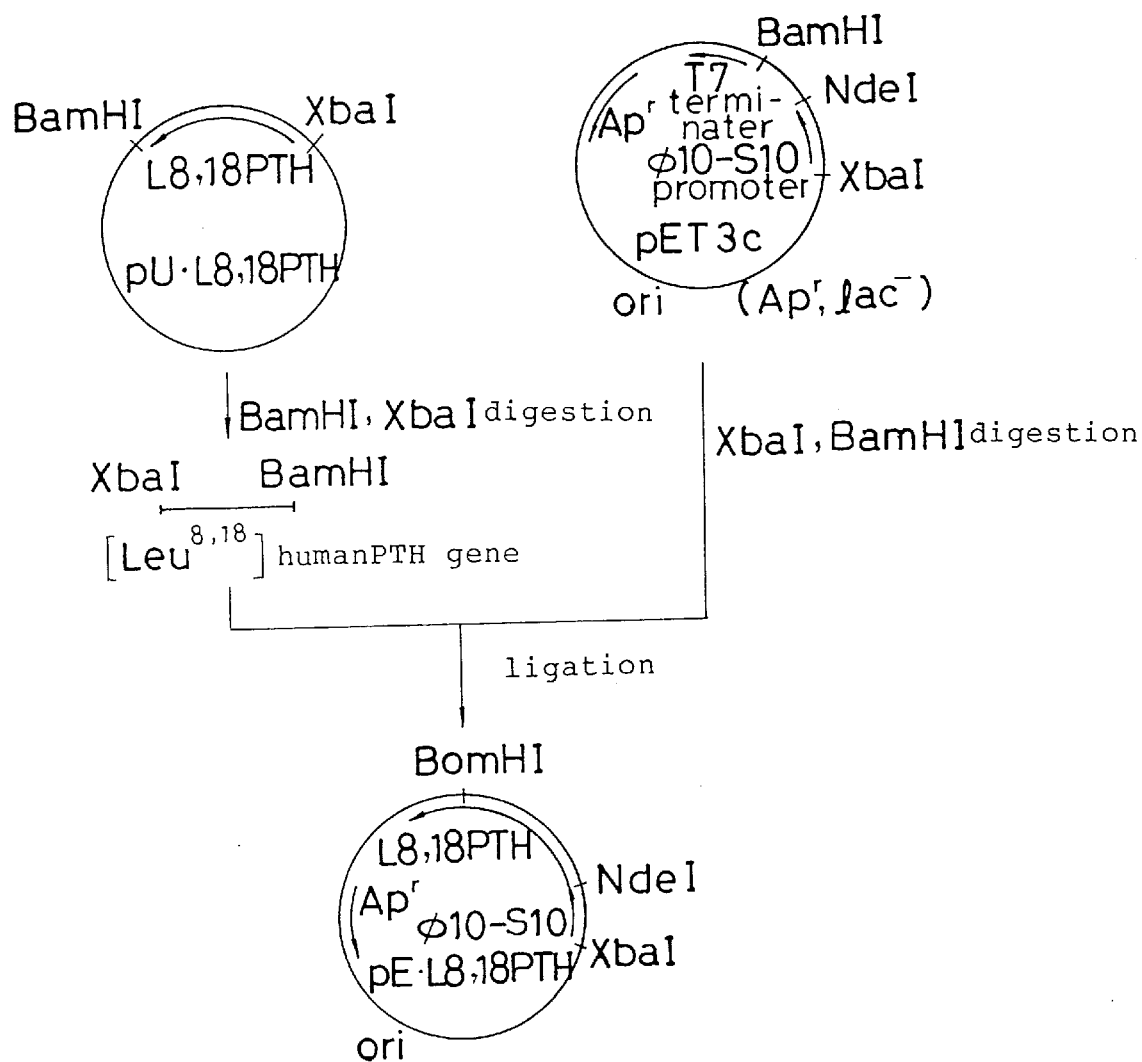
Figure 29:
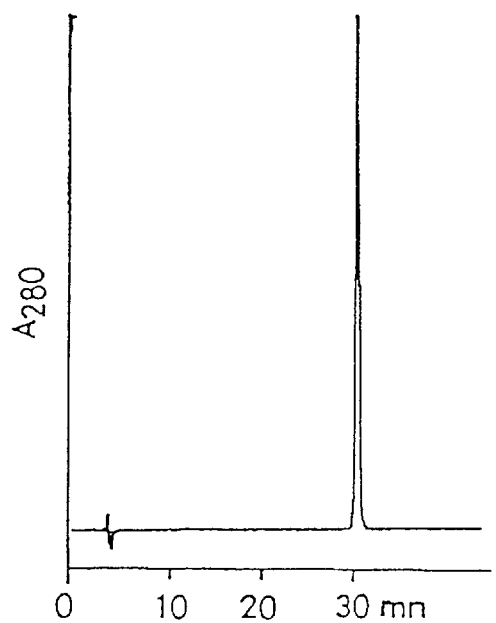

The gel was stained with Coomassie Blue;

FIG. 24 shows an HPLC chromatogram of purified [Leu$^{8}$] human PTH (7–84) obtained in Example 5;

FIG. 25 (SEQ ID NO:61) shows a DNA sequence and an amino acid sequence corresponding to [Leu8] human PTH (7–84) obtained in Example 5;

FIG. 26 shows the construction scheme for plasmid pU-L8,18PTH obtained in Example 6;

FIG. 27 shows the construction scheme for plasmid pE-L8,18PTH obtained in Example 6;

FIG. 28 (SEQ ID NO:62) shows a DNA sequence and an amino acid sequence corresponding to [Leu$^{8,18}$] human PTH obtained in Example 6; and FIG. 29 shows an HPLC chromatogram of purified [Leu$^{8,}$ $_{18}$] human PTH obtained in Example 6.

Figure 30:
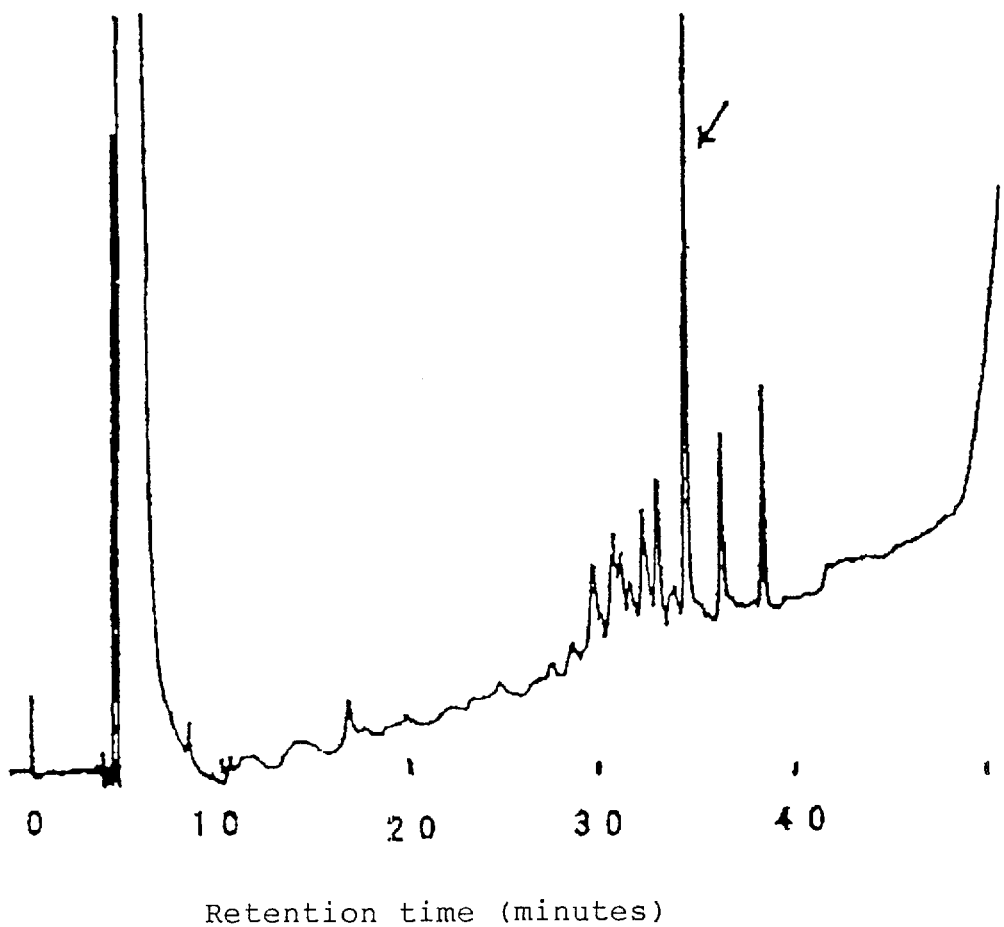

FIG. 30 shows a result of reverse phase HPLC column chromatography in Reference Example 4.

Figure 31:
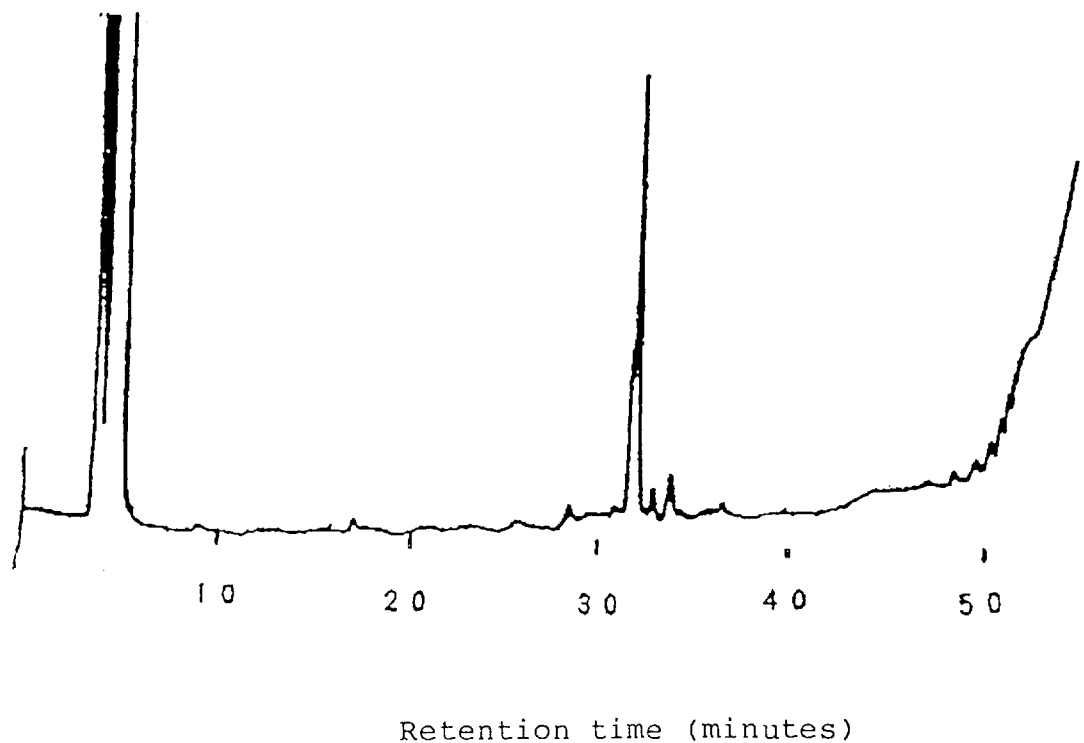

FIG. 31 shows a result of reverse phase HPLC column chromatography in Reference Example 5.

Figure 32:
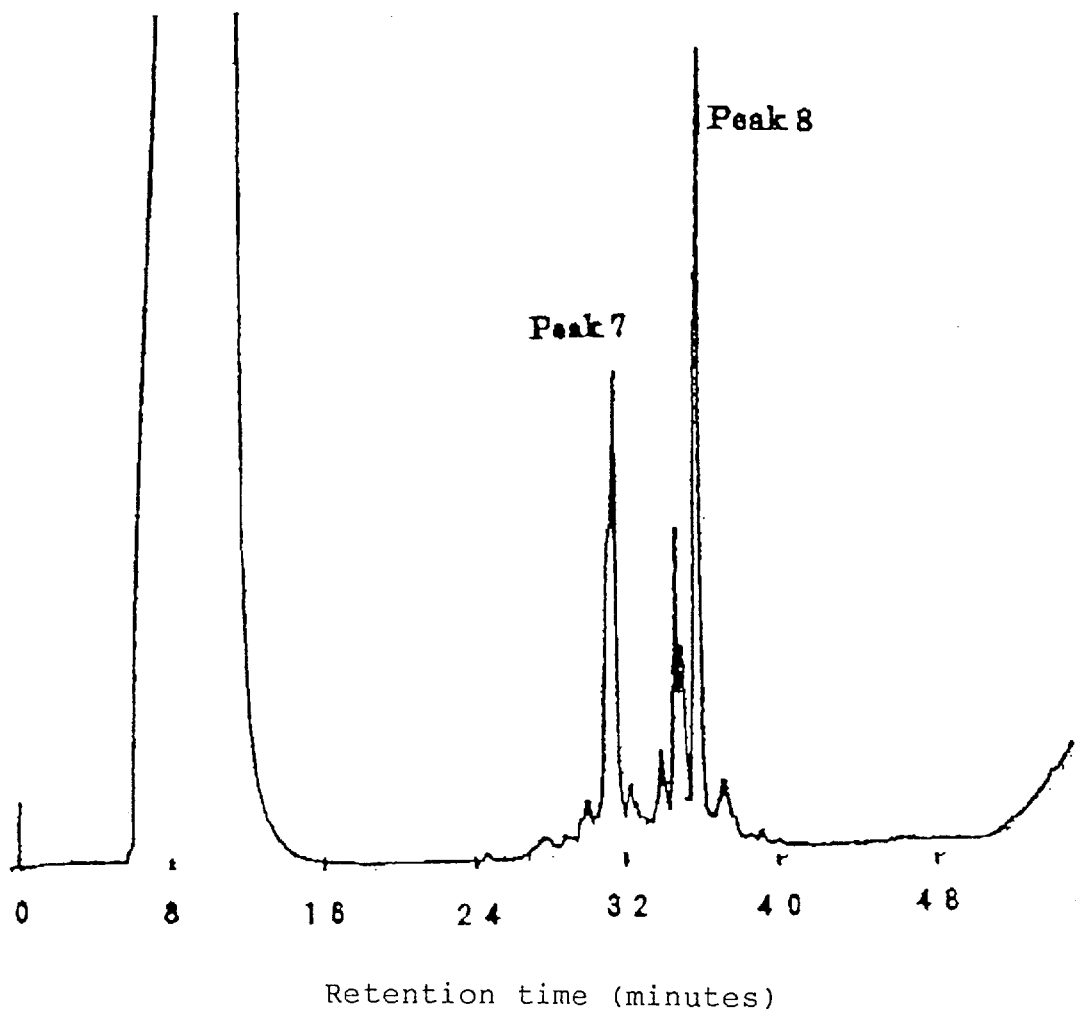

FIG. 32 shows a result of reverse phase HPLC column chromatography in Reference Example 6.

Figure 33:
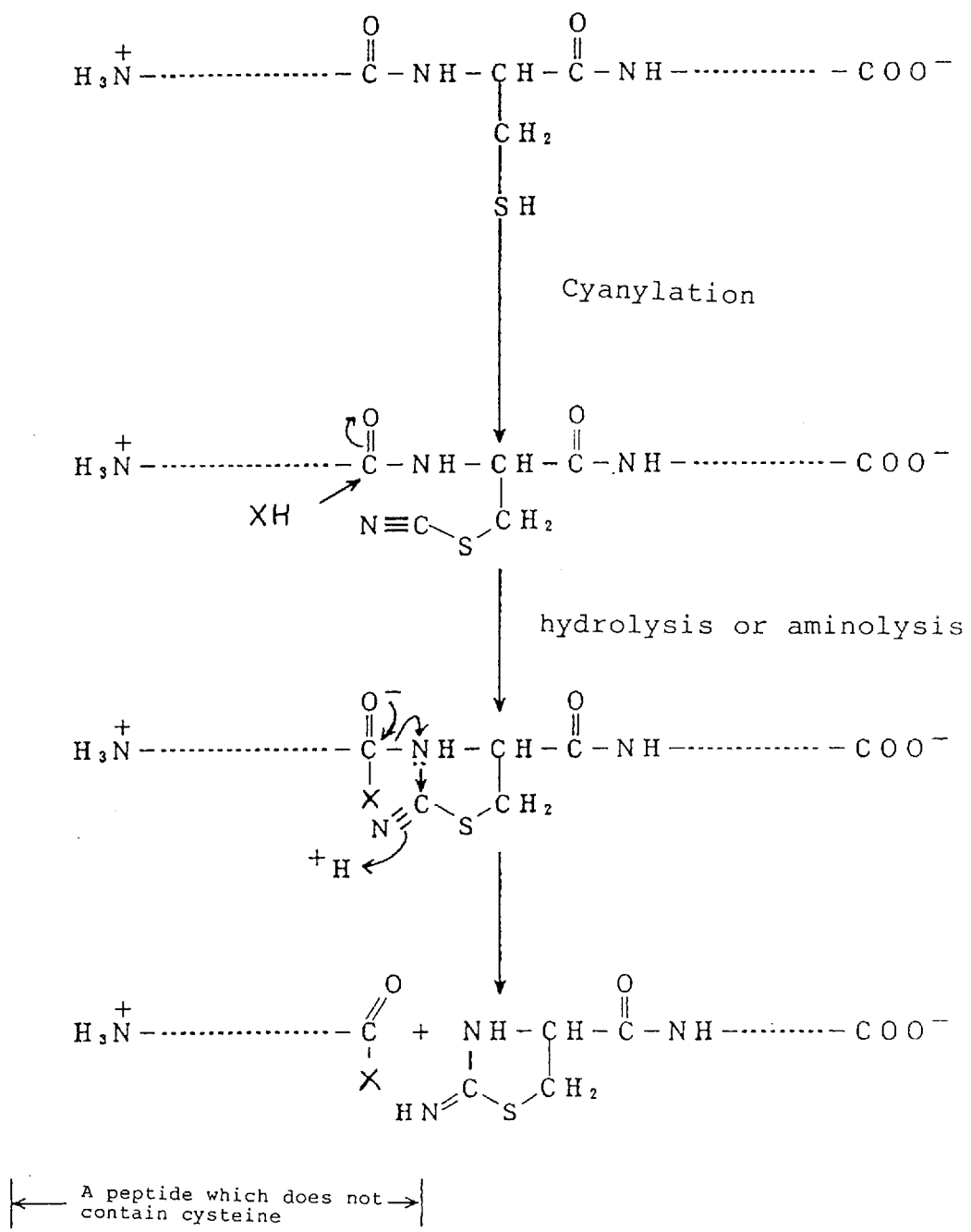

FIG. 33 shows a reaction mechanism of cleavage of human PTH.

DESCRIPTION OF THE PREFERRED EMBODIMENTS

For the PTH muteins of the present invention, any modification may be selected depending on their purpose, as long as it is at least one selected from (i), (ii) and (iii) described above. Furthermore, theses modifications may be combined. For example, the muteins which can be preferably used according to their purpose include a mutein in which N-terminal 2 to 6 amino acid residues are deleted and methionine residues are substituted by other lipophilic amino acid residues; a mutein in which N-terminal 2 to 6 amino acid residues are deleted and one amino acid residue within the region of amino acid residue Nos. 34 to 47 is substituted by a cysteine residue; a mutein in which at least one methionine residue is substituted by other lipophilic amino acid residue and one amino acid residue within the region of amino acid residue Nos. 34 to 47 is substituted by a cysteine residue; and a mutein in which N-terminal 2 to 6 amino acid residues are deleted, at least one methionine residue is substituted by other lipophilic amino acid residue and one amino acid residue within the region of amino acid residue Nos. 34 to 47 is substituted by a cysteine residue.

In the present invention, any lipophilic amino acid residue may be used for substitution for the methionine residue situated at the 8- or 18-position, as long as it is a lipophilic amino acid residue constituent in a naturally occurring protein. Examples of such lipophilic amino acid residues include aromatic amino acid residues such as phenylalanine, tyrosine and tryptophan, and relatively long-chain aliphatic amino acid residues such as isoleucine, leucine and valine.

Examples of the human parathyroid hormone muteins of the present invention include a peptide represented by the following general formula (I) and salts thereof:

$R_1$-$R_2$-His-Asn-Leu-Gly-Lys-His-Leu-Asn-Ser-$R_3$-Glu-Arg-Val-Glu-Trp-Leu-Arg-Lys-Lys-Leu-Gln-Asp-Val-His-Asn-$R_4$-$R_5$-Ala-$R_6$-Gly-$R_7$-Pro-$R_8$-Ala-$R_9$-$R_{10}$-Asp-Ala-Gly-Ser-Glu-Arg-Pro-Arg-Lys-Lys-Glu-Asp-Asn-Val- Leu-Val-Glu-Ser-His-Glu-Lys-Ser-Leu-Gly-Glu-Ala-Asp-Lys-Ala-Asp-Val-Asn-Val-Leu-Thr-Lys-Ala-Lys-Ser-Gln (I)

wherein $R_1$ represents Leu (SEQ ID:NO:1), Gln-Leu (SEQ ID:NO:2), Ile-Gln-Leu (SEQ ID:NO:3), Glu-Ile-Gln-Leu (SEQ ID NO:4) or Ser-Val-Ser-Glu-Ile-Gln-Leu (SEQ ID:NO:5); $R_2$ represents Leu, Ile, Val or Met; $R_3$ represents Leu, Ile, Val or Met; $R_4$ represents Cys or Phe; $R_5$ represents Cys or Val; $R_6$ represents Cys or Leu; $R7$ represents Cys or Ala; $R_8$ represents Cys or Leu; $R_9$ represents Cys or Pro; and $R_{10}$ represents Cys or Arg, with the proviso that the same structure as that of human parathyroid hormone is excluded.

Figure 7:
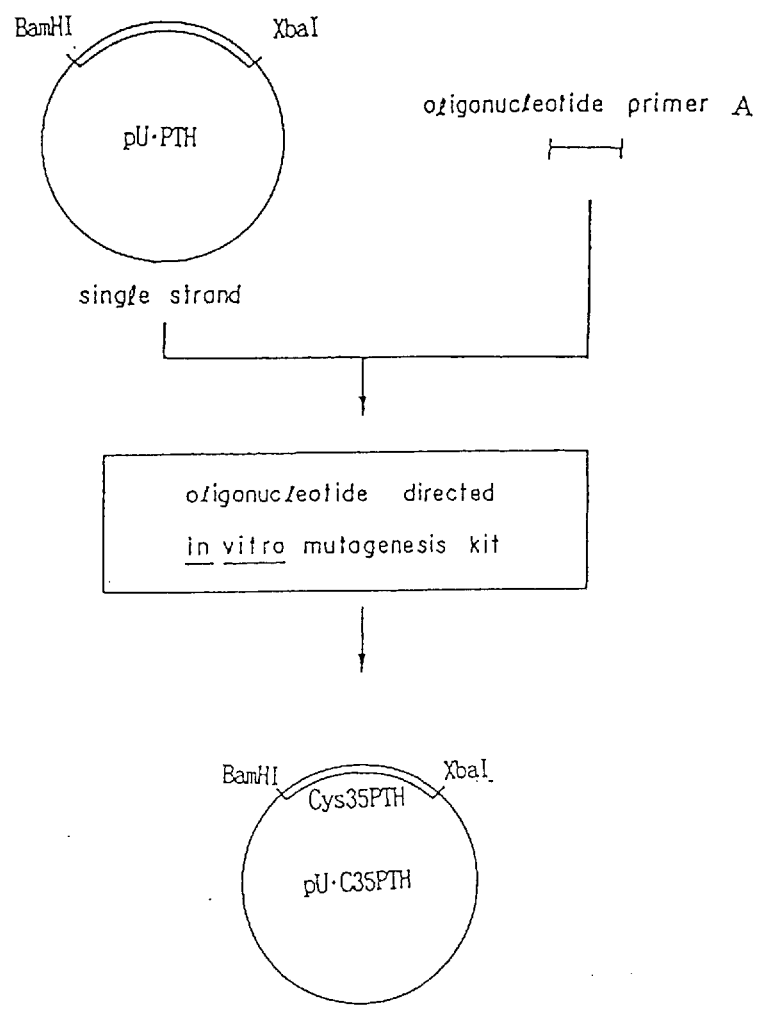
FIG. 7 shows the construction scheme for plasmid pU-C35PTH obtained in Example 2.

In order to produce the human PTH mutein of the present invention, a gene coding for the amino acid sequence of human PTH (1–84) (for example, European Unexamined Patent Publication No. 483509) is converted to a gene coding for the desired mutein using a conventional DNA technique, for example, site-directed mutagenesis (for example, FIG. 7). As to the N-terminal portion lacking human PTH muteins, for example, antagonist derivatives lacking N-terminal amino acid sequences such as Ser-Val-Ser, Ser-Val-Ser-Glu, (amino acids 1–4 of SEQ ID NO:5) Ser-Val-Ser-Glu-Ile (amino acids 1–5)and Ser-Val-Ser-Glu-Ile-Gln (amino acids 1–6 of SEQ ID NO:6 (FIG. 1), genes of human PTH (4–84), human PTH (5–84), human PTH (6–84) and human PTH (7–84) (FIG. 2) (SEQ ID NOs: 24 to 31) are first prepared from synthetic oligomers (FIGS. 3 and 4), and inserted into vectors (FIG. 5). With respect to muteins further subjected to the amino acid substitution, the site-directed mutagenesis is applied to the corresponding genes, respectively, to obtain the desired genes. This mutagenesis, which is well known, is described in R. F. Lather and J. P. Lecoq, *Genetic Engineering*, Academic Press, p.31–50 (1983). Mutagenesis directed to oligonucleotide is described in M. Smith and S. Gillam, *Genetic Engineering: Principles and Methods*, Plenum Press, vol.3, p.1–32 (1981).

Structural genes coding for the various muteins of the present invention different in chain length subjected to the amino acid substitution are produced, for example, by he steps of:

(a) hybridizing single-stranded DNAs each of which comprises one strand of a structural gene of human PTH with mutagenic oligonucleotide primers, (b) elongating the primers with DNA polymerase to form mutational heteroduplexes, and (c) replicating the mutational heteroduplexes.

The size of the oligonucleotide primer depends on conditions required for stable hybridization of the primer to a gene region to which mutation is to be introduced, and on limitations in currently available methods of oligonucleotide synthesis. The factors (for example, the overall size and the size of a mismatching portion at a mutation site) to be considered in designing the oligonucleotide used for mutagenesis directed by the oligonucleotide are described by M. Smith and S. Gillam in the above literature. In general, the overall length of the oligonucleotide is such a length that stable, unique hybridization at the mutation site is optimized, and the extensions from the mutation site to the 5'- and the 3'-termini are adjusted in size so as to be sufficient to prevent mutation editing due to the exonuclease of DNA polymerase. The oligonucleotides used for mutagenesis in accordance with the present invention usually contain about 12 to about 40 nucleotides, and preferably about 14 to about 24 nucleotides. These usually contain at least about 3 nucleotides on the 3'-terminal side from the codon to be changed.

For example, for the purpose of obtaining a mutein whose constituent amino acid, valine, is substituted by cysteine, site-directed mutagenesis is conducted, using a synthetic nucleotide primer which changes a valine codon to a cysteine codon, thereby producing a modified human PTH gene.

For example, in order to change methionine at the 8-position of human PTH to leucine, the primer is hybridized with an anti-sense chain of the human PTH gene. Preferred examples of the nucleotide primers include 5'-TCCGAGATTCAG<u>CTG</u>CTGCATAACCTT-3' (SEQ ID NO:6).

When the methionine is changed to isoleucine, examples of the nucleotide primers include 5'-TCCGAGATTCAG<u>ATC</u>CTGCATAACCTT-3' (SEQ ID NO:7).

When the methionine is changed to threonine, examples of the nucleotide primers include 5'-TCCGAGATTCAG<u>ACG</u>CTGCATAACCTT-3' (SEQ ID NO:8).

Preferred primers used when methionine at the 18-position is changed to leucine include 5'-ACATTTGAACTCG<u>CTG</u>GAGGGTGTAGAA-3' (oligonucleotide primer B) (SEQ ID NO:9).

Primers for changing the above site to isoleucine include

5'-ACATTTGAACTCG<u>ATC</u>GAGGGTGTAGAA-3' (SEQ ID NO:10).

When the site is changed to threonine, primers include

5'-ACATTTGAACTCG<u>ACG</u>GAGGGTGTAGAA-3' (SEQ ID NO:11).

Preferred primers used when phenylalanine at the 34-position is changed to cysteine include 5'-GATGTGCACAAT<u>TGT</u>GTTGCCTTAGGTGCC-3' (SEQ ID NO:12).

Further, preferred primers used site-directed mutagenesis, respectively include

5'-CACAATTTT<u>TGC</u>GCCTTAGG-3' (oligonucleotide primer A) (SEQ ID NO:13), when valine at the 35-position is changed to cysteine, 5'-AATTTTGTTGCC<u>TGT</u>GGTGCCCCATTG-3' (SEQ ID NO:14), when leucine at the 37-position is changed to cysteine, 5'-GTTGCCTTAGGTTGCCCATTGGCTCCT-3' (SEQ ID NO:15), when alanine at the 39-position is changed to cysteine, 5'-TTAGGTGCCCCATGTGCTCCTCGTCAT-3' (SEQ ID NO:16), when leucine at the 41-position is changed to cysteine, 5'-GCCCCATTGGCTTGTCGTGATGCTGGT-3' (SEQ ID NO:17), when proline at the 43-position is changed to cysteine, and 5'- CCATTGGCTCCT TGTGATGCTGGTTCC-3' (SEQ ID NO:18), when arginine at the 44-position is changed to cysteine.

Other nucleotide primers can be made by those skilled in the art using conventional techniques.

The primer is hybridized to a single-stranded phage in which a single strand of the human PTH gene is cloned, such as M13 [Yanisch-Perror, C. Vieira and J. Messing, *Gene,* 33, 103–119 (1985); J. Messing, *Methods in Enzymology,* 101, 20–78 (1983)], fd [R. Herrman et al., *Mol. Gen. Genet.,* 177, 231 (1980)] or φ×174 [M. Smith and S. Gillam, *Genetic Engineering,* Plenum Press, vol.3, p.1–32 (1981)], or to a chimera vector of a phage and a plasmid such as pUC118 or pUC119 [J. Vieira and J. Messing, *Methods in Enzymology,* 153, 3–11 (1987)]. It is observed that the phage can carry both a sense chain and an anti-sense chain of the gene. When the phage carries the anti-sense chain, in addition to discrepancy from the codon determining a triplet which has encoded another amino acid, the primer may not be the same as a sense chain region containing a codon to which mutation is to be induced, due to codon degeneracy. Similarly, when the phage carries the sense chain, the primer may not be complementary to the sense chain region containing a codon to which mutation is to be induced, as well as appropriate discrepancy from a triplet which pairs to a codon to be deleted. The conditions used for hybridization are described by M. Smith and S. Gillam in the above literature. The temperature is usually within the range from about 0° to about 70° C., and more generally within the range from about 10 to about 50° C. After hybridization, the primer is elongated on a phage DNA by reaction with *E. coli* DNA polymerase I, T4 DNA polymerase, a reverse transcriptase or another suitable DNA polymerase. The resulting double-stranded DNA (dsDNA) is converted to a closed circular dsDNA by treatment with a DNA ligase such as T4 DNA ligase. DNA molecules containing single-stranded regions can be decomposed by S1 endonuclease treatment.

The resulting mutational heteroduplex is used for transformation of infectable host organisms or cells. In the replication of the heteroduplex by using the host, progenies are produced from both chains. Following the replication, a mutant gene is isolated from the progeny of the mutant chain, and inserted into an appropriate vector. The resulting vector is used for transformation of appropriate host organisms or cells.

Then, the phage DNA carrying the mutational gene is isolated, and incorporated into a plasmid.

Examples of the plasmids into which DNAs are incorporated include plasmids derived from *E. coli,* such as pBR322 [*Gene* 2, 95 (1977)], pBR325 [*Gene* 4, 121 (1978)], pUC12 [*Gene* 19, 259 (1982)] and pUC13 [*Gene* 19, 259 (1982)]; and plasmids derived from *Bacillus subtilis,* such as pUB110 [*Biochemical and Biophysical Research Communication,* 112, 678 (1983)]. However, any other plasmid may be used, as long as it is replicable and maintainable in the host.

Examples of methods for incorporating the phage DNA into the plasmid include the method described in T. Maniatis et al., *Molecular Cloning,* Cold Spring Harbor Laboratory, p.239 (1982).

The genes coding for peptides lacking N-terminal regions of human PTH (1–84) include, for example, genes having sequences (SEQ ID NOs:19 to 22) shown in FIG. 1, and these genes can also be obtained by synthesis. In FIG. 1, amino acid sequences are also shown in addition to DNA sequences used in the present invention. In addition, a gene coding for human PTH (1–84) and its amino acid sequence (SEQ ID NO:23) are also shown in FIG. 1.

When the above genes are used for expression, an initiation codon ATG and a stop codon (for example, TAA) are directly arranged on the 5'- and 3'-terminal sides, respectively, of the sequence of each polypeptide lacking the N-terminal region of human PTH, and for example, NdeI and BamHI are ligated to the 5'- and 3'-termini, respectively, for insertion into a vector, as shown in FIG. 2 (SEQ ID NOs:24 to 31). In FIG. 2 are also shown sequences (SEQ ID NOs:32 and 33) in which the above-mentioned initiation codon and stop codon are added to the gene coding for human PTH (1–84).

In synthesizing the human PTH-related gene of the present invention, its structural gene is finally cleaved into 14 fragments, for example, as shown in FIG. 2. The respective DNA fragments are shown in FIG. 3, and fragments #1-e, #2-e and #3 to #14 (SEQ ID NOs:42 to 55) were already provided by the present inventors (European Unexamined Patent Publication No. 477885).

Methods for cleaving the gene into the fragments are not required to be limited to the above-mentioned method, and various methods are also available as long as the method avoids self association.

Fragments #1 to #14 (SEQ ID NOs:34 to 55) can be produced by known synthesizing methods. For the fragments except for #1 and #14, the 5'-termini are phosphorylated with polynucleotide kinase as required, and all of the fragments are hybridized at once to ligate them to one another with DNA ligase (FIG. 4), or the phosphorylated fragments first divided into two or three groups are hybridized to form a double-stranded DNA fragment with DNA ligase, and the DNA fragments of the respective groups were further ligated to one another with DNA ligase, thereby obtaining a complete double-stranded human PTH gene.

The resulting gene is ligated to a digested product of pUC19 with NdeI and BamHI to obtain a novel plasmid pU-PTH-C19, and *E. coli* JM109 is transformed. As to the isolated plasmid, the nucleotide sequence is determined by the Sanger method using a portion of the DNA fragment as a primer. More easily, the DNA fragment obtained by digestion with NdeI and BamHI is digested with AurII, NcoI, HgiAI or AluI to give a correct restriction site, thereby confirming the existence of the human PTH gene lacking the N-terminal portion. Further, this gene can be changed to the derivatives in which leucine is substituted for methionine at the 8- and 18-positions and cysteine is substituted for various amino acid residues at the 34- to 47-positions by site-directed mutagenesis.

The gene thus cloned is ligated downstream from a promoter in a vehicle (vector) suitable for expression, whereby an expression vector can be obtained.

The vectors include the above-mentioned plasmids derived from *E. coli* (such as pBR322, pBR325, pUC12 and pUC13), plasmids derived from *B. subtilis* (such as pUB110, pTP5 and pC194), plasmids derived from yeast (such as pSH19 and pSH15), bacteriophages such as λ phage, and animal viruses such as retroviruses and vaccinia viruses.

The gene has ATG as an initiation codon at the 5'-terminus thereof and may have TAA, TGA or TAG as a stop codon at the 3'-terminus. In order to express the gene, a promoter is ligated upstream therefrom. As the promoter used in the present invention, any promoter is available as long as it is suitable for expression corresponding to the host used for the gene expression.

When the host cell used for transformation is Escherichia, it is preferable to use a trp promoter, a lac promoter, a recA promoter, a λPL promoter, a lpp promoter, a pharge T7φ10 promoter and the like. When the host cell is Bacillus, it is preferable to use an SPO1 promoter, an SPO2 promoter, a penP promoter and the like. When the host cell is yeast, it is preferable to use a PHO5 promoter, a PGK promoter, a GAP promoter, an ADH promoter and the like. In particular, it is preferable that the host cell is Escherichia and the promoter is a trp promoter, a λPL promoter or a pharge T7φ10 promoter.

When the host cell is an animal cell, an SV40-derived promoter, a retrovirus promoter or the like can be used. The SV40-derived promoter is preferably used among others.

By using the vector containing the recombinant DNA having a nucleotide sequence coding for the mutein thus constructed, a transformant for carrying the vector is prepared.

The host cells include, for example, Escherichia, Bacillus, yeast and animal cells.

Examples of the cells belonging to the genus Escherichia described above include *E. coli* K12DH1[*Proc. Natl. Acad. Sci. U.S.A.*, 60, 160 (1968)], JM103 [*Nucleic Acids Research*, 9, 309 (1981)], JA221 [*Journal of Molecular Biology*, 120, 517 (1978)], HB101 [*Journal of Molecular Biology*, 41, 459 (1969)], C600 [*Genetics*, 39, 440 (1954)], MM294 [*Proc. Natl. Acad. Sci. U.S.A.*, 73, 4174 (1976)] and MM29 4(DE3)/pLysS (Japanese Patent Unexamined Publication No. 3-43088/1991).

Examples of the cells belonging to the genus Bacillus described above include *Bacillus subtilis* MI 114 [*Gene*, 24, 255 (1983)] and 207-21 [*Journal of Biochemistry*, 95, 87 (1984)].

Examples of the yeast include *Saccharomyces cerevisiae* AH22R, NA87-11A and DKD-5D.

Examples of the animal cells include monkey cell COS-7, Vero, Chinese hamster cell (CHO), mouse L cell and human FL cell.

The transformation of Escherichia strains described above is conducted, for example, according to the method described in *Proc. Natl. Acad. Sci. U.S.A.*, 69, 2110 (1972), *Gene*, 17, 107 (1982) or the like.

The transformation of Bacillus strains is carried out, for example, according to the method described in *Molecular & General Genetics*, 168, 111 (1979) or the like.

The transformation of yeast is performed, for example, according to the method described in *Proc. Natl. Acad. Sci. U.S.A.*, 75, 1929 (1978).

The transformation of animal cells is carried out, for example, according to the method described in *Virology*, 52, 456 (1973).

Thus, the transformant transformed with the vector containing the recombinant DNA having the nucleotide sequence coding for the mutein is obtained.

The mutein is produced by cultivating the transformant in a culture medium.

When bacterial transformants are cultivated, a liquid medium is suitably used for cultivation. Carbon sources, nitrogen sources, inorganic compounds and other nutrients necessary for growth of the transformants are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast, vitamins and growth promoting factors may be further added thereto.

The pH of the medium is preferably about 6 to about 8.

When the Escherichia transformants are cultivated, M9 medium containing glucose and Casamino Acids [Miller, *Journal of Experiments in Molecular Genetics*, 431–433, Cold Spring Harbor Laboratory, N.Y. (1972)] is preferably used to cultivate the transformants. In order to allow the promoters to act more efficiently, for example, drugs such as 3β-indolyl acrylic acid and isopropyl βD-thiogalactopyranoside may be added thereto if necessary.

The Escherichia transformants are usually cultivated at about 15 to about 43° C. for about 3 to about 24 hours with aeration or agitation if necessary.

The Bacillus transformants are usually cultivated at about 30 to about 40° C. for about 6 to about 24 hours with aeration or agitation if necessary.

When the yeast transformants are cultivated, the preferred medium is Burkholder minimum medium [K. L. Bostian, *Proc. Natl. Acad. Sci. U.S.A.*, 77, 4505 (1980)]. The pH of the medium is preferably adjusted to about 5 to about 8. The cultivation is usually carried out at about 20 to about 35° C. for about 24 to about 72 hours with aeration or agitation if necessary.

When the animal cell transformants are cultivated, examples of media which can be used include MEM medium containing about 0 to about 20% fetal calf serum [*Science*, 122, 501 (1952)], DME medium [*Virology*, 8, 396 (1959)], RPMI1640 medium [*Journal of the American Medical Association*, 199, 519 (1967)] and 199 medium [*Proceeding of the Society for the Biological Medicine*, 73, 1 (1950)]. The pH is preferably about 6 to about 8. The cultivation is usually carried out at about 30 to about 40° C. for about 15 to about 60 hours, with aeration or agitation if necessary.

The isolation and purification of the mutein from the above-mentioned culture products can be carried out, for example, according to the following method.

First, the cultivated cells are disrupted to extract the contents. The disruption is conducted by various methods using a French press, ultrasonic waves, lysozyme, freeze-thawing, glass beads and the like. However, any method may be used. When the cells are disrupted, 1–8M urea or 1–6M guanidine hydrochloride (Gu-HCl) may be added to a buffer solution. A reducing agent such as dithiothreitol is added to increase the recovery of the desired mutein in some cases. The reducing agent is added after lysozyme has been reacted.

Then, the above-mentioned extract is subjected to centrifugation to separate a supernatant from a precipitate. When the mutein is recovered in the supernatant, it can be effectively purified, for example, according to a method similar to the method described in M. Iwane et al., *Biochem. Biophys. Res. Commun.*, 146, 470–477 (1987). When the mutein is recovered in the precipitate, this precipitate is dissolved in a solution containing a protein denaturant such as urea or guanidine hydrochloride, followed by dialysis or dilution to decrease the concentration of the denaturant, whereby the biologically active mutein can be obtained. The mutein recovered from the precipitate is purified as so desired, which leads to a high purity, high active product similarly with the mutein recovered from the supernatant.

In particular, for the mutein containing Cys, the coexistence of a slight amount of the reducing agent in the purification course or the storage course is suitable for preventing the product from being oxidized. Human PTH can be separated from extracted solutions and purified by the use of known techniques. The separating and purifying techniques include column chromatography such as gel filtration, ion exchange chromatography using a cation exchange resin or an anion exchange resin, column chromatography such as hydrophobic chromatography and partition adsorption chromatography, and high performance liquid chromatography.

The cultivation of the transformants of Bacillus, yeast and animal cells and the separation and purification of human PTH from the culture products are carried out by methods known per se in the art.

The resulting human PTH mutein of the present invention are useful as therapeutic drug. When the resulting human PTH mutein is an agonist derivative, it can be used as therapeutic agents for various diseases caused by the abnormality of calcium metabolism, for example, osteoporosis and hypoparathyroidism, and as therapeutic agents for hypertension. Further, the human PTH antagonist derivatives can be used as therapeutic agents for hypercalcemia and hyperparathyroidism. The dosage thereof is properly determined in each case, taking into account the object of administration, the disease and the like, and a suitable amount is given within the range of about 1 ng to about 100 $\mu$g/kg of weight a day. Usually, human PTH derivative of the present invention is mainly given parenterally in combination with pharmaceutically acceptable carriers, excipients or diluents as injections, nasotracheal agents, perrectum agents, transvaginal agents or percutaneous agents, but it may be given orally in some cases.

The human PTH mutein in which one amino acid residue within the region of amino acid residue Nos. 34 to 47 is substituted by a cysteine residue is subjected to cleavage reaction to cleave peptide bonds on the amino group side of the cysteine residue and can be used for the production of various fragments different in chain length which have the biological activity of human PTH.

Examples of the cleavage reaction include cyanylation, hydrolysis or aminolysis.

The cyanylation reaction is conducted by reacting an S-cyanylating reagent with a partially purified material compound.

Examples of the S-cyanylating reagents include 2-nitro-5-thiocyanobenzoic acid (NTCB), 1-cyano-4-dimethylamino-pyridinium salts (DMPA-CN) and CN_ions. The amount of the S-cyanylating reagents used is about twice to about 50 times as much as all thiol groups, and more preferably, about 5 to about 10 times.

The reaction temperature may be any as long as it is within the range of about 0° to about 80° C. A temperature of about 0° to about 50° C. is more preferably used. Any buffer may be used as a solvent as long as it does not react with the cyanylating reagent. Examples of such buffer solutions include Tris-HCl buffer, Tris-acetate buffer, phosphate buffer and borate buffer. An organic solvent may be used as long as it does not react with the cyanating reagent.

The reaction is carried out in pH range about 1 to about 12. Further, pH 7 to 10 is preferable when NTCB is used. And pH 2 to 7 is preferable to prevent S—S exchange reaction when DHAP-CN is used. Denaturation agent, such as guanidinechloride, may be used in the reaction solution.

The above-mentioned hydrolysis or aminolysis is conducted by subjecting the starting material product to alkali treatment. The alkali treatment is carried out by adjusting a solution containing the starting material to pH 7–14.

The adjustment of the pH is performed, for example, by adding an appropriate amount of a solution of sodium hydroxide, ammonium, a substituted amino compound, trituma base [Tris(hydroxymethyl)-aminomethane], sodium dihydrogenphosphate, potassium hydroxide, barium hydroxide or the like to the solution containing the cyanated compound. The substituted amino compounds include the above-mentioned compounds.

The concentration of the solution in the above-mentioned reaction is, for example, about 0.01 to about 2 N, preferably about 0.1 to about 1N for sodium hydroxide, about 0.01 to about 15N, preferably about 0.1 to about 3N for ammonium or substituted amino compounds, about 1 mM to about 1M, preferably about 20 mM to about 200 mM for trituma base, about 1 mM to about 1M, preferably about 10 mM to about 100 mM for sodiumic phosphate, about 0.01 to about 4N, preferably about 0.1 to about 2N for potassium hydroxide, and about 0.01 to about 0.2M, preferably about 0.1 to about 0.2M for barium hydroxide. The reaction temperature may be any as long as it ranges from about 0° C. to about 80° C. A temperature of about 0° to about 50° C. is more preferably used.

The reaction time is preferably about 1 to about 60 minutes, more preferably about 15 to about 30 minutes for cyanylation reaction, about 5 minutes to about 100 hours, preferably about 10 minutes to about 15 hours for hydrolysis, and about 5 minutes to about 24 hours, preferably about 10 to about 180 minutes for aminolysis.

The reaction shown in FIG. 33 is considered to take place by the above-mentioned cyanylation and hydrolysis or aminolysis. In FIG. 33, X represents OH or R—NH—(wherein R—NH— represents an amino group or a substituted amido group). In this reaction, when ammonium or the substituted amino compound is used, a corresponding amide compound or substituted amide compound is obtained.

The peptide fragments cut out are isolated according to known methods for purifying peptides, for example, by suitable combinations of gel filtration, ion-exchange chromatography, high performance liquid chromatography, affinity chromatography, hydrophobic chromatography, thin layer chromatography, electrophoresis and the like. Methionine derived from the initiation codon is sometimes attached to the N-terminus of the peptide fragment obtained here.

The resulting peptide fragments may be lyophilized if necessary. In lyophilization, stabilizers such as sorbitol, mannitol, dextrose, maltose, trehalose and glycerol may be added.

In the present invention, for human PTH (1–84) and the antagonists lacking its N-terminal amino acid sequences, the respective genes are subjected to site-directed mutagenesis, and the methionine residues are changed to other lipophilic residues by expression of the resulting modified genes, thereby forming the anti-oxidative muteins. Further, the muteins in which various amino acid residues in the central portions of the polypeptide are changed to cysteine are prepared. Such muteins can form dimers. Furthermore, various substituent groups (for example, lipophilic alkyl groups) are introduced into the side chains of the cysteine residues, whereby the human PTH agonist muteins and antagonist muteins can be stabilized, the activity can be enhanced, and the absorption to the tissues can be improved. Thus, the present invention provides the human PTH muteins useful for clinical application.

When nucleotides, amino acids and so on are indicated by abbreviations in the specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA:Deoxyribonucleic acid
A:Adenine
T:Thymine
G:Guanine
C:Cytosine
RNA:Ribonucleic acid
dATP:Deoxyadenosine triphosphate
dTTP:Deoxythymidine triphosphate
dGTP:Deoxyguanosine triphosphate
dCTP:Deoxycytidine triphosphate
ATP:Adenosine triphosphate
Tdr:Thymidine
EDTA:Ethylenediaminetetraacetic acid
SDS:Sodium dodecyl sulfate
Gly or G:Glycine
Ala or A:Alanine
Val or V:Valine
Leu or L:Leucine
Ile or I:Isoleucine
Ser or S:Serine
Thr or T:Threonine
Cys or C:Cysteine
Met or M:Methionine
Glu or E:Glutamic acid
Asp or D:Aspartic acid
Lys or K:Lysine
Arg or R:Arginine
His or H:Histidine
Phe or F:Phenylalanine
Tyr or Y:Tyrosine
Trp or W:Tryptophan
Pro or P:Proline
Asn or N:Asparagine
Gin or Q:Glutamine The present invention will be described in more detail through following reference examples and examples. It is understood of course that these examples are not intended to limit the scope of the invention.

Transformants E. coli MM294(DE3)/pE-L8PTH and E. coli MM294(DE3)/pE-C35PTH obtained in examples described below were deposited with the Institute for Fermentation, Osaka, Japan (IFO) under the accession numbers IFO 15214 and IFO 15213, respectively, on Aug. 7, 1991, and with the Fermentation Research Institute (FRI), the Agency of Industrial Science and Technology, the Ministry of International Trade and Industry, under the accession numbers FERM BP-3507 and FERM BP-3508 on Aug. 22, 1991, under the Budapest Treaty. Similarly, E. coli MM294 (DE3)/pE-L8PTH(7-84) was deposited with the IFO under the accession number IFO 15333 on Jun. 3, 1992, and with the FRI under the accession number FERM BP-3886 on Jun. 8, 1992, under the Budapest Treaty.

REFERENCE EXAMPLE 1

Synthesis of DNA Oligomers

Structural gene DNA fragments (#1-c, #2-c and #3 to #14, FIG. 3) (sequence Nos. 38, 39 and 44 to 55) and primers A and B for site-directed mutagenesis (sequence Nos. 9 and 13) were synthesized using properly protected DNA β-cyanoethylphosphoamidite as a starting material with an automatic synthesizer (Model 380A, Applied Biosystems). As a protocol for synthesis, one specified by Applied Biosystems was used. The protected DNA oligomer-resins thus synthesized were heated in 2 ml of concentrated aqueous ammonia based on 0.2 μmole of the resin at 60° C. for 6 hours. The resulting products were purified by reversed phase high performance liquid chromatography (hereinafter briefly referred to as HPLC) to obtain DNA oligomers only the 5'-terminal hydroxyl groups of which were protected by dimethoxytrityl groups. These DNA oligomers were treated with 2 ml of 80% acetic acid for 20 minutes to remove the terminal dimethoxytrityl groups, and the resulting products were purified by reverse phase HPLC and ion exchange HPLC.

REFERENCE EXAMPLE 2

Phosphorylation of DNA Oligomers

Of the DNA oligomers obtained in Reference Example 1, each of the twelve DNA oligomers #2-c and #3 to #13 (sequence Nos. 39 and 44 to 54) except for #1-c (sequence No. 38) and #14 (sequence No. 55) which were to form the 5'-termini was reacted in 25 μl of a phosphorylation reaction solution [10 μl of the DNA oligomer, 50 mM Tris-HCl (pH 7.6), 10 mM $MgCl_2$, 1 mM spermidine, 10 mM dithiothreitol (hereinafter briefly referred to as DTT), 0.1 mg/ml bovine serum albumin (hereinafter briefly referred to as BSA, 1 mM ATP, 10 units of T4 polynucleotide kinase (Takara Shuzo)] at 37° C. for 1 hour to phosphorylate the 5'-terminus. This reaction solution was treated at 65° C. for 10 minutes, followed by freezing and thawing. The resulting product was subjected to the subsequent reaction. The primers used for site-directed mutagenesis were similarly phosphorylated.

REFERENCE EXAMPLE 3

Construction of Plasmid PU-PTH Containing Human PTH Gene for Site-Directed Mutagenesis Plasmid pE-PTH (refer to European Unexamined Patent Publication No. 483509) into which the DNA of human PTH was incorporated was digested with BamHI and XbaI to obtain a 0.3-kb DNA fragment containing the DNA of human PTH and an expression vector of pET3c. Then, plasmid vector pUC118 for preparing a single strand was digested with BamHI and XbaI, and mixed with the above-mentioned DNA fragment containing the human PTH gene to ligate them to each other with T4 DNA ligase. Using the DNA thus ligated, E. coli MV1184 was transformed, and seeded onto a plate using Xgal as an indicator species. Recombinant plasmid pU-PTH in which the human PTH gene was correctly inserted into pUC118 was released to a culture medium in the form of phage particles. This single-stranded DNA was purified and used as a template for site-directed mutagenesis. E. coli MV1184 and helper phage KO7 are described in J. Vieira and J. Messing, *Methods in Enzymology*, 153, 3–11 (1987).

REFERENCE EXAMPLE 4

Production of Human PTH (1–34) OH from [Cys$^{35}$] Human PTH (1–84)

In 2.4 ml of 6M guanidine hydrochloride (hereinafter also briefly referred to as Gu-HCl )-0.2M Tris-acetate buffer (pH 8.0) was dissolved 4.76 mg of [CyS$^{35}$] human PTH (1–84) obtained in Example 2, and 0.154 mg of dithiothreitol dissolved in 0.1 ml of the above-mentioned buffer was added thereto, followed by standing at room temperature for 30 minutes. Thereto was added 1.646 mg of NTCB dissolved in 0.1 ml of the same buffer, and immediately, the pH was adjusted to 8.0, followed by reaction at room temperature for 15 minutes. After termination of the reaction, 2.5 ml of acetic acid was added, and desalting was conducted by gel filtration using a Sephadex G-25 column. The conditions of gel filtration were as follows:

Column size: 2.6×37 cm

Detecting wavelength: 280 nm

Solvent: 10% acetic acid

Flow rate: 20 ml/hour

Fractions containing [SCN-Cys$^{35}$] human PTH (1–84) were collected, and subjected to the cleavage reaction after lyophilization.

The cleavage reaction for obtaining human PTH (1–34) OH was conducted in the following manner. Namely, 200 µg of [SCN-Cys$^{35}$] human PTH (1–84) was allowed to be reacted in 200 µl of 6M Gu-HCl-0.1M borate buffer at 37° C. for 17 hours, and the same amount of glacial acetic acid was added thereto to terminate the reaction. The reaction solution was analyzed by reverse-phase HPLC (FIG. 30) under the following conditions:

Column: YMCA-303 ODS 4.6×250 mm

Column temperature: 25° C.

Elution solvent A: 0.1% TFA-99.9% distilled water Elution solvent B: 0.1% TFA-99.9% acetonitrile Elution program: 0 minute (75% A+25% B), 40 minutes (60% A +40% B), 45 minutes (20% A +80% B)

Flow rate: 0.7 ml/minute

Detecting wavelength: 230 nm

In FIG. 30, the peak at a retention time of about 35 minutes indicated by the arrow agreed with the elution time of standard human PTH (1–34) OH purchased from Peptide Laboratory (Japan). This peak fraction was taken and subjected to various protein chemical analyses. Of the cleaved fragments, fragments on the C-terminal side were eluted in fractions not adsorbed to the column, under the elution conditions of this reverse-phase HPLC.

The sample was subjected to the hydrochloric acid hydrolysis process (hydrolyzed with 5.7N hydrochloric acid in the presence of thioglycollic acid in a sealed tube under reduced pressure at 110° C. for 24 hours), and analyzed with a 6380 type amino acid analyzer (Beckman). The amino acid composition values of human PTH (1–34) OH are as shown in Table 1, and these values satisfactorily agree with the theoretical values thereof. Furthermore, it was confirmed by the following method that the carboxyl terminal amino acid Phe$^{34}$ of human PTH (1–34) OH was not racemized.

The hydrolyzed product used for amino acid analysis was used as a sample, and all amino acids contained in the hydrolyzed product were prelabeled with o-phthalaldehyde. The prelabeled sample was analyzed by reverse-phase HPLC using YMCA-303 ODS (4.6×250 mm) as a column, and an eluent was 50 mM sodium acetate-40% methanol. As a result, the Phe residues contained in the hydrolyzed product were all detected as L-Phe, and no peak of D-Phe was detected at all. Further, the molecular weight of the human PTH (1-34) OH was measured by fast atom bombardment mass spectrometry (FAB-MS). As a result, mass (m/z):(M+H)+=4116.8 was observed. This value was satisfactorily agreed with the theoretical value 4118.1 was within the range of an error.

TABLE 1

Amino Acid Composition of Human PTH(1-34)OH

|  | Experimental Value | Theoretical Value |
|---|---|---|
| Asp & Asn | 4.00 | 4 |
| Ser | 2.59 | 3 |
| Glu & Gln | 5.01 | 5 |
| Gly | 1.14 | 1 |
| Val | 2.84 | 3 |
| Met | 1.94 | 2 |
| Ile | 0.85 | 1 |
| Leu | 4.84 | 5 |
| Phe | 0.87 | 1 |
| Lys | 2.94 | 3 |
| His | 2.58 | 3 |
| Trp | 0.65 | 1 |
| Arg | 1.79 | 2 |

REFERENCE EXAMPLE 5

Production of Human PTH (1–34) NH$_2$ from [Cys$^{35}$] Human PTH (1–84)

The S-cyanylation of Cys$^{35}$ of [Cys$^{35}$] human PTH (1–84) was carried out in the following manner in accordance with the method described in *J. C. S. Chem. Comm.*, 1967, 21–22. In 3.78 ml of 7 M urea-0.1M ammonium acetate (pH 3.5) was dissolved 8.40 mg of [Cys$^{35}$] human PTH (1–84), and the solution was allowed to stand at 25° C. for 15 minutes. Then, 592 µg of 1-cyano-4-dimethylaminopyridinium fluoroborate dissolved in 0.42 ml of the above-mentioned buffer was added thereto, followed by reaction at room temperature for 15 minutes. Immediately after termination of the reaction, desalting was conducted using a Sephadex G-25 column. The column conditions were as follows:

Column size: 2.6×37 cm

Elution solvent: 10% acetic acid

Flow rate: 20 ml/hour

Detecting wavelength: 280 nm

Fractions containing [SCN-Cys$^{35}$] human PTH (1–84) were collected and lyophilized. The yield was 7.5 mg. The resulting product was used for the following cleavage reaction.

In 200 µl of 3M aqueous ammonia was dissolved 200 µg of [SCN-Cys$^{35}$] human PTH (1–84), followed by reaction at 37° C. for 10 minutes. The reaction solution was analyzed by reverse-phase HPLC under the conditions shown in Reference Example 4. As shown in FIG. 31, [SCN-Cys$^{35}$] human PTH (1–84) completely disappeared, and one peak having a shoulder at a retention time of 32 minute was observed. A main peak portion of this peak agreed with the elution position of standard human PTH (1–34) NH$_2$ obtained by solid phase synthesis. Of the cleaved fragments, fragments on the C-terminal side were eluted in flow-through fractions.

REFERENCE EXAMPLE 6

Production of Human PTH (1–34) NHC$_2$H$_5$ from [CYS$^{35}$] Human PTH (1–84)

In 500 µl of 3.1M ethylamine was dissolved 200 µg of [SCN-Cys$^{35}$] human PTH (1–84) obtained in Reference Example 4, followed by reaction at 37° C. for 20 minutes.

Then, the same amount of glacial acetic acid was added thereto to terminate the reaction. The resulting reaction solution was analyzed by reverse-phase HPLC under the conditions shown in Reference Example 3. As shown in FIG. 32, [SCN-Cys$^{35}$] human PTH (1–84) disappeared, and two peaks were mainly detected. Peaks eluted at retention times of 31 minutes and 36 minutes were named "peak 7" and "peak 8", respectively. Each fraction was taken and subjected to the protein chemical analyses.

The amino acid composition values of the peak 8 fraction which were analyzed according to the method described in Reference Example 3 are as shown in Table 2, and these values satisfactorily agree with the theoretical values of human PTH (1–34) NHC$_2$H$_5$. Furthermore, using as a sample the hydrolyzed product used for amino acid analysis, it was confirmed whether the carboxyl terminal amino acid Phe$^{34}$ of the peak 8 fraction was the D-form or the L-form.

All amino acids contained in the sample were prelabeled with o-phthalaldehyde, and then, the prelabeled sample was analyzed by reverse-phase HPLC using a YMCA-303 ODS column (4.6×250 mm). An eluent was 50 mM sodium acetate-40% methanol. As a result, the Phe residues contained in the hydrolyzed product were all detected as L-Phe, and no peak of D-Phe was detected at all. Further, the molecular weight of the resulting human PTH (1–34) NHC$_2$H$_5$ was measured by FAB-MS. As a result, mass (m/z):(M+H)+=4144.9 was observed. This value was satisfactorily agreed with the theoretical value 4143.2 was within the range of an error.

As to the peak 7 fraction, amino acid analysis was similarly conducted. The composition ratio obtained practically agreed with that of [SCN-Cys$^{35}$] human PTH (1–84). The raw material, [SCN-Cys$^{35}$] human PTH (1–84), is eluted at a retention time of about 35 minutes. This shows that peak 7 is [dehydroalanine$^{35}$] human PTH (1–84) produced by β elimination of the S-cyano group of [SCN-Cys$^{35}$] human PTH (1–84). Y. Degani, A. Patchornik, et al. report that the β elimination reaction takes place, competing with the cleavage reaction [*Biochemistry*, 13, 1–11 (1974)].

Of the cleaved fragments, fragments on the C-terminal side were eluted in flow-through fractions under the above-mentioned conditions.

TABLE 2

Amino Acid Composition of Human PTH (1-34) NHC$_2$H$_5$

|  | Experimental Value | Theoretical Value |
|---|---|---|
| Asp & Asn | 4.01 | 4 |
| Ser | 2.74 | 3 |
| Glu & Gln | 5.22 | 5 |
| Gly | 1.35 | 1 |
| Val | 2.74 | 3 |
| Met | 2.09 | 2 |
| Ile | 0.91 | 1 |
| Leu | 4.86 | 5 |
| Phe | 1.00 | 1 |
| Lys | 2.89 | 3 |
| His | 2.58 | 3 |
| Trp | 0.75 | 1 |
| Arg | 1.43 | 2 |
| Ethylamine | 1.58 | 1 |

EXAMPLE 1

Figure 4:
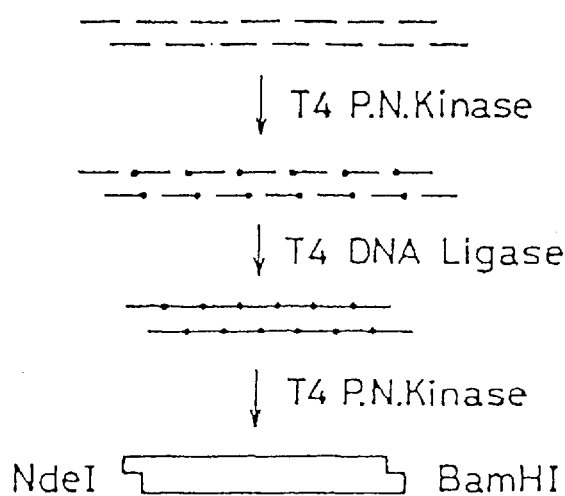
FIG. 4 is a schematic showing the production of a synthetic gene coding for a human PTH analogue by binding the respective DNA fragments shown in FIG. 3.
Figure 5:
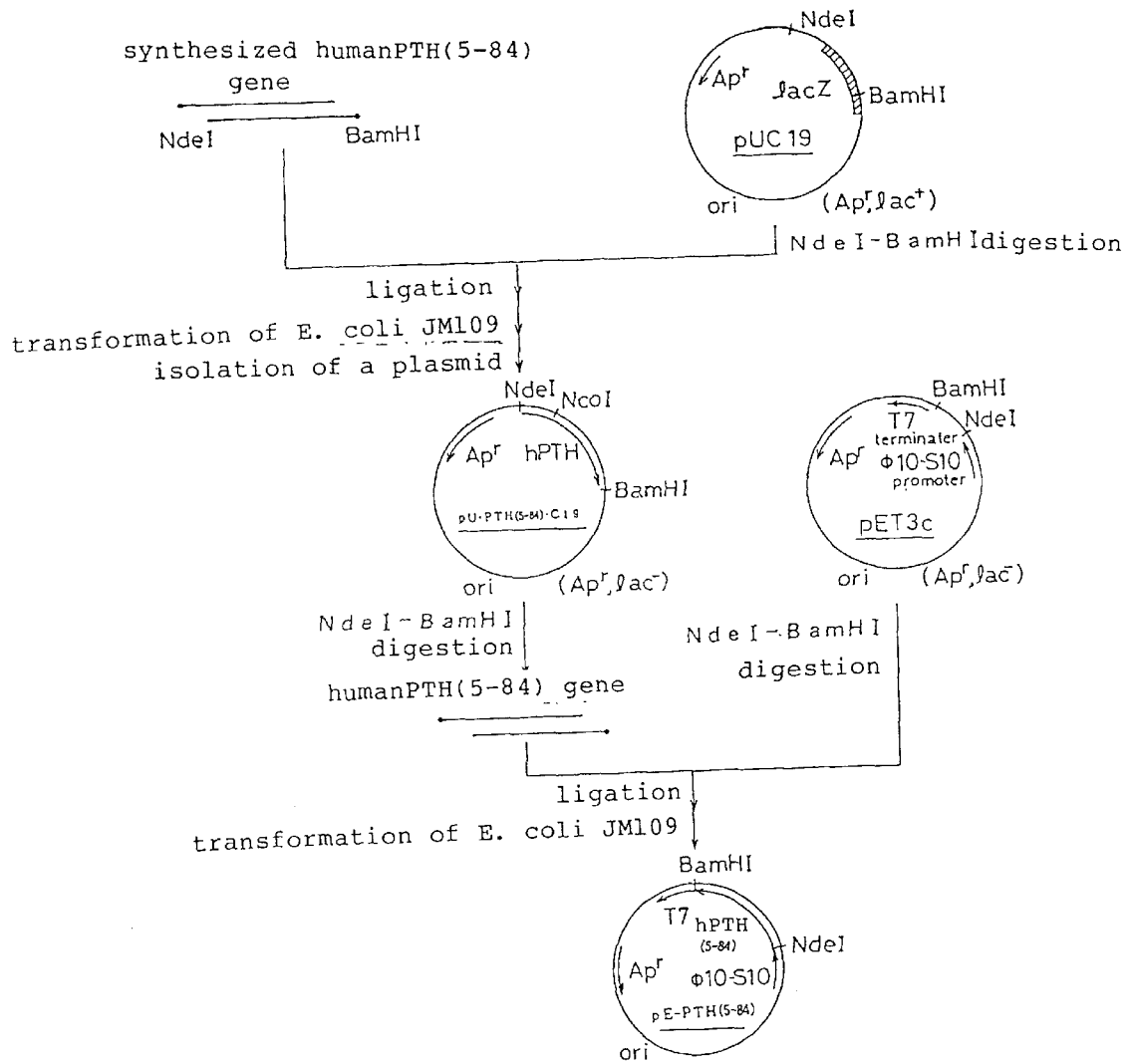
FIG. 5 shows the construction scheme for an expression plasmid which contains the synthetic gene shown in FIG. 4 is incorporated, taking human PTH (5–84) (Example 1) as an example.

Production of Gene for Coding Human PTH (5–84) and Expression Thereof (1) Ligation of DNA Fragments (refer to FIG. 4)

Series of stages for forming a double-stranded structure of a human PTH gene are as shown in FIG. 4. Referring to FIG. 4, the mark — indicates that a 5'-terminal hydroxyl group is phosphorylated. Each of the phosphorylated reaction solutions of the twelve DNA fragments [corresponding to DNA fragments #2-c and #3 to #13 (SEQ ID NOs:39 and 44 to 54)] shown in FIG. 3 were combined in an amount of 5 μl with 2 μg of DNA fragment #1-c (SEQ ID NO:38) and #14 (SEQ ID NO:55) the 5'-terminus to 70 μl. Then, 5 units of T4 DNA ligase (Takara Shuzo) was added thereto, followed by incubation at 15° C. for 20 hours.

The product thus obtained was subjected to electrophoresis on a 8% polyacrylamide gel in a buffer (pH 8.3, 100 mM Tris-HCl, 100 mM borate, 2 mM EDTA) at 125 V for 2 hours. After electrophoresis, the gel was stained with 0.6 mg/l EtBr. Gel bands containing 263-bp DNA fragments were sealed in a dialysis tube and submerged in a buffer for electrophoresis. Then, the DNA fragments were electrically eluted from the gel. A solution in this dialysis tube was treated with phenol twice, followed by recovery of an aqueous layer (an upper layer). Then, twice as much ethanol as the aqueous layer was added thereto, and the mixture was cooled to −70° C. The DNA fragments were thereafter precipitated by centrifugation. Thus, about 1 μg of the DNA fragments was obtained. After phosphorylation with T4 polynucleotide kinase (Takara Shuzo), the DNA fragments were subjected to the following experiment (2).

(2) Cloning of Human PTH (5–84) Gene (FIG. 5)

As a cloning vector, *E. coli* plasmid pBR322-derived pUC19 [J. Messing, *Gene*, 33, 103–109 (1985)] was used. pUC19 DNA was digested in 20 μl of a reaction solution [20 mM Tris-HCl (pH 7.6), 7 mM MgCl$_2$, 150 mM NaCl, 10 mM 2-mercaptoethanol, 20 units of NdeI (New England Biolabo), 15 units of BamHI (Takara Shuzo)] at 37° C. for 24 hours. Then, the resulting product was diluted 5 times with water, and treated at 65° C. for 20 minutes to inactivate the enzyme. 5 μl of this reaction solution was mixed with about 5 equivalents of the DNA fragments obtained in (1) described above to prepare 20 μl of a reaction solution containing 50 mM Tris-HCl (pH 7.5), 10 mM MgCl$_2$, 10 mM DTT, 1 mM spermidine, 0.1 mg/ml BSA and 1 mM ATP. Then, T4 DNA ligase (New England Biolabo) was allowed to be reacted with this solution at 14° C. for 15 hours to ligate the human PTH (5–84) gene to the plasmid.

Using this reaction solution, the *E. coli* JM109 strain [J. Messing, *Gene*, 33, 103–119 (1985)] was transformed according to methods known in the art. Namely, 50 μl of competent cells [D. Hanahan, *J. Mol. Biol.*, 166, 557 (1983)] stored at −70° C. was incubated at 0° C. for 15 minutes, and then 10 μl of the above-mentioned reaction solution was added thereto. The resulting solution was further incubated at 0° C. for 30 minutes, and then incubated at 42° C. for 1.5 minutes and further at 0° C. for 2 minutes. To this reaction solution was added 200 μl of LB medium (containing 10 g of bactotryptone, 5 g of a bactoyeast extract and 5 g of NaCl per 1 liter), followed by incubation at 37° C. for 1 hour. This *E. coli* was seeded onto LB agar medium (Lurla-Bertant Medium) (bacto-triptone 10 g/l, bacto-yeast extract 5 g/l, NaCl 10 g/l ) containing 50 μg/ml ampicillin, 100 μg/ml X-Gal and 0.1 mM isopropyl-β-D-thiogalactopyranoside (hereinafter referred to as IPTG), and incubated at 37° C. overnight. Of the resulting ampicillin-resistant colonies, 14β-galactosidase-deficient strains were selected and plasmid DNAs of transformed strains thereof were crudely purified by the alkali method [T. Maniatis et al., *Molecular Cloning,* (Cold Spring Harbor Laboratory) 368–369 (1982)], followed by digestion with NcoI and BamHI and further with NdeI and BamHI. The electrophoresis patterns of these digests on a 1.7% agarose gel revealed that one strain was a transformed strain into which the human PTH (5–84) gene (SEQ ID Nos:28 and 29) was correctly inserted.

(3) Construction of Plasmid for Expression of Human PTH (5-84) and Production of Transformant (FIG. 5)

(i) About 10 μg of pU-PTH(5–84)-19 obtained in the above experiment (2) was digested in a reaction solution [150 mM NaCl, 20 mM Tris-HCl (pH 7.8), 7 mM MgCl$_2$, 10 mM mercaptoethanol, 40 units of NdeI, 20 units of BamHI (Takara Shuzo)] at 37° C. for 5 hours. Then, 263-bp DNA fragments were purified by 1.7% agarose gel electrophoresis according to known methods. On the other hand, as a vector for expression, pET3c [F. W. Stadier et al., *Methods in Enzymology* 195, 60–89 (1990)] was used. pET3c DNA was digested with NdeI and BamHI in the same manner as above, and four times as much water as the resulting reaction solution was added thereto, followed by heating at 65° C. for 20 minutes to inactivate the enzyme.

Each of the 263-bp DNA and the plasmid DNA has single-stranded attachment termini produced by NdeI digestion and BamHI digestion at both ends thereof.

Both of them were mixed with each other, and the mixture was reacted with T4 DNA ligase (New England Biolabs) in the presence of 50 mM Tris-HCl (pH 7.6), 10 mM MgCl$_2$,10 mM DTT, 1 mM spermidine, 0.1 mg/ml BSA and 1 mM ATP at 14° C. for 16 hours to ligate the DNAs to each other, followed by transformation of the *E. coli* JM109 strain in the same manner as above. Then, this *E. coli* was seeded onto LB agar medium containing 50 μg/ml ampicillin, and cultivated at 37° C. for 1 day. The resulting ampicillin-resistant colony was selected. A plasmid DNA of the transformed strain was further digested by a combinations of restriction enzymes such as NdeI-BamHI, BglII-BamHI, EcoRI-NdeI or AvrII-BglII. The transformed strain correctly containing the human PTH gene was selected by its pattern of polyacrylamide electrophoresis. The plasmid for expression thus obtained was named pE-PTH (5–84), and the transformed strain was named JM109/pE-PTH (5–84).

(ii) The plasmid DNA was isolated from JM109/pE-PTH (5–84) obtained in (i), and crudely purified. Then, *E. coli* MM294(DE3) prepared by lysogenizing A phage DE3 [F. W. Studier et al., *J. Mol. Biol.,* 189, 113 (1986)] in which an RNA polymerase gene of T7 phage was incorporated into *E. coli* MM294 was transformed. First, 10 ml of LD medium was inoculated with one loopful of *E. coli* MM294(DE3), and cultivated at 37° C. with shaking to a Klett of 60 to 180. To 50 μl of this culture solution were added 10% w/v polyethylene glycol, 5% v/v dimethyl sulfoxide and 50 mM Mgcl$_2$ (pH 6.5), and a reaction solution was brought up to 100 μl with the addition of LB medium. The plasmid DNA was added thereto in an amount of 10 mg, and incubated at 4° C. for 10 minutes, followed by seeding onto LB agar medium containing 50 μg/ml ampicillin. Then, cultivation was carried out overnight at 37° C.

The plasmid DNA obtained from the resulting colony similarly with the method described above was digested with restriction enzymes, and the transformed strain containing the human PTH gene was selected by its pattern of electrophoresis. This strain was named *E. coli* MM294 (DE3)/pE-PTH (5–84).

(4) Expression of Human PTH (5–84)

Figure 13:
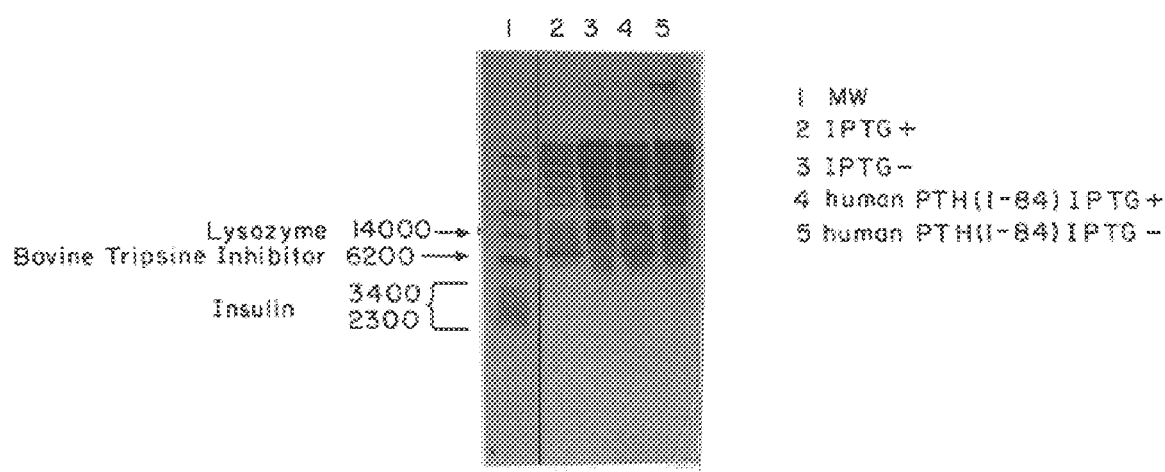
FIG. 13 shows results of SDS-PAGE after expression of a desired protein in Example 1, together with results of control experiments, wherein lanes 1 to 5 are as follows.

*E. coli* MM294(DE3)/pE-PTH (5–84) was cultivated overnight at 37° C. in LB medium containing 50 μg/ml ampicillin with shaking. To 10 ml of the same medium dispensed into a 200-ml flask, 100 μl of the resulting culture solution was added and cultivated at 37° C. to a Klett of about 170. Then, IPTG was added thereto to a concentration of 0.1 mM. After cultivation was further continued for 2 hours, 1 ml of the culture solution was centrifuged at 15,000 rpm at 4° C. for 5 minutes. The resulting cells were dissolved in 100 ml of a solution containing 0.5 M Tris-HCl (pH 6.8), 10% glycerol, 10% (w/v) sodium dodecyl sulfate (SDS), 0.1% (w/v) β-mercaptoethanol and bromophenol blue [U. K. Laemmli, *Nature,* 227, 680 (1970). After boiling for 3 minutes, the solution was subjected to 16% SDS-polyacrylamide gel electrophoresis (PAGE). After electrophoresis, the gel was stained with Coomassie Brilliant Blue. As a result, an intense band indicating a mobility approximately similar to that of a standard human PTH sample was observed (refer to FIG. 13). In the FIG. 13, Lanes 1 to 5 are as follows:

Lane 1: Molecular weight marker

Lane 2: *E. coli* strain culture solution (10 μl) carrying plasmid pE-PTH (5–84) after induction with IPTG Lane 3: *E. coli* strain culture solution (10 μl) carrying plasmid pE-PTH (5–84) without induction with IPTG Lane 4: Human PTH expression strain culture solution (10 μl) after induction with IPTG Lane 5: Human PTH expression strain culture solution without induction with IPTG.

From the quantitative comparison with the standard sample in gel staining, human PTH (5–84) was expressed in an amount of about 100 mg/l. Thus, human PTH (5–84) having the amino acid sequence shown in FIG. 6 (sequence No. 21) was obtained.

EXAMPLE 2

Production of Gene Coding for [Cys$^{35}$] Human PTH (1–84) and Expression Thereof (1) Production of Gene Coding for [Cys35] Human PTH (1–84) (FIG. 7)

First, oligonucleotide primer A, CACAATTTTTGCGCCTTAG-GTGC (SEQ ID:NO:13), was synthesized to change a codon of Val at the 35-position to a codon of Cys. Using the above-mentioned synthetic oligonucleotide (4 picomols) in which the 5' OH terminus was phosphorylated by treatment with T4 kinase and the single-stranded pU-PTH (5 μg) previously mentioned, a plasmid was obtained into which a mutation was introduced with a site-directed mutagenesis kit (oligonucleotide-directed in vitro mutagenesis system version 2, Amersham). *E. coli* MV1184 was normally transformed by this plasmid and seeded on a double YT medium (bacto-triptone 16 g/l, bacto-yeast extract 10 g/l, NaCl 5 g/1) agar plate containing 150 μg/ml ampicillin. Then, cultivation was carried out at 37° C. for 15 hours to obtain many colonies. Of these, a small amount of cells were collected from 10 colonies, and cultivated on 0.3 ml of double YT medium for about 5 hours. Thirty μl of this culture solution was mixed with 30 μl of a solution containing helper phage KO7, and the mixture was allowed to stand at 37° C. for 1 hour. Then, 3 ml of double YT medium was added thereto, followed by cultivation overnight. The resulting culture solution was subjected to centrifugation to separate a supernatant from cells. A plasmid was crudely purified from the cell by the alkali method, and a single-stranded DNA existing as a pharge particle was recovered from the supernatant.

The above-mentioned oligonucleotide primer A contains recognition sites for restriction enzyme HhaI which do not exist in the gene coding for human PTH, said gene functioning as a template.

Accordingly, when HhaI is reacted with the plasmid into which a mutation is correctly introduced, the plasmid must be cleaved at 25 sites of the HhaI sites newly generated by the mutation and HhaI sites originally existing in pUC118 to produce 260-bp fragments. The plasmid obtained from the above-mentioned 10 colonies was digested with HhaI, and analyzed by agarose gel electrophoresis. As a result, fragments of correct size were observed in 4 clones.

Further, using the single-stranded plasmids of these two clones as templates, the nucleotide sequence was analyzed with a DNA sequencer Model 373A (Applied Biosystems). As a result, the introduction of the desired mutation was confirmed (FIG. 9) (SEQ ID NO:56).

The thus-obtained plasmid containing the gene (FIG. 9) coding for [$Cys^{35}$] human PTH was named pU-C35PTH.

Figure 8:
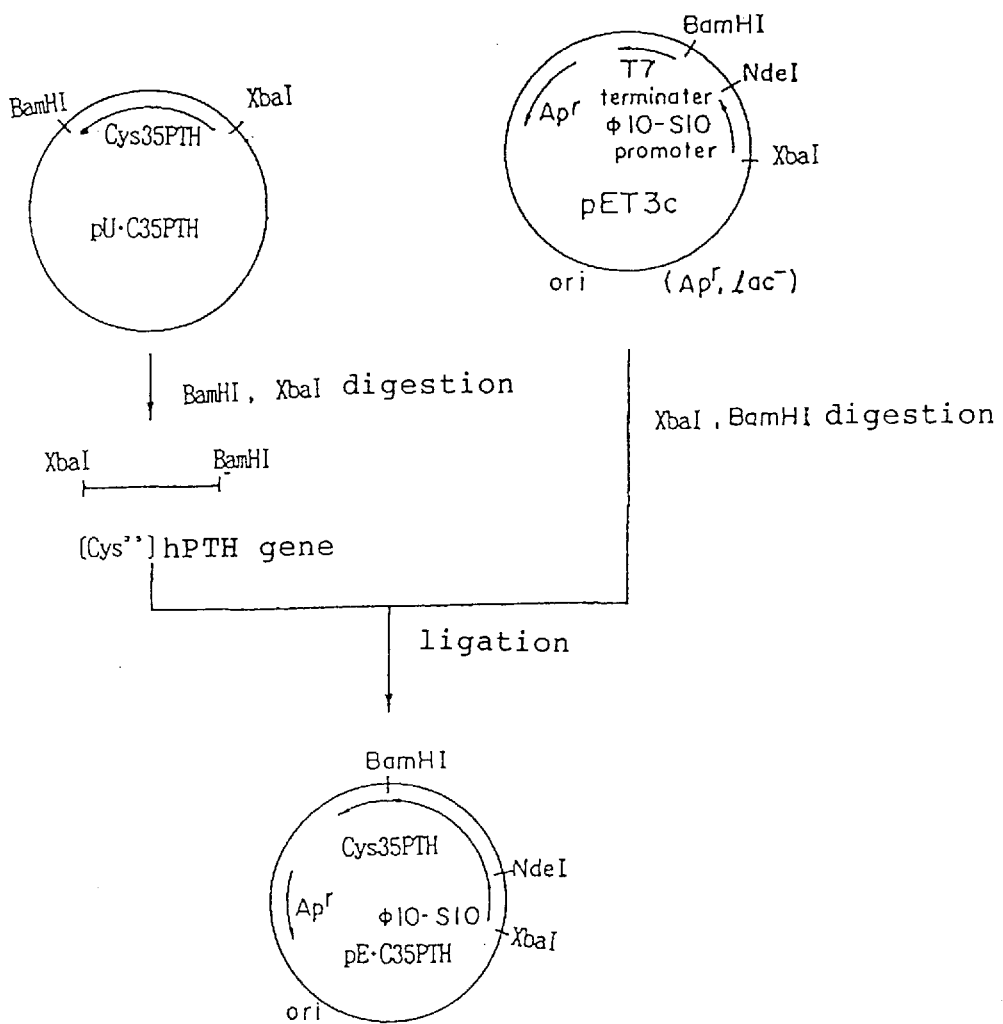
FIG. 8 is a representation shows the construction scheme for plasmid pE-C35PTH obtained in Example 2.

(2) Construction of Plasmid pE-C35PTH for Expression in *E. coli* (FIG. 8)

pU-C35PTH obtained in (1) was digested with restriction enzymes XbaI and BamHI to obtain an about 0.3-kbp fragment coding mutein [$Cys^{35}$] human PTH. After purification by agarose gel electrophoresis, this fragment was ligated with T4 ligase to expression plasmid vector pET3c [F. W. Stadier et al., *Methods in Enzymology* 195, 60–89 (1990)] preliminarily digested with restriction enzymes XbaI and BamHI. The plasmid for expression thus obtained was named pE-C35PTH.

λ Phage DE3 [F. W. Studier et al., *J. Mol. Biol.*, 189, 113–130 (1986)] in which an RNA polymerase gene of T7 phage was incorporated into the *E. coli* MM294 strain was lysogenized to prepare the *E. coli* MM294(DE3) strain. Using plasmid pE-C35PTH, *E. coli* MM294(DE3) was transformed, thereby obtaining cell MM294(DE3)/pE-C35PTH having the plasmid containing the gene coding for the mutein shown in FIG. 9.

(3) Production of [$Cys^{35}$] Human PTH (i) *E. coli* MM294(DE3)/pE-C35PTH was cultivated overnight at 37° C. in 3 ml of LB medium containing 50µg/ml ampicillin with shaking. To 10 ml of the same medium dispensed into a 200-ml flask, 100 µl of the resulting culture solution was added and cultivated at 37° C. to a Klett of about 170. Then, IPTG was added thereto to a concentration of 0.1 mM. After cultivation was further continued for 2 hours, 1 ml of the culture solution was centrifuged at 15,000 rpm at 4° C. for 5 minutes. The resulting cells were dissolved in 100 ml of a solution containing 0.5M Tris-HCl (pH 6.8), 10% glycerol, 10% (w/v) sodium dodecyl sulfate (SDS), 0.1% (w/v) β-mercaptoethanol and bromophenol blue [U. K. Laemmli, *Nature*, 227, 680 (1970)]. After boiling for 3 minutes, the solution was subjected to 16% SDS-polyacrylamide gel electrophoresis (PAGE). After electrophoresis, the gel was stained with Coomassie Brilliant Blue. As a result, an intense band indicating a mobility similar to that of a standard human PTH sample was observed (refer to FIG. 14).

Lanes 1 to 5 in FIG. 14 are as follows:

Lane 1: Human PTH (1 µg)

Lane 2: *E. coli* strain culture solution (10 µl) not carrying plasmid pE-C35PTH after induction with IPTG Lane 3: *E. coli* strain culture solution (10 µl) carrying plasmid pE-C35PTH after induction with IPTG.

Another gel was subjected to Western blotting using an human PTH antibody. As a result, the same stained pattern as with the standard human PTH was also obtained (refer to FIG. 15). The objects of respective lanes shown in FIG. 15 are the same as with FIG. 14. From the quantitative comparison with the standard sample in gel staining, [$Cys^{35}$] human PTH was expressed in an amount of about 100 mg/l.

(ii) [Cys35] human PTH accumulated in *E. coli* was purified in the following manner. Cells from 200 ml of a culture solution obtained similarly with the above-mentioned method were suspended in a buffer (5 ml) containing 8M urea, 50 mM Tris-HCl (pH 7.5), 50 mM EDTA, 20 mM 2-mercaptoethanol (hereinafter sometimes referred to as 2-ME) and 1 mM α-toluenesulfonyl fluoride, and vigorously stirred under ice cooling for about 1 hour to disrupt the cells, followed by centrifugation at 15,000 rpm at 4° C. for 20 minutes. The supernatant was recovered, and the precipitate was similarly extracted with two 3 ml portions of a buffer having the same composition twice. The extracts were combined with the supernatant, followed by two-fold dilution. The resulting solution was passed through a CM-Toyo Pearl column (10 ml) of TSK-Gel (Tosoh) equilibrated with 50 mM ammonium acetate buffer (pH 5) containing 4M urea and 10 mM 2-mercaptoethanol (2-ME) to allow a desired product to be adsorbed. The column was washed with 50 mM ammonium acetate buffer (pH 5) containing 4M urea and 10 mM 2-ME. About 10 ml of the buffer was required for washing. When absorption at 280 nm disappeared, the column was developed by a linear gradient of 50 ml of 50 mM ammonium acetate buffer (pH 5) containing 10 mM 2-ME-50 ml of 0.5M ammonium acetate buffer (pH 6) (flow rate: 10 ml/hour, volume of 1 fraction: 2 ml). Fractions 35 to 43 were collected and lyophilized. These fractions were subjected to reversed phase HPLC under the following conditions:

Column: YMC-Pack A-325 S-5 120A ODS (lX30 cm) (Y. M. C.)

Solvent: A linear gradient of 25% to 50% acetonitrile containing 0.1% trifluoroacetic acid (for 30 minutes)

Flow rate: 3 ml/minute

The peak of the desired product absorption (the retention time was 17.0 minutes) was pooled. The resulting eluate was passed through a Bio-Rad AG1X8 (acetate form) column (Bio-Rad Laboratory) and the washings were also combined therewith. Then, acetonitrile was removed by distillation, followed by lyophilization. A desired human PTH analogue was obtained in an amount of 3.6 mg as a white powder.

The following analytical results revealed that this sample was [$Cys^{35}$] human PTH of high purity.

a) Reversed phase HPLC showed a single sharp peak under the following condition (refer to FIG. 16).

Column: YMC-Pack A-303 S-5 ODS 120A (4.6×250 mm)

Eluents: Solution A [0.1% trifluoroacetic acid (hereinafter also briefly referred to as TFA)]

Solution B (acetonitrile containing 0.1% trifluoroacetic acid)

Linear gradient: 30 to 38%, B in 30 min.

b) SDS-PAGE also showed a single band of the same mobility as that of human PTH (refer to FIG. 17).

Respective lanes shown in FIG. 17 are as follows:

Lane 1: Molecular weight marker

Lane 2: Human PTH

Lane 3: [$Cys^{35}$] human PTH c) Amino acid analysis (hydrolyzed with 5.7N hydrochloric acid in the presence of thioglycolic acid in a sealed tube under reduced pressure at 110° C. for 24 hours, and values in parentheses indicate theoretical values):

Asp (10) 10.33; Thr (1) 0.91; Ser (7) 6.10; Glu (11) 11.82; Pro (3) 3.00; Gly (4) 4.44; Ala (7) 6.91; Cys (1) 1.11:

Val (7) 6.60; Met (2) 2.11; Ile (1) 1.01; Leu (10) 10.83; Phe (1) 1.10; Lys (9) 9.32; His (4) 3.75.; Arg (5) 5.21; Trp (1) 0.93

(Recovery:84.2%; for Cys, the analytical value of a hydrolysis product after oxidation with performic acid)

d) The N-terminal amino acid sequence analysis with a gas-phase sequencer Model 470A (Applied Biosystems) revealed that the sequence from Ser at the 1-position to Leu at the 15-position was correct.

Thus, the mutein having the amino acid sequence (SEQ ID NO:56) shown in FIG. 9 was obtained in which valine at the 35-position was substituted by cysteine.

EXAMPLE 3

Figure 10:
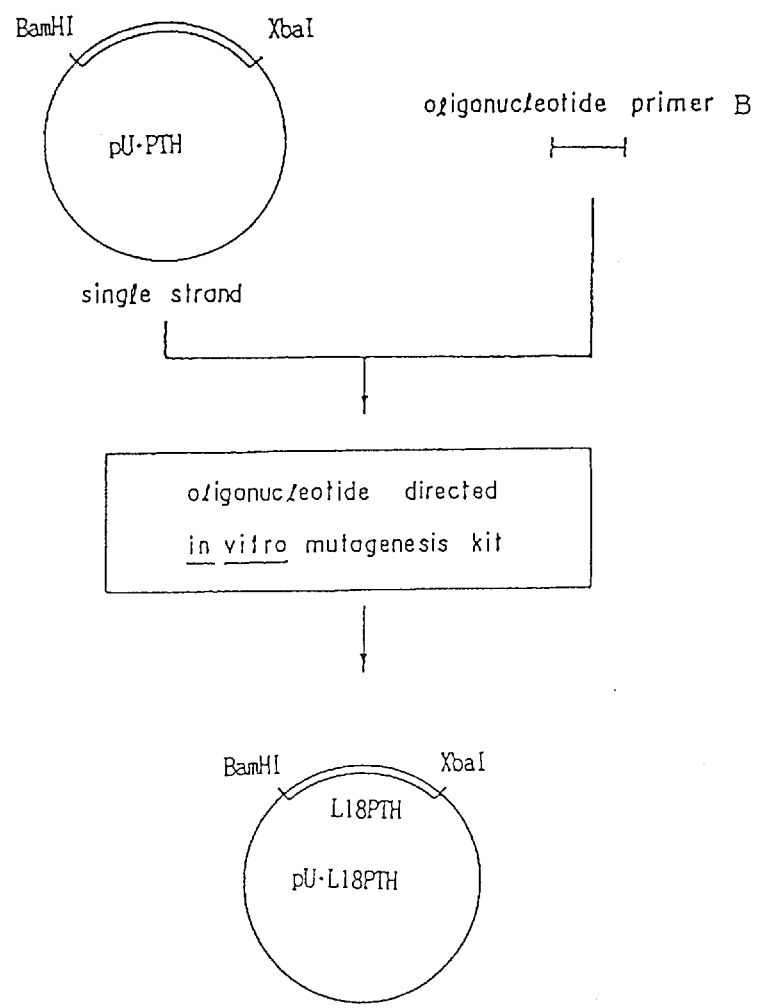
FIG. 10 is a representation showing the construction scheme for plasmid pU-L18PTH obtained in Example 3.
Figure 11:
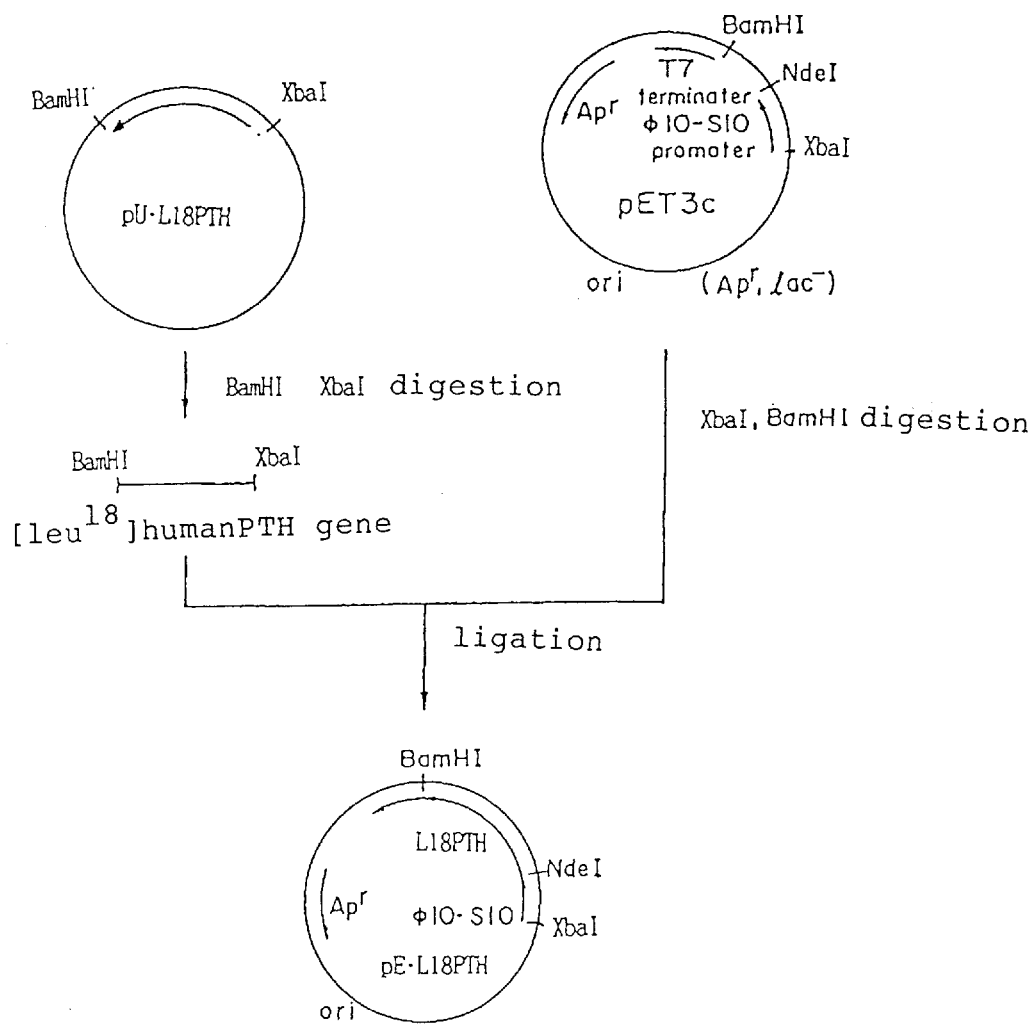
FIG. 11 is a representation showing the construction scheme for plasmid pE-L18PTH obtained in Example 3.

Production of Gene Coding for [Leu[18]] Human PTH (1–84) and Expression Thereof (1) Production of Gene Coding [Leu[18]] Human PTH (1–84) (FIG. 10)

First, oligonucleotide primer B, ACATTTGAACTCGCTGGAGG-GTGTAGAA (SEQ ID NO:9), was synthesized to change a codon of Met at the 18-position to a codon of Leu. Using the above-mentioned synthetic oligonucleotide (4 picomols) in which the 5' OH terminus was phosphorylated by treatment with T4 kinase and the single-stranded pU-PTH (5μg), a plasmid was obtained into which a mutation was introduced with the site-directed mutagenesis kit (oligonucleotide-directed in vitro mutagenesis system version 2, Amersham) described in Example 2. *E. coli* MV1184 was normally transformed by this plasmid and seeded on a double YT medium agar plate containing 150μg/ml ampicillin. Then, cultivation was carried out at 37° C. for 15 hours to obtain many colonies. Of these, a small amount of cells were collected from 5 colonies, and cultivated on 0.3 ml of double YT medium for about 5 hours. Thirty μl of this culture solution was mixed with 30μl of a solution containing helper pharge KO7, and the mixture was allowed to stand at 37° C. for 1 hour. Then, 3 ml of double YT medium was added thereto, followed by cultivation overnight. The resulting culture solution was subjected to centrifugation to separate a supernatant from cells. A plasmid was crudely purified from the cell by the alkali method, and a single-stranded DNA existing as a phage particle was recovered from the supernatant.

The above-mentioned oligonucleotide primer B contains no recognition sites for restriction enzyme NcoI which exists in the gene coding for human PTH, said gene functioning as a template.

Accordingly, when NcoI-EcoRI is reacted with the plasmid into which a mutation is correctly introduced, the plasmid must not be cleaved at the NcoI sites existing before mutation and must be cleaved only at the EcoRI sites originally existing at multi-cloning sites in pUC118 not to produce 230-bp fragments. The plasmid obtained from the above-mentioned 5 colonies was digested with NcoI-EcoRI, and analyzed by agarose gel electrophoresis. As a result, fragments of correct size were observed in 2 clones.

Further, using the single-stranded plasmids of these two clones as templates, the nucleotide sequence was analyzed. As a result, the introduction of the desired mutation was confirmed (FIG. 12) (SEQ ID NO:57).

The thus-obtained plasmid containing the gene (FIG. 9) coding for [Leu[18]] human PTH was named pU-L18PTH (FIG. 10).

(2) Construction of Plasmid pE-L18PTH for Expression in *E. coli* pU-L18PTH obtained in (1) was digested with restriction enzymes XbaI and BamHI to obtain an about 0.3-kbp fragment coding for mutein [Leu[18]] human PTH. After purification by agarose gel electrophoresis, this fragment was ligated with T4 ligase to expression plasmid vector pET3c [F. W. Stadier et al., *Methods in Enzymology* 195, 60–89 (1990)] preliminarily digested with restriction enzymes XbaI and BamHI. The plasmid for expression thus obtained was named pE-L18PTH.

λ Pharge DE3 [F. W. Studier et al., *J. Mol. Biol.*, 189, 113–130 (1986)] in which an RNA polymerase gene of T7 phage was incorporated into the *E. coli* MM294 line was lysogenized to prepare the *E. coli* MM294(DE3) line.

Using plasmid pE-L18PTH, *E. coli* MM294(DE3) was transformed, thereby obtaining cell MM294(DE3)/pE-L18PTH having the plasmid containing the gene coding for the mutein shown in FIG. 12.

(3) Production of Mutein [Leu[18]] Human PTH (i) Cell MM294(DE3)/pE-L18PTH mentioned above was cultivated overnight in 3 ml of LB medium containing 35 μg/ml ampicillin with shaking. To 50 ml of LB medium (containing 35 μg/ml ampicillin), 2.5 μl of the resulting culture solution was added and cultivated at 37° C. for 2 hours. When a Klett of about 170 is attained, IPTG was added thereto to a concentration of 0.1 mM, followed by further cultivation for 4 hours. Parts of the culture solution prior to addition of IPTG and the culture solution cultivated for 3 hours after addition thereof was subjected to centrifugation to collect cells. The resulting cells were analyzed by sodium dodecyl sulfate-polyacrylamide gel electrophoresis (SDS-PAGE) under reduced conditions. The results revealed that the expression of mutein [Leu[18]] human PTH was induced by addition of IPTG (FIG. 18).

Respective lanes shown in FIG. 18 are as follows:

Lane 1: Molecular weight marker

Lane 2: *E. coli* strain culture solution (10 μl) carrying plasmid pE-L18PTH after addition of IPTG Lane 3: *E. coli* strain culture solution (10 μl) carrying plasmid pE-L18PTH without addition of IPTG Lane 4: Human PTH expression strain culture solution (10 μl) after addition of IPTG Lane 5: Human PTH expression strain culture solution (10μl) without addition of IPTG.

The same transformant was cultivated in the same manner as with Example 2 (3), and a desired protein accumulated in the cells was similarly extracted and purified to give 5 mg of a pure product.

The following analytical results revealed that this sample was [Leu[18]] human PTH of high purity.

a) Reversed phase HPLC showed a single sharp peak under following conditions (refer to FIG. 19).

Column: YMC-Pack R-ODS-5 S-5 120A (4.6×250 mm)

Eluents: Solution A (0.1% TFA)

Solution B (acetonitrile containing 0.1% TFA)

Elution conditions: Linear gradient of 0 minute (23% acetonitrile containing 0.1% TFA) →30 minutes (38% acetonitrile containing 0.1% TFA; flow rate: 1 ml/minute)

b) SDS-PAGE also showed a single band of the same mobility as that of human PTH.

c) Amino acid analysis (hydrolyzed with 5.7N hydrochloric acid in the presence of thioglycollic acid in a sealed tube under reduced pressure at 110° C. for 24 hours, and values in parentheses indicate theoretical values):

Asp (10) 11.27; Thr (1) 0.97; Ser (7) 6.64; Glu (11) 12.0; Pro (3) 3.11; Gly (4) 3.86; Ala (7) 7.00; Val (8) 7.12; Met (1) 0.98; Ile (1) 0.98; Leu (11) 11.7; Phe (1) 1.02; Lys (9) 9.81; His (4) 3.75; Arg (5) 5.21; Trp (1) 0.93

(Recovery:83%)

d) The N-terminal amino acid sequence analysis with a gas-phase sequencer Model 470A (Applied Biosystems) revealed the sequence from Ser at the 1-position to Arg at the 20-position.

Thus, the mutein having the amino acid sequence (SEQ ID NO:57) shown in FIG. 12 was obtained in which methionine at the 18-position was substituted by leucine.

EXAMPLE 4

Production of Gene Coding for [Leu$^8$] Human PTH (1–84) and Expression Thereof (1) Production of Gene Coding for [Leu$^8$] Human PTH (1–84)

First, oligonucleotide primer TCCGAGATTCAGCTGCTGCATAA-CCTT (SEQ ID NO:6) was synthesized to change a codon of Met at the 8-position to a codon of Leu. Using the above-mentioned synthetic oligonucleotide (4 picomols) in which the 5' OH terminus was phosphorylated by treatment with T4 kinase and the single-stranded pU-PTH (5 μg), a plasmid was obtained into which a mutation was introduced with the site-directed mutagenesis kit (oligonucleotide-directed in vitro mutagenesis system version 2, Amersham) described in Example 2. E. coli MV1184 was transformed by this plasmid and seeded on a double YT medium agar plate containing 150 μg/ml ampicillin. Then, cultivation was carried out at 37° C. for 15 hours to obtain many colonies. Of these, a small amount of cells were collected from 5 colonies, and cultivated in 0.3 ml of double YT medium for about 5 hours. Thirty μl of this culture solution was mixed with 30 μl of a solution containing helper phage KO7, and the mixture was allowed to stand at 37° C. for 1 hour. Then, 3 ml of double YT medium was added thereto, followed by cultivation overnight. The resulting culture solution was subjected to centrifugation to separate a supernatant from cells. A plasmid was crudely purified from the cell by the alkali method, and a single-stranded DNA existing as a phage particle was recovered from the supernatant.

A recognition site for restriction enzyme PvuII which does not exist in the gene coding for human PTH is inserted into the above-mentioned oligonucleotide primer, said gene functioning as a template.

Accordingly, the plasmid into which a mutation is correctly introduced can be selected from the patterns of agarose gel electrophoresis after digestion with PvuII. Here, 3 clones indicated a correct digestion pattern.

Further, using the single-stranded plasmids of these two clones as templates, the nucleotide sequence was analyzed. As a result, the introduction of the desired mutation was confirmed. The thus-obtained plasmid containing the gene coding for [Leu$^8$] human PTH was named pU-L8PTH.

(2) Construction of Plasmid pE-L8PTH for Expression in E. coli pU-L8PTH obtained in (1) was digested with restriction enzymes XbaI and BamHI to obtain an about 0.3- kbp fragment coding for mutein [Leu$^8$] human PTH. After purification by agarose gel electrophoresis, this fragment was ligated with T4 ligase to expression plasmid vector pET3c [F. W. Stadier et al., *Methods in Enzymology* 195, 60–89 (1990)] preliminarily digested with restriction enzymes XbaI and BamHI. The plasmid for expression thus obtained was named pE-L8PTH.

λ Phage DE3 [F. W. Studier et al., *J. Mol. Biol.*, 189, 113–130 (1986)] in which an RNA polymerase gene of T7 phage was incorporated into the E. coli MM294 strain was lysogenized to prepare the E. coli MM294(DE3) strain.

Using plasmid pE-L8PTH, E. coli MM294(DE3) was transformed, thereby obtaining cell MM294(DE3)/pE-L8PTH having the plasmid containing the gene coding for the mutein in which methionine at the 8-position was substituted by leucine.

(3) Production of Mutein [Leu$^8$] Human PTH

Cell MM294(DE3)/pE-L8PTH mentioned above was cultivated overnight in 3 ml of LB medium containing 35 μg/ml ampicillin with shaking. To 50 ml of LB medium (containing 35 μg/ml ampicillin), 2.5 μl of the resulting culture solution was added and cultivated at 37° C. for 2 hours. When a Klett of about 170 is attained, IPTG was added thereto to a concentration of 0.1 mM, followed by further cultivation for 4 hours. Parts of the culture solution prior to addition of IPTG and the culture solution cultivated for 3 hours after addition thereof was subjected to centrifugation to collect cells. The resulting cells were analyzed by sodium dodecyl sulfate-polyacrylamide gel electrophoresis (SDS-PAGE) under reduced conditions. The results revealed that the expression of mutein [Leu$^8$] human PTH was induced by addition of IPTG.

The same transformant was cultivated in the same manner as with Example 2 (3), and a desired protein accumulated in the cells was similarly extracted and purified to give 4.7 mg of a pure product.

The following analytical results revealed that this sample was [Leu$^8$] human PTH of high purity.

a) Reversed phase HPLC showed a single sharp peak (refer to FIG. 20) under following conditions.

Column: YMC-Pack R-ODS-5 S-5 120A (4.6×250 mm)

Eluents: Solution A (0.1% TFA)
Solution B (acetonitrile containing 0.1% TFA)

Elution conditions: Linear gradient of 0 minute (25% acetonitrile containing 0.1% TFA) →30 minutes (40% acetonitrile containing 0.1% TFA; flow rate: 1 ml/minute)

b) SDS-PAGE also showed a single band of the same mobility as that of human PTH.

c) Amino acid analysis (hydrolyzed with 5.7N hydrochloric acid in the presence of thioglycolic acid in a sealed tube under reduced pressure at 110° C. for 24 hours, and values in parentheses indicate theoretical values):

Asp (10) 10.09; Thr (1) 0.89; Ser (7) 6.45; Glu (11) 11.14; Pro (3) 3.08; Gly (4) 4.03; Ala (7) 7.00; Val (8) 7.57; Met (1) 1.05; Ile (1) 1.01; Leu (11) 11.32; Phe (1) 0.98; Lys (9) 8.62; His (4) 3.72; Arg (5) 4.80; Trp (1) 0.64 (Recovery: 79.2%)

d) The N-terminal amino acid sequence analysis with a gas-phase sequencer Model 470A (Applied Biosystems) revealed the sequence from Ser at the 1-position to Leu at the 15-position.

Thus, the mutein having the amino acid sequence (sequence No. 58) shown in FIG. 21 was obtained in which methionine at the 8-position was substituted by leucine.

EXAMPLE 5

Production of [Leu$^8$] Human PTH (7–84) Gene and Expression Thereof (1) Construction of Expression Plasmid for [Leu$^8$] Human PTH (7–84) and Production of Transformant (FIG. 22)

(i) As a plasmid for expression, pE-PTH (European Patent Application No. 483509) in which the N-terminus of the human PTH gene was modified was used. In 15 μl of a reaction solution [10 mM Tris-HCl (pH 7.5), 10 mM MgCl$_2$, 1 mM DTT, 80 mM NaCl and 15 units of restriction enzyme NcoI (Takara Shuzo)], 2 μg of pE-PTH DNA was reacted at 37° C. for 2 hours. Then, NaCl was added to a concentration of 150 mM, and 20 units of NdeI (New England Biolabs) was further added thereto, followed by reaction at 37° C. for 2 hours. Subsequently, the reaction product was treated at 65° C. for 20 minutes to inactivate the enzyme, and then, diluted 10 times with water. On the other hand, a gene coding the N-terminal portion as well as a complemental strand was synthesized using a DNA synthesizer 380A (Applied Biosystems), said gene consisting of an initiation codon ATG corresponding to the NdeI binding site, a codon for Leu$^7$ subsequent thereto, a codon of Leu substituted for Met$^8$ and codons of His$^9$ to Ser$^{17}$ corresponding to the NcoI binding site. The 5'-termini of these two fragments were each phosphorylated. Referring to FIG. 22, the mark — indicates that a 5'-terminal hydroxyl group is phosphorylated.

5'-TATGTTACTCCATAACCTTGGCAAACATTTGA-ACTC-3' (SEQ ID NO: 59)

5'-CATGGAGTTCAAATGTTTGCCAAGGTTATGGA-GTAACA-3' (SEQ ID NO:60)

Both of them were mixed with each other, and the mixture was reacted with T4 DNA ligase (New England Biolabo) in the presence of 50 mM Tris-HCl (pH 7.6), 10 mM MgCl$_2$, 10 mM DTT, 1 mM spermidine, 0.1 mg/ml BSA and 1 mM ATP at 14° C. for 16 hours to ligate the DNAs to each other, followed by transformation of the *E. coli* JM109 strain in the same manner as above. Then, this *E. coli* was seeded onto LB medium containing 50 μg/ml ampicillin, and cultivated at 37° C. for 1 day. The resulting ampicillin-resistant colony was selected. A plasmid DNA of the transformed strain was further digested with restriction enzymes NdeI-BamHI. The transformed strain correctly containing the human PTH gene was selected by its pattern of polyacrylamide electrophoresis. The plasmid for expression thus obtained was named pE-L8PTH (7–84), and the transformed strain was named *E. coli* JM109/pE-L8PTH (7–84).

(ii) A plasmid DNA was isolated from JM109/pE-L8PTH (7–84) obtained in (i). Using this plasmid DNA, *E. coli* MM294(DE3) was transformed similarly with Example 1 (3) (ii) to obtain *E. coli* MM294(DE3)/pE-L8PTH (7–84).

(2) Production of [Leu$^8$] Human PTH (7–84)

*E. coli* MM294(DE3)/pE-L8PTH (7–84) obtained in (1) was cultivated similarly with Example 2 (3), and a desired protein (FIG. 23) accumulated in the cells was extracted and purified to give 5.3 mg of a product. The amino acid analysis and the N-terminal amino acid sequence analysis revealed that Met is further added to the N-terminal Leu of the above protein, namely that the protein is [Met$^6$, Leu$^8$] human PTH (6–84).

The following analytical results revealed that this sample was [Leu$^8$] human PTH (7–84) of high purity (with the proviso that a Met residue was added to the N-terminus).a) Reversed phase HPLC showed a single sharp peak under following conditions (refer to FIG. 24).

Column: YMC-Pack R-ODS-5 S-5 120A (4.6×250 mm)

Eluents: Solution A (0.1% TFA)

Solution B (acetonitrile containing 0.1% TFA)

Elution conditions: Linear gradient of 0 minute (23% acetonitrile containing 0.1% TFA) →30 minutes (38% acetonitrile containing 0.1% TFA; flow rate: 1 ml/minute)

b) SDS-PAGE also showed a single band.

c) Amino acid analysis (hydrolyzed with 5.7N hydrochloric acid in the presence of thioglycolic acid in a sealed tube under reduced pressure at 110° C. for 24 hours, and values in parentheses indicate theoretical values):

Asp (10) 10.1; Thr (1) 0.91; Ser (5) 4.49; Glu (9) 9.46; Pro (3) 2.96; Gly (4) 3.67; Ala (7) 7.00; Val (7) 6.35; Met (1) 1.94; Leu (11) 11.41; Phe (1) 1.07; Lys (9) 8.62; His (4) 3.61; Arg (5) 4.89; Trp (1) 0.91

(Recovery: 79.7%)

d) The N-terminal amino acid sequence analysis with a gas-phase sequencer Model 470A (Applied Biosystems) revealed that the sequence from Ser at the 1-position and Leu at the 2-position to the twentieth residue was correct.

Thus, the mutein having the amino acid sequence (sequence No. 61) shown in FIG. 25, human PTH (7–84) in which methionine at the 8-position was substituted by leucine, was obtained.

EXAMPLE 6

Production of [Leu$^{8,18}$] Human PTH (1–84) and Expression Thereof (1) Production of Gene Coding [Leu$^{8,18}$] Human PTH (1–84) (FIG. 26)

Using plasmid pE-L8PTH for expression of [Leu$^8$] human PTH obtained in Example 4, single-stranded plasmid pU-L8PTH containing a [Leu$^8$] human PTH gene for conducting site-directed mutagenesis was constructed by a procedure similar to that for obtaining pU-PTH described in Reference Example 3. Using this DNA, plasmid pU-L8, 18PTH was obtained which contains a gene coding for [Leu$^{8,18}$] human PTH in which the 18-position Met codon was mutated to a Leu codon by a method similar to that described in Example 3.

(2) Construction of Plasmid pE-L8,18PTH for Expression in *E. coli* (FIG. 27)

Using pU-L8,18PTH obtained in (1), plasmid pE-L8, 18PTH for expression was obtained in the same manner as with Example 3 (2). Then, *E. coli* MM294(DE3) was transformed using this plasmid, thereby obtaining cell MM294(DE3)/pE-L8,18PTH which has a plasmid containing a gene coding for the mutein shown in FIG. 28 (SEQ ID NO:62). (3) Production of [Leu$^{8,18}$] Human PTH Transformant MM294(DE3)/pE-L$^{8,18}$PTH obtained in (2) was cultivated in the same manner as with Example 2 (3), and a desired protein accumulated in the cells was similarly extracted and purified to give 5 mg of pure [Leu$^{8,18}$] human PTH (1–84).

The following analytical results revealed that this sample was [Leu$^{8,18}$] human PTH of high purity.

a) Reverse phase HPLC showed a single sharp peak (refer to FIG. 29) under following conditions.

Column: YMC-Pack R-ODS-5 S-5 120A (4.6×250 mm)

Eluents: Solution A (0.1% TFA)

Solution B (acetonitrile containing 0.1% TFA)

Elution conditions: Linear gradient of 0 minute (25% acetonitrile containing 0.1% TFA) →30 minutes (40% acetonitrile containing 0.1% TFA; flow rate: 1 ml/minute)

b) SDS-PAGE also showed a single band of the same mobility as that of human PTH.

c) Amino acid analysis (hydrolyzed with 5.7N hydrochloric acid in the presence of thioglycollic acid in a sealed tube under reduced pressure at 110° C. for 24 hours, and values in parentheses indicate theoretical values):

Asp (10) 10.38; Thr (1) 0.88; Ser (7) 6.37; Glu (11) 11.82; Pro (3) 2.88; Gly (4) 3.79; Ala (7) 7.00; Val (8) 7.47; Ile (1) 0.98; Leu (12) 13.00; Phe (1) 1.10; Lys (9) 8.93; His (4) 3.74; Arg (5) 5.09; Trp (1) 0.96

(Recovery:80 %)

d) The N-terminal amino acid sequence analysis with a gas-phase sequencer Model 470A (Applied Biosystems)

revealed that the sequence from Ser at the 1-position to Arg at the 20-position was correct.

Thus, the mutein having the amino acid sequence (SEQ ID NO:62) shown in FIG. 28 was obtained in which methionine residues at the 8- and the 18-positions were substituted by leucine.

EXPERIMENTAL EXAMPLE

The biological activity of human PTH muteins obtained in Examples 2 to 6 and natural type human PTH were evaluated by a modification of the method reported by Shigeno et al. [*The Journal of Biological Chemistry* 263. 18369–18377 (1988)]. A culture solution (Hank's solution containing 20 mM N-2-hydroxyethylpiperazine-N'-2-ethanesulfonic acid (HEPES), 0.1% bovine serum albumin (BSA) and 0.5 mM isobutylmethylxanthine) containing 0.01, 0.1, 1, 10 or 100 nM analogue was added in an amount of 100 µl to mouse cranial bone-derived osteoblast-like cell strain MC3T3-EI cultivated on a 96-well multiplate (Nunclon, Nunc), followed by reaction at room temperature for 30 minutes. After addition of 100 µl of 0.2N hydrochloric acid, the mixture was immersed in boiling water for 2.5 minutes, and cyclic adenosine monophosphate (cAMP) produced by a human PTH receptor was extracted from the cells. The total cAMP in the culture solution and the cells was assayed using a commercial radioimmunoassay kit (cyclic AMP [$^{125}$I] kit "Du Pont-Daiichil", Daiichi Kagaku Yakuhin). An increase in cAMP production depending on the concentration of the human PTH mutein added was always observed. The specific activity of the muteins on the natural type human PTH is as follows:

| Human PTH | Specific Activity |
|---|---|
| Human PTH | 1.0 |
| [Leu$^8$] human PTH | 1.0 |
| [Leu$^{18}$] human PTH | 0.2 |
| [Leu$^{8,18}$] human PTH | 0.3 |
| [Cys$^{35}$] human PTH | 0.6 |

What is claimed is:

1. A human parathyroid hormone (1–84) mutein comprising substitution of a cysteine residue for one amino acid residue within the region of amino acid residue number 34 to 47 in the amino acid sequence of human parathyroid hormone (1–84), wherein cleavage of the mutein at the cysteine residue produces an human parathyroid hormone fragment having parathyroid hormone activity.

2. The human parathyroid hormone (1–84) mutein claimed in claim 1, which is human parathyroid hormone (1–84).

3. A recombinant DNA having a nucleotide sequence coding for the human parathyroid hormone (1–84) mutein claimed in claim 1.

4. A vector containing the recombinant DNA claimed in claim 3.

5. A vector in which the recombinant DNA claimed in claim 3 is inserted into a region controlled by an *Escherichia coli* T7 promoter.

6. A host cell which is transformed by the recombinant DNA claimed in claim 3.

7. A process for producing a human parathyroid hormone (1–84) mutein which comprises cultivating the transformed host cell claimed in claim 6 in a culture medium under conditions suitable for expression of the mutein.

* * * * *

SEQUENCE LISTING ( 1 ) GENERAL INFORMATION:

( i i i ) NUMBER OF SEQUENCES: 62

( 2 ) INFORMATION FOR SEQ ID NO:1:

( i ) SEQUENCE CHARACTERISTICS:
        ( A ) LENGTH: 78 amino acids
        ( B ) TYPE: amino acid
        ( D ) TOPOLOGY: linear ( i i ) MOLECULE TYPE: protein ( i x ) FEATURE:
        ( A ) NAME/KEY: mutation
        ( B ) LOCATION: 2 Xaa=Leu, Ile, Val, Phe, Tyr, Trp or Met,
            12 Xaa=Leu, Ile, Val, Phe, Tyr, Trp or Met,
            28 Xaa=Cys or Phe, 29 Xaa=Cys or Val,
            31 Xaa=Cys or Leu, 33 Xaa=Cys or Ala,
            35 Xaa=Cys or Leu, 37 Xaa=Cys or Pro, 38 Xaa=Cys or Arg
        ( C ) IDENTIFICATION METHOD: E ( x i ) SEQUENCE DESCRIPTION: SEQ ID NO:1:

```
Leu  Xaa  His  Asn  Leu  Gly  Lys  His  Leu  Asn  Ser  Xaa  Glu  Arg  Val  Glu
 1                    5                        10                       15

Trp  Leu  Arg  Lys  Lys  Leu  Gln  Asp  Val  His  Asn  Xaa  Xaa  Ala  Xaa  Gly
               20                        25                       30

Xaa  Pro  Xaa  Ala  Xaa  Xaa  Asp  Ala  Gly  Ser  Gln  Arg  Pro  Arg  Lys  Lys
          35                        40                       45

Glu  Asp  Asn  Val  Leu  Val  Glu  Ser  His  Glu  Lys  Ser  Leu  Gly  Glu  Ala
     50                        55                       60

Asp  Lys  Ala  Asp  Val  Asn  Val  Leu  Thr  Lys  Ala  Lys  Ser  Gln
 65                       70                       75
```

( 2 ) INFORMATION FOR SEQ ID NO:2:

( i ) SEQUENCE CHARACTERISTICS:
        ( A ) LENGTH: 79 amino acids
        ( B ) TYPE: amino acid
        ( D ) TOPOLOGY: linear ( i i ) MOLECULE TYPE: protein (  i x  ) FEATURE:
  ( A ) NAME/KEY: mutation
  ( B ) LOCATION: 3 Xaa=Leu, Ile, Val, Phe, Tyr, Trp or Met,
    13 Xaa=Leu, Ile, Val, Phe, Tyr, Trp or Met,
    29 Xaa=Cys or Phe, 30 Xaa=Cys or Val,
    32 Xaa=Cys or Leu, 34 Xaa=Cys or Ala,
    36 Xaa=Cys or Leu, 38 Xaa=Cys or Pro, 39 Xaa=Cys or Arg
  ( C ) IDENTIFICATION METHOD: E ( x i ) SEQUENCE DESCRIPTION: SEQ ID NO:2:

| Gln | Leu | Xaa | His | Asn | Leu | Gly | Lys | His | Leu | Asn | Ser | Xaa | Glu | Arg | Val |
|---|---|---|---|---|---|---|---|---|---|---|---|---|---|---|---|
| 1 | | | | 5 | | | | | 10 | | | | | 15 | |
| Glu | Trp | Leu | Arg | Lys | Lys | Leu | Gln | Asp | Val | His | Asn | Xaa | Xaa | Ala | Xaa |
| | | | 20 | | | | | 25 | | | | | 30 | | |
| Gly | Xaa | Pro | Xaa | Ala | Xaa | Xaa | Asp | Ala | Gly | Ser | Gln | Arg | Pro | Arg | Lys |
| | | 35 | | | | | 40 | | | | | 45 | | | |
| Lys | Glu | Asp | Asn | Val | Leu | Val | Glu | Ser | His | Glu | Lys | Ser | Leu | Gly | Glu |
| | 50 | | | | | 55 | | | | | 60 | | | | |
| Ala | Asp | Lys | Ala | Asp | Val | Asn | Val | Leu | Thr | Lys | Ala | Lys | Ser | Gln | |
| 65 | | | | | 70 | | | | | 75 | | | | | |

( 2 ) INFORMATION FOR SEQ ID NO:3:

( i ) SEQUENCE CHARACTERISTICS:
    ( A ) LENGTH: 80 amino acids
    ( B ) TYPE: amino acid
    ( D ) TOPOLOGY: linear ( i i ) MOLECULE TYPE: protein ( i x ) FEATURE:
    ( A ) NAME/KEY: mutation
    ( B ) LOCATION: 4 Xaa=Leu, Ile, Val, Phe, Tyr, Trp or Met,
      14 Xaa=Leu, Ile, Val, Phe, Tyr, Trp or Met,
      30 Xaa=Cys or Phe, 31 Xaa=Cys or Val,
      33 Xaa=Cys or Leu, 35 Xaa=Cys or Ala,
      37 Xaa=Cys or Leu, 39 Xaa=Cys or Pro, 40 Xaa=Cys or Arg
    ( C ) IDENTIFICATION METHOD: E ( x i ) SEQUENCE DESCRIPTION: SEQ ID NO:3:

| Ile | Gln | Leu | Xaa | His | Asn | Leu | Gly | Lys | His | Leu | Asn | Ser | Xaa | Glu | Arg |
|---|---|---|---|---|---|---|---|---|---|---|---|---|---|---|---|
| 1 | | | | 5 | | | | | 10 | | | | | 15 | |
| Val | Glu | Trp | Leu | Arg | Lys | Lys | Leu | Gln | Asp | Val | His | Asn | Xaa | Xaa | Ala |
| | | | 20 | | | | | 25 | | | | | 30 | | |
| Xaa | Gly | Xaa | Pro | Xaa | Ala | Xaa | Xaa | Asp | Ala | Gly | Ser | Gln | Arg | Pro | Arg |
| | | 35 | | | | | 40 | | | | | 45 | | | |
| Lys | Lys | Glu | Asp | Asn | Val | Leu | Val | Glu | Ser | His | Glu | Lys | Ser | Leu | Gly |
| | 50 | | | | | 55 | | | | | 60 | | | | |
| Glu | Ala | Asp | Lys | Ala | Asp | Val | Asn | Val | Leu | Thr | Lys | Ala | Lys | Ser | Gln |
| 65 | | | | | 70 | | | | | 75 | | | | | 80 |

( 2 ) INFORMATION FOR SEQ ID NO:4:

( i ) SEQUENCE CHARACTERISTICS:
    ( A ) LENGTH: 81 amino acids
    ( B ) TYPE: amino acid
    ( D ) TOPOLOGY: linear ( i i ) MOLECULE TYPE: protein ( i x ) FEATURE:
    ( A ) NAME/KEY: mutation
    ( B ) LOCATION: 5 Xaa=Leu, Ile, Val, Phe, Tyr, Trp or Met,
      15 Xaa=Leu, Ile, Val, Phe, Tyr, Trp or Met,
      31 Xaa=Cys or Phe, 32 Xaa=Cys or Val,
      34 Xaa=Cys or Leu, 36 Xaa=Cys or Ala,
      38 Xaa=Cys or Leu, 40 Xaa=Cys or Pro, 41 Xaa=Cys or Arg ( C ) IDENTIFICATION METHOD: E ( x i ) SEQUENCE DESCRIPTION: SEQ ID NO:4:

| Glu | Ile | Gln | Leu | Xaa | His | Asn | Leu | Gly | Lys | His | Leu | Asn | Ser | Xaa | Glu |
|---|---|---|---|---|---|---|---|---|---|---|---|---|---|---|---|
| 1 | | | | 5 | | | | | 10 | | | | | 15 | |

| Arg | Val | Glu | Trp | Leu | Arg | Lys | Lys | Leu | Gln | Asp | Val | His | Asn | Xaa | Xaa |
|---|---|---|---|---|---|---|---|---|---|---|---|---|---|---|---|
| | | | 20 | | | | | 25 | | | | | 30 | | |

| Ala | Xaa | Gly | Xaa | Pro | Xaa | Ala | Xaa | Xaa | Asp | Ala | Gly | Ser | Gln | Arg | Pro |
|---|---|---|---|---|---|---|---|---|---|---|---|---|---|---|---|
| | | 35 | | | | | 40 | | | | | 45 | | | |

| Arg | Lys | Lys | Glu | Asp | Asn | Val | Leu | Val | Glu | Ser | His | Glu | Lys | Ser | Leu |
|---|---|---|---|---|---|---|---|---|---|---|---|---|---|---|---|
| | 50 | | | | | 55 | | | | | 60 | | | | |

| Gly | Glu | Ala | Asp | Lys | Ala | Asp | Val | Asn | Val | Leu | Thr | Lys | Ala | Lys | Ser |
|---|---|---|---|---|---|---|---|---|---|---|---|---|---|---|---|
| 65 | | | | | 70 | | | | | 75 | | | | | 80 |

Gln ( 2 ) INFORMATION FOR SEQ ID NO:5:

( i ) SEQUENCE CHARACTERISTICS:
      ( A ) LENGTH: 84 amino acids
      ( B ) TYPE: amino acid
      ( D ) TOPOLOGY: linear ( i i ) MOLECULE TYPE: protein ( i x ) FEATURE:
      ( A ) NAME/KEY: mutation
      ( B ) LOCATION: 8 Xaa=Leu, Ile, Val, Phe, Tyr, Trp or Met,
            18 Xaa=Leu, Ile, Val, Phe, Tyr, Trp or Met,
            34 Xaa=Cys or Phe, 35 Xaa=Cys or Val,
            37 Xaa=Cys or Leu, 39 Xaa=Cys or Ala,
            41 Xaa=Cys or Leu, 43 Xaa=Cys or Pro, 44 Xaa=Cys or Arg
      ( C ) IDENTIFICATION METHOD: E ( x i ) SEQUENCE DESCRIPTION: SEQ ID NO:5:

| Ser | Val | Ser | Glu | Ile | Gln | Leu | Xaa | His | Asn | Leu | Gly | Lys | His | Leu | Asn |
|---|---|---|---|---|---|---|---|---|---|---|---|---|---|---|---|
| 1 | | | | 5 | | | | | 10 | | | | | 15 | |

| Ser | Xaa | Glu | Arg | Val | Glu | Trp | Leu | Arg | Lys | Lys | Leu | Gln | Asp | Val | His |
|---|---|---|---|---|---|---|---|---|---|---|---|---|---|---|---|
| | | | 20 | | | | | 25 | | | | | 30 | | |

| Asn | Xaa | Xaa | Ala | Xaa | Gly | Xaa | Pro | Xaa | Ala | Xaa | Xaa | Asp | Ala | Gly | Ser |
|---|---|---|---|---|---|---|---|---|---|---|---|---|---|---|---|
| | | 35 | | | | | 40 | | | | | 45 | | | |

| Gln | Arg | Pro | Arg | Lys | Lys | Glu | Asp | Asn | Val | Leu | Val | Glu | Ser | His | Glu |
|---|---|---|---|---|---|---|---|---|---|---|---|---|---|---|---|
| | 50 | | | | | 55 | | | | | 60 | | | | |

| Lys | Ser | Leu | Gly | Glu | Ala | Asp | Lys | Ala | Asp | Val | Asn | Val | Leu | Thr | Lys |
|---|---|---|---|---|---|---|---|---|---|---|---|---|---|---|---|
| 65 | | | | | 70 | | | | | 75 | | | | | 80 |

Ala Lys Ser Gln ( 2 ) INFORMATION FOR SEQ ID NO:6:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: other nucleic acid, synthetic DNA, primer ( i v ) ANTI-SENSE: NO ( x i ) SEQUENCE DESCRIPTION: SEQ ID NO:6:

TCCGAGATTC AGCTGCTGCA TAACCTT    27

( 2 ) INFORMATION FOR SEQ ID NO:7:

( i ) SEQUENCE CHARACTERISTICS:

(A) LENGTH: 27 base pairs
(B) TYPE: nucleic acid
(C) STRANDEDNESS: single
(D) TOPOLOGY: linear (ii) MOLECULE TYPE: other nucleic acid, synthetic DNA, primer (iv) ANTI-SENSE: NO (xi) SEQUENCE DESCRIPTION: SEQ ID NO:7:

TCCGAGATTC AGTTAATCCA TAACCTT     27

(2) INFORMATION FOR SEQ ID NO:8:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: other nucleic acid, synthetic DNA, primer (iv) ANTI-SENSE: NO (xi) SEQUENCE DESCRIPTION: SEQ ID NO:8:

TCCGAGATTC AGTTAACGCA TAACCTT     27

(2) INFORMATION FOR SEQ ID NO:9:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: other nucleic acid, synthetic DNA, primer (iv) ANTI-SENSE: NO (xi) SEQUENCE DESCRIPTION: SEQ ID NO:9:

ACATTTGAAC TCGCTGGAGC GTGTAGAA     28

(2) INFORMATION FOR SEQ ID NO:10:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: other nucleic acid, synthetic DNA, primer (iv) ANTI-SENSE: NO (xi) SEQUENCE DESCRIPTION: SEQ ID NO:10:

ACATTTGAAC TCGATCGAGC GTGTAGAA     28

(2) INFORMATION FOR SEQ ID NO:11:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: other nucleic acid, synthetic DNA, primer (iv) ANTI-SENSE: NO (xi) SEQUENCE DESCRIPTION: SEQ ID NO:11:

ACATTTGAAC TCGACGGAGC GTGTAGAA     28

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA, primer ( i v ) ANTI-SENSE: NO ( x i ) SEQUENCE DESCRIPTION: SEQ ID NO:12:

GATGTGCACA ATTGTGTTGC CTTAGGTGCC     30

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA, primer ( i v ) ANTI-SENSE: NO ( x i ) SEQUENCE DESCRIPTION: SEQ ID NO:13:

CACAATTTTT GCGCCTTAGG     20

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA, primer ( i v ) ANTI-SENSE: NO ( x i ) SEQUENCE DESCRIPTION: SEQ ID NO:14:

AATTTTGTTG CCTGTGGTGC CCCATTG     27

( 2 ) INFORMATION FOR SEQ ID NO:15:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA, primer ( i v ) ANTI-SENSE: NO ( x i ) SEQUENCE DESCRIPTION: SEQ ID NO:15:

GTTGCCTTAG GTTGCCCATT GGCTCCT     27

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA, primer (i v) ANTI-SENSE: NO (x i) SEQUENCE DESCRIPTION: SEQ ID NO:16:

TTAGGTGCCC CATGTGCTCC TCGTGAT 27

(2) INFORMATION FOR SEQ ID NO:17:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: other nucleic acid, synthetic DNA, primer (i v) ANTI-SENSE: NO (x i) SEQUENCE DESCRIPTION: SEQ ID NO:17:

GCCCCATTGG CTTGTCGTGA TGCTGGT 27

(2) INFORMATION FOR SEQ ID NO:18:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: other nucleic acid, synthetic DNA, primer (i v) ANTI-SENSE: NO (x i) SEQUENCE DESCRIPTION: SEQ ID NO:18:

CCATTGGCTC CTTGTGATGC TGGTTCC 27

(2) INFORMATION FOR SEQ ID NO:19:

(i) SEQUENCE CHARACTERISTICS:
(A) LENGTH: 234 base pairs
(B) TYPE: nucleic acid
(C) STRANDEDNESS: double
(D) TOPOLOGY: linear (i i) MOLECULE TYPE: other nucleic acid, synthetic DNA (i x) FEATURE:
(A) NAME/KEY: CDS
(B) LOCATION: 1..234
(C) IDENTIFICATION METHOD: E (x i) SEQUENCE DESCRIPTION: SEQ ID NO:19:

| TTA | ATG | CAT | AAC | CTT | GGC | AAA | CAT | TTG | AAC | TCC | ATG | GAG | CGT | GTA | GAA | 48 |
| Leu | Met | His | Asn | Leu | Gly | Lys | His | Leu | Asn | Ser | Met | Glu | Arg | Val | Glu | |
| 1 | | | | 5 | | | | | 10 | | | | | 15 | | |

| TGG | CTG | CGT | AAG | AAG | TTG | CAG | GAT | GTG | CAC | AAT | TTT | GTT | GCC | TTA | GGT | 96 |
| Trp | Leu | Arg | Lys | Lys | Leu | Gln | Asp | Val | His | Asn | Phe | Val | Ala | Leu | Gly | |
| | | | 20 | | | | | 25 | | | | | 30 | | | |

| GCC | CCA | TTG | GCT | CCT | CGT | GAT | GCT | GGT | TCC | CAA | AGA | CCA | CGT | AAA | AAG | 144 |
| Ala | Pro | Leu | Ala | Pro | Arg | Asp | Ala | Gly | Ser | Gln | Arg | Pro | Arg | Lys | Lys | |
| | | 35 | | | | 40 | | | | | 45 | | | | | |

| GAA | GAC | AAT | GTC | TTA | GTT | GAG | AGC | CAT | GAA | AAA | TCC | CTA | GGC | GAG | GCA | 192 |
| Glu | Asp | Asn | Val | Leu | Val | Glu | Ser | His | Glu | Lys | Ser | Leu | Gly | Glu | Ala | |
| | 50 | | | | | 55 | | | | | 60 | | | | | |

| GAC | AAG | GCC | GAT | GTG | AAT | GTA | TTA | ACT | AAA | GCT | AAA | TCC | CAG | | | 234 |
| Asp | Lys | Ala | Asp | Val | Asn | Val | Leu | Thr | Lys | Ala | Lys | Ser | Gln | | | |
| 65 | | | | | 70 | | | | | 75 | | | | | | |

(2) INFORMATION FOR SEQ ID NO:20:

(i) SEQUENCE CHARACTERISTICS:
  (A) LENGTH: 237 base pairs
  (B) TYPE: nucleic acid
  (C) STRANDEDNESS: double
  (D) TOPOLOGY: linear (ii) MOLECULE TYPE: other nucleic acid, synthetic DNA (ix) FEATURE:
  (A) NAME/KEY: CDS
  (B) LOCATION: 1..237
  (C) IDENTIFICATION METHOD: E (xi) SEQUENCE DESCRIPTION: SEQ ID NO:20:

```
CAG TTA ATG CAT AAC CTT GGC AAA CAT TTG AAC TCC ATG GAG CGT GTA    48
Gln Leu Met His Asn Leu Gly Lys His Leu Asn Ser Met Glu Arg Val
 1               5                  10                  15

GAA TGG CTG CGT AAG AAG TTG CAG GAT GTG CAC AAT TTT GTT GCC TTA    96
Glu Trp Leu Arg Lys Lys Leu Gln Asp Val His Asn Phe Val Ala Leu
            20                  25                  30

GGT GCC CCA TTG GCT CCT CGT GAT GCT GGT TCC CAA AGA CCA CGT AAA   144
Gly Ala Pro Leu Ala Pro Arg Asp Ala Gly Ser Gln Arg Pro Arg Lys
        35                  40                  45

AAG GAA GAC AAT GTC TTA GTT GAG AGC CAT GAA AAA TCC CTA GGC GAG   192
Lys Glu Asp Asn Val Leu Val Glu Ser His Glu Lys Ser Leu Gly Glu
    50                  55                  60

GCA GAC AAG GCC GAT GTG AAT GTA TTA ACT AAA GCT AAA TCC CAG       237
Ala Asp Lys Ala Asp Val Asn Val Leu Thr Lys Ala Lys Ser Gln
65                  70                  75
```

(2) INFORMATION FOR SEQ ID NO:21:

(i) SEQUENCE CHARACTERISTICS:
    (A) LENGTH: 240 base pairs
    (B) TYPE: nucleic acid
    (C) STRANDEDNESS: double
    (D) TOPOLOGY: linear (ii) MOLECULE TYPE: other nucleic acid, synthetic DNA (ix) FEATURE:
    (A) NAME/KEY: CDS
    (B) LOCATION: 1..240
    (C) IDENTIFICATION METHOD: E (xi) SEQUENCE DESCRIPTION: SEQ ID NO:21:

```
ATT CAG TTA ATG CAT AAC CTT GGC AAA CAT TTG AAC TCC ATG GAG CGT    48
Ile Gln Leu Met His Asn Leu Gly Lys His Leu Asn Ser Met Glu Arg
 1               5                  10                  15

GTA GAA TGG CTG CGT AAG AAG TTG CAG GAT GTG CAC AAT TTT GTT GCC    96
Val Glu Trp Leu Arg Lys Lys Leu Gln Asp Val His Asn Phe Val Ala
            20                  25                  30

TTA GGT GCC CCA TTG GCT CCT CGT GAT GCT GGT TCC CAA AGA CCA CGT   144
Leu Gly Ala Pro Leu Ala Pro Arg Asp Ala Gly Ser Gln Arg Pro Arg
        35                  40                  45

AAA AAG GAA GAC AAT GTC TTA GTT GAG AGC CAT GAA AAA TCC CTA GGC   192
Lys Lys Glu Asp Asn Val Leu Val Glu Ser His Glu Lys Ser Leu Gly
    50                  55                  60

GAG GCA GAC AAG GCC GAT GTG AAT GTA TTA ACT AAA GCT AAA TCC CAG   240
Glu Ala Asp Lys Ala Asp Val Asn Val Leu Thr Lys Ala Lys Ser Gln
65                  70                  75                  80
```

(2) INFORMATION FOR SEQ ID NO:22:

(i) SEQUENCE CHARACTERISTICS:
    (A) LENGTH: 243 base pairs
    (B) TYPE: nucleic acid ( C ) STRANDEDNESS: double
( D ) TOPOLOGY: linear ( i i ) MOLECULE TYPE: other nucleic acid, synthetic DNA ( i x ) FEATURE:
( A ) NAME/KEY: CDS
( B ) LOCATION: 1..243
( C ) IDENTIFICATION METHOD: E ( x i ) SEQUENCE DESCRIPTION: SEQ ID NO:22:

| GAG | ATT | CAG | TTA | ATG | CAT | AAC | CTT | GGC | AAA | CAT | TTG | AAC | TCC | ATG | GAG | 48 |
|---|---|---|---|---|---|---|---|---|---|---|---|---|---|---|---|---|
| Glu | Ile | Gln | Leu | Met | His | Asn | Leu | Gly | Lys | His | Leu | Asn | Ser | Met | Glu | |
| 1 | | | | 5 | | | | | 10 | | | | | 15 | | |

| CGT | GTA | GAA | TGG | CTG | CGT | AAG | AAG | TTG | CAG | GAT | GTG | CAC | AAT | TTT | GTT | 96 |
|---|---|---|---|---|---|---|---|---|---|---|---|---|---|---|---|---|
| Arg | Val | Glu | Trp | Leu | Arg | Lys | Lys | Leu | Gln | Asp | Val | His | Asn | Phe | Val | |
| | | | 20 | | | | | 25 | | | | | 30 | | | |

| GCC | TTA | GGT | GCC | CCA | TTG | GCT | CCT | CGT | GAT | GCT | GGT | TCC | CAA | AGA | CCA | 144 |
|---|---|---|---|---|---|---|---|---|---|---|---|---|---|---|---|---|
| Ala | Leu | Gly | Ala | Pro | Leu | Ala | Pro | Arg | Asp | Ala | Gly | Ser | Gln | Arg | Pro | |
| | | 35 | | | | | 40 | | | | | 45 | | | | |

| CGT | AAA | AAG | GAA | GAC | AAT | GTC | TTA | GTT | GAG | AGC | CAT | GAA | AAA | TCC | CTA | 192 |
|---|---|---|---|---|---|---|---|---|---|---|---|---|---|---|---|---|
| Arg | Lys | Lys | Glu | Asp | Asn | Val | Leu | Val | Glu | Ser | His | Glu | Lys | Ser | Leu | |
| | 50 | | | | | 55 | | | | | 60 | | | | | |

| GGC | GAG | GCA | GAC | AAG | GCC | GAT | GTG | AAT | GTA | TTA | ACT | AAA | GCT | AAA | TCC | 240 |
|---|---|---|---|---|---|---|---|---|---|---|---|---|---|---|---|---|
| Gly | Glu | Ala | Asp | Lys | Ala | Asp | Val | Asn | Val | Leu | Thr | Lys | Ala | Lys | Ser | |
| 65 | | | | 70 | | | | | 75 | | | | | 80 | | |

| CAG | | | | | | | | | | | | | | | | 243 |
|---|---|---|---|---|---|---|---|---|---|---|---|---|---|---|---|---|
| Gln | | | | | | | | | | | | | | | | |

( 2 ) INFORMATION FOR SEQ ID NO:23:

( i ) SEQUENCE CHARACTERISTICS:
( A ) LENGTH: 252 base pairs
( B ) TYPE: nucleic acid
( C ) STRANDEDNESS: double
( D ) TOPOLOGY: linear ( i i ) MOLECULE TYPE: other nucleic acid, synthetic DNA ( i x ) FEATURE:
( A ) NAME/KEY: CDS
( B ) LOCATION: 1..252
( C ) IDENTIFICATION METHOD: E ( x i ) SEQUENCE DESCRIPTION: SEQ ID NO:23:

| TCT | GTG | TCC | GAG | ATT | CAG | TTA | ATG | CAT | AAC | CTT | GGC | AAA | CAT | TTG | AAC | 48 |
|---|---|---|---|---|---|---|---|---|---|---|---|---|---|---|---|---|
| Ser | Val | Ser | Glu | Ile | Gln | Leu | Met | His | Asn | Leu | Gly | Lys | His | Leu | Asn | |
| 1 | | | | 5 | | | | | 10 | | | | | 15 | | |

| TCC | ATG | GAG | CGT | GTA | GAA | TGG | CTG | CGT | AAG | AAG | TTG | CAG | GAT | GTG | CAC | 96 |
|---|---|---|---|---|---|---|---|---|---|---|---|---|---|---|---|---|
| Ser | Met | Glu | Arg | Val | Glu | Trp | Leu | Arg | Lys | Lys | Leu | Gln | Asp | Val | His | |
| | | | 20 | | | | | 25 | | | | | 30 | | | |

| AAT | TTT | GTT | GCC | TTA | GGT | GCC | CCA | TTG | GCT | CCT | CGT | GAT | GCT | GGT | TCC | 144 |
|---|---|---|---|---|---|---|---|---|---|---|---|---|---|---|---|---|
| Asn | Phe | Val | Ala | Leu | Gly | Ala | Pro | Leu | Ala | Pro | Arg | Asp | Ala | Gly | Ser | |
| | | 35 | | | | | 40 | | | | | 45 | | | | |

| CAA | AGA | CCA | CGT | AAA | AAG | GAA | GAC | AAT | GTC | TTA | GTT | GAG | AGC | CAT | GAA | 192 |
|---|---|---|---|---|---|---|---|---|---|---|---|---|---|---|---|---|
| Gln | Arg | Pro | Arg | Lys | Lys | Glu | Asp | Asn | Val | Leu | Val | Glu | Ser | His | Glu | |
| | 50 | | | | | 55 | | | | | 60 | | | | | |

| AAA | TCC | CTA | GGC | GAG | GCA | GAC | AAG | GCC | GAT | GTG | AAT | GTA | TTA | ACT | AAA | 240 |
|---|---|---|---|---|---|---|---|---|---|---|---|---|---|---|---|---|
| Lys | Ser | Leu | Gly | Glu | Ala | Asp | Lys | Ala | Asp | Val | Asn | Val | Leu | Thr | Lys | |
| 65 | | | | 70 | | | | | 75 | | | | | 80 | | |

| GCT | AAA | TCC | CAG | | | | | | | | | | | | | 252 |
|---|---|---|---|---|---|---|---|---|---|---|---|---|---|---|---|---|
| Ala | Lys | Ser | Gln | | | | | | | | | | | | | |

( 2 ) INFORMATION FOR SEQ ID NO:24:

( i ) SEQUENCE CHARACTERISTICS:

( A ) LENGTH: 245 base pairs
( B ) TYPE: nucleic acid
( C ) STRANDEDNESS: double
( D ) TOPOLOGY: linear ( i i ) MOLECULE TYPE: other nucleic acid, synthetic DNA ( i v ) ANTI-SENSE: NO ( x i ) SEQUENCE DESCRIPTION: SEQ ID NO:24:

| | | | | | | |
|---|---|---|---|---|---|---|
| TATGTTAATG | CATAACCTTG | GCAAACATTT | GAACTCCATG | GAGCGTGTAG | AATGGCTGCG | 60 |
| TAAGAAGTTG | CAGGATGTGC | ACAATTTTGT | TGCCTTAGGT | GCCCCATTGG | CTCCTCGTGA | 120 |
| TGCTGGTTCC | CAAAGACCAC | GTAAAAGGA | AGACAATGTC | TTAGTTGAGA | GCCATGAAAA | 180 |
| ATCCCTAGGC | GAGGCAGACA | AGGCCGATGT | GAATGTATTA | ACTAAAGCTA | AATCCCAGTA | 240 |
| ATGAG | | | | | | 245 |

( 2 ) INFORMATION FOR SEQ ID NO:25:

( i ) SEQUENCE CHARACTERISTICS:
( A ) LENGTH: 247 base pairs
( B ) TYPE: nucleic acid
( C ) STRANDEDNESS: double
( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:25:

| | | | | | | |
|---|---|---|---|---|---|---|
| GATCCTCATT | ACTGGGATTT | AGCTTTAGTT | AATACATTCA | CATCGGCCTT | GTCTGCCTCG | 60 |
| CCTAGGGATT | TTTCATGGCT | CTCAACTAAG | ACATTGTCTT | CCTTTTTACG | TGGTCTTTGG | 120 |
| GAACCAGCAT | CACGAGGAGC | CAATGGGGCA | CCTAAGGCAA | CAAAATTGTG | CACATCCTGC | 180 |
| AACTTCTTAC | GCAGCCATTC | TACACGCTCC | ATGGAGTTCA | AATGTTTGCC | AAGGTTATGC | 240 |
| ATTAACA | | | | | | 247 |

( 2 ) INFORMATION FOR SEQ ID NO:26:

( i ) SEQUENCE CHARACTERISTICS:
( A ) LENGTH: 248 base pairs
( B ) TYPE: nucleic acid
( C ) STRANDEDNESS: double
( D ) TOPOLOGY: linear ( i i ) MOLECULE TYPE: other nucleic acid, synthetic DNA ( i v ) ANTI-SENSE: NO ( x i ) SEQUENCE DESCRIPTION: SEQ ID NO:26:

| | | | | | | |
|---|---|---|---|---|---|---|
| TATGCAGTTA | ATGCATAACC | TTGGCAAACA | TTTGAACTCC | ATGGAGCGTG | TAGAATGGCT | 60 |
| GCGTAAGAAG | TTGCAGGATG | TGCACAATTT | TGTTGCCTTA | GGTGCCCCAT | TGGCTCCTCG | 120 |
| TGATGCTGGT | TCCCAAAGAC | CACGTAAAAA | GGAAGACAAT | GTCTTAGTTG | AGAGCCATGA | 180 |
| AAAATCCCTA | GGCGAGGCAG | ACAAGGCCGA | TGTGAATGTA | TTAACTAAAG | CTAAATCCCA | 240 |
| GTAATGAG | | | | | | 248 |

( 2 ) INFORMATION FOR SEQ ID NO:27:

( i ) SEQUENCE CHARACTERISTICS:
( A ) LENGTH: 250 base pairs
( B ) TYPE: nucleic acid
( C ) STRANDEDNESS: double
( D ) TOPOLOGY: linear (i i) MOLECULE TYPE: other nucleic acid, synthetic DNA (i v) ANTI-SENSE: YES (x i) SEQUENCE DESCRIPTION: SEQ ID NO:27:

```
GATCCTCATT ACTGGGATTT AGCTTTAGTT AATACATTCA CATCGGCCTT GTCTGCCTCG      60
CCTAGGGATT TTTCATGGCT CTCAACTAAG ACATTGTCTT CCTTTTTACG TGGTCTTTGG     120
GAACCAGCAT CACGAGGAGC CAATGGGGCA CCTAAGGCAA CAAAATTGTG CACATCCTGC     180
AACTTCTTAC GCAGCCATTC TACACGCTCC ATGGAGTTCA AATGTTTGCC AAGGTTATGC     240
ATTAACTGCA                                                            250
```

(2) INFORMATION FOR SEQ ID NO:28:

(i) SEQUENCE CHARACTERISTICS:
        (A) LENGTH: 251 base pairs
        (B) TYPE: nucleic acid
        (C) STRANDEDNESS: double
        (D) TOPOLOGY: linear (i i) MOLECULE TYPE: other nucleic acid, synthetic DNA (i v) ANTI-SENSE: NO (x i) SEQUENCE DESCRIPTION: SEQ ID NO:28:

```
TATGATTCAG TTAATGCATA ACCTTGGCAA ACATTTGAAC TCCATGGAGC GTGTAGAATG      60
GCTGCGTAAG AAGTTGCAGG ATGTGCACAA TTTTGTTGCC TTAGGTGCCC CATTGGCTCC     120
TCGTGATGCT GGTTCCCAAA GACCACGTAA AAAGGAAGAC AATGTCTTAG TTGAGAGCCA     180
TGAAAAATCC CTAGGCGAGG CAGACAAGGC CGATGTGAAT GTATTAACTA AAGCTAAATC     240
CCAGTAATGA G                                                          251
```

(2) INFORMATION FOR SEQ ID NO:29:

(i) SEQUENCE CHARACTERISTICS:
        (A) LENGTH: 253 base pairs
        (B) TYPE: nucleic acid
        (C) STRANDEDNESS: double
        (D) TOPOLOGY: linear (i i) MOLECULE TYPE: other nucleic acid, synthetic DNA (i v) ANTI-SENSE: YES (x i) SEQUENCE DESCRIPTION: SEQ ID NO:29:

```
GATCCTCATT ACTGGGATTT AGCTTTAGTT AATACATTCA CATCGGCCTT GTCTGCCTCG      60
CCTAGGGATT TTTCATGGCT CTCAACTAAG ACATTGTCTT CCTTTTTACG TGGTCTTTGG     120
GAACCAGCAT CACGAGGAGC CAATGGGGCA CCTAAGGCAA CAAAATTGTG CACATCCTGC     180
AACTTCTTAC GCAGCCATTC TACACGCTCC ATGGAGTTCA AATGTTTGCC AAGGTTATGC     240
ATTAACTGAA TCA                                                        253
```

(2) INFORMATION FOR SEQ ID NO:30:

(i) SEQUENCE CHARACTERISTICS:
        (A) LENGTH: 254 base pairs
        (B) TYPE: nucleic acid
        (C) STRANDEDNESS: double
        (D) TOPOLOGY: linear (i i) MOLECULE TYPE: other nucleic acid, synthetic DNA (i v) ANTI-SENSE: NO (x i) SEQUENCE DESCRIPTION: SEQ ID NO:30:

```
TATGGAGATT  CAGTTAATGC  ATAACCTTGG  CAAACATTTG  AACTCCATGG  AGCGTGTAGA    60

ATGGCTGCGT  AAGAAGTTGC  AGGATGTGCA  CAATTTTGTT  GCCTTAGGTG  CCCCATTGGC   120

TCCTCGTGAT  GCTGGTTCCC  AAAGACCACG  TAAAAAGGAA  GACAATGTCT  TAGTTGAGAG   180

CCATGAAAAA  TCCCTAGGCG  AGGCAGACAA  GGCCGATGTG  AATGTATTAA  CTAAAGCTAA   240

ATCCCAGTAA  TGAG                                                        254
```

( 2 ) INFORMATION FOR SEQ ID NO:31:

( i ) SEQUENCE CHARACTERISTICS:
        ( A ) LENGTH: 256 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:31:

```
GATCCTCATT  ACTGGGATTT  AGCTTTAGTT  AATACATTCA  CATCGGCCTT  GTCTGCCTCG    60

CCTAGGGATT  TTTCATGGCT  CTCAACTAAG  ACATTGTCTT  CCTTTTTACG  TGGTCTTTGG   120

GAACCAGCAT  CACGAGGAGC  CAATGGGGCA  CCTAAGGCAA  CAAAATTGTG  CACATCCTGC   180

AACTTCTTAC  GCAGCCATTC  TACACGCTCC  ATGGAGTTCA  AATGTTTGCC  AAGGTTATGC   240

ATTAACTGAA  TCTCCA                                                      256
```

( 2 ) INFORMATION FOR SEQ ID NO:32:

( i ) SEQUENCE CHARACTERISTICS:
        ( A ) LENGTH: 263 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( i v ) ANTI-SENSE: NO ( x i ) SEQUENCE DESCRIPTION: SEQ ID NO:32:

```
TATGTCTGTG  TCCGAGATTC  AGTTAATGCA  TAACCTTGGC  AAACATTTGA  ACTCCATGGA    60

GCGTGTAGAA  TGGCTGCGTA  AGAAGTTGCA  GGATGTGCAC  AATTTTGTTG  CCTTAGGTGC   120

CCCATTGGCT  CCTCGTGATG  CTGGTTCCCA  AAGACCACGT  AAAAGGAAG   ACAATGTCTT   180

AGTTGAGAGC  CATGAAAAAT  CCCTAGGCGA  GGCAGACAAG  GCCGATGTGA  ATGTATTAAC   240

TAAAGCTAAA  TCCCAGTAAT  GAG                                             263
```

( 2 ) INFORMATION FOR SEQ ID NO:33:

( i ) SEQUENCE CHARACTERISTICS:
        ( A ) LENGTH: 265 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:33:

```
GATCCTCATT  ACTGGGATTT  AGCTTTAGTT  AATACATTCA  CATCGGCCTT  GTCTGCCTCG    60

CCTAGGGATT  TTTCATGGCT  CTCAACTAAG  ACATTGTCTT  CCTTTTTACG  TGGTCTTTGG   120
```

| GAACCAGCAT | CACGAGGAGC | CAATGGGGCA | CCTAAGGCAA | CAAAATTGTG | CACATCCTGC | 180 |
| AACTTCTTAC | GCAGCCATTC | TACACGCTCC | ATGGAGTTCA | AATGTTTGCC | AAGGTTATGC | 240 |
| ATTAACTGAA | TCTCGGACAC | AGACA | | | | 265 |

( 2 ) INFORMATION FOR SEQ ID NO:34:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:34:

TATGTTAATG CA        12

( 2 ) INFORMATION FOR SEQ ID NO:35:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:35:

AGGTTATGCA TTCA        14

( 2 ) INFORMATION FOR SEQ ID NO:36:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:36:

TATGCAGTTA ATGCA        15

( 2 ) INFORMATION FOR SEQ ID NO:37:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:37:

AGGTTATGCA TTCTGCA        17

( 2 ) INFORMATION FOR SEQ ID NO:38:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:38:

TATGATTCAG TTAATGCA                                                                                            18

( 2 ) INFORMATION FOR SEQ ID NO:39:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:39:

AGGTTATGCA TTCTGAATCA                                                                                          20

( 2 ) INFORMATION FOR SEQ ID NO:40:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:40:

TATGGAGATT CAGTTAATGC A                                                                                        21

( 2 ) INFORMATION FOR SEQ ID NO:41:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:41:

AGGTTATGCA TTCTGAATCT CCA                                                                                      23

( 2 ) INFORMATION FOR SEQ ID NO:42:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:42:

TATGTCTGTG TCCGAGATTC AGTTAATGCA                                                                               30

( 2 ) INFORMATION FOR SEQ ID NO:43:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:43:

AGGTTATGCA TTAACTCAAT CTCGGACACA GACA    34

( 2 ) INFORMATION FOR SEQ ID NO:44:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:44:

TAACCTTGGC AAACATTTGA ACTCCATGGA GCGTGTAGAA TGGCT    45

( 2 ) INFORMATION FOR SEQ ID NO:45:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:45:

TTACGCAGCC ATTCTACACG CTCCATGGAG TTCAAATGTT TGCCA    45

( 2 ) INFORMATION FOR SEQ ID NO:46:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:46:

GCGTAAGAAG TTGCAGGATG TGCACAATTT    30

( 2 ) INFORMATION FOR SEQ ID NO:47:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:47:

GCAACAAAAT TGTGCACATC CTGCAACTTC    30

( 2 ) INFORMATION FOR SEQ ID NO:48:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:48:

TGTTGCCTTA GGTGCCCCAT TGGCTCCTCG TGATGCTGGT TCCCAA 46

(2) INFORMATION FOR SEQ ID NO:49:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid, synthetic DNA (iv) ANTI-SENSE: YES (xi) SEQUENCE DESCRIPTION: SEQ ID NO:49:

TGGTCTTTGG GAACCAGCAT CACGAGGAGC CAATGGGGCA CCTAAG 46

(2) INFORMATION FOR SEQ ID NO:50:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:50:

AGACCACGTA AAAAGGAAGA CAATGTCTTA GTTGAGAGCC A 41

(2) INFORMATION FOR SEQ ID NO:51:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid, synthetic DNA (iv) ANTI-SENSE: YES (xi) SEQUENCE DESCRIPTION: SEQ ID NO:51:

TTTTCATGGC TCTCAACTAA GACATTGTCT TCCTTTTTAC G 41

(2) INFORMATION FOR SEQ ID NO:52:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:52:

TGAAAAATCC CTAGGCGAGG CAGACAAGGC CGATGTGAAT GT 42

(2) INFORMATION FOR SEQ ID NO:53:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid, synthetic DNA (iv) ANTI-SENSE: YES ( x i ) SEQUENCE DESCRIPTION: SEQ ID NO:53:

GTTAATACAT TCACATCGGC CTTGTCTGCC TCGCCTAGGC AT 42

( 2 ) INFORMATION FOR SEQ ID NO:54:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( x i ) SEQUENCE DESCRIPTION: SEQ ID NO:54:

ATTAACTAAA GCTAAATCCC AGTAATGAG 29

( 2 ) INFORMATION FOR SEQ ID NO:55:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:55:

GATCCTCATT ACTGGGATTT AGCTTTA 27

( 2 ) INFORMATION FOR SEQ ID NO:56:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( i x ) FEATURE:
        ( A ) NAME/KEY: CDS
        ( B ) LOCATION: 1..252
        ( A ) NAME/KEY: mutation
        ( B ) LOCATION: 103...105
        ( C ) IDENTIFICATION METHOD: E ( x i ) SEQUENCE DESCRIPTION: SEQ ID NO:56:

| TCT | GTG | TCC | GAG | ATT | CAG | TTA | ATG | CAT | AAC | CTT | GGC | AAA | CAT | TTG | AAC | 48 |
| Ser | Val | Ser | Glu | Ile | Gln | Leu | Met | His | Asn | Leu | Gly | Lys | His | Leu | Asn | |
| 1 | | | | 5 | | | | | 10 | | | | | 15 | | |

| TCC | ATG | GAG | CGT | GTA | GAA | TGG | CTG | CGT | AAG | AAG | TTG | CAG | GAT | GTG | CAC | 96 |
| Ser | Met | Glu | Arg | Val | Glu | Trp | Leu | Arg | Lys | Lys | Leu | Gln | Asp | Val | His | |
| | | | 20 | | | | | 25 | | | | | 30 | | | |

| AAT | TTT | TGC | GCC | TTA | GGT | GCC | CCA | TTG | GCT | CCT | CGT | GAT | GCT | GGT | TCC | 144 |
| Asn | Phe | Cys | Ala | Leu | Gly | Ala | Pro | Leu | Ala | Pro | Arg | Asp | Ala | Gly | Ser | |
| | | 35 | | | | | 40 | | | | | 45 | | | | |

| CAA | AGA | CCA | CGT | AAA | AAG | GAA | GAC | AAT | GTC | TTA | GTT | GAG | AGC | CAT | GAA | 192 |
| Gln | Arg | Pro | Arg | Lys | Lys | Glu | Asp | Asn | Val | Leu | Val | Glu | Ser | His | Glu | |
| | 50 | | | | | 55 | | | | | 60 | | | | | |

| AAA | TCC | CTA | GGC | GAG | GCA | GAC | AAG | GCC | GAT | GTG | AAT | GTA | TTA | ACT | AAA | 240 |
| Lys | Ser | Leu | Gly | Glu | Ala | Asp | Lys | Ala | Asp | Val | Asn | Val | Leu | Thr | Lys | |
| 65 | | | | | 70 | | | | | 75 | | | | | 80 | |

| GCT | AAA | TCC | CAG | | | | | | | | | | | | | 252 |
| Ala | Lys | Ser | Gln | | | | | | | | | | | | | |

( 2 ) INFORMATION FOR SEQ ID NO:57:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( i x ) FEATURE:
        ( A ) NAME/KEY: CDS
        ( B ) LOCATION: 1..252
        ( A ) NAME/KEY: mutation
        ( B ) LOCATION: 51...52
        ( C ) IDENTIFICATION METHOD: E ( x i ) SEQUENCE DESCRIPTION: SEQ ID NO:57:

```
TCT GTG TCC GAG ATT CAG TTA ATG CAT AAC CTT GGC AAA CAT TTG AAC       48
Ser Val Ser Glu Ile Gln Leu Met His Asn Leu Gly Lys His Leu Asn
 1               5                  10                  15

TCG CTG GAG CGT GTA GAA TGG CTG CGT AAG AAG TTG CAG GAT GTG CAC       96
Ser Leu Glu Arg Val Glu Trp Leu Arg Lys Lys Leu Gln Asp Val His
                20                  25                  30

AAT TTT GTT GCC TTA GGT GCC CCA TTG GCT CCT CGT GAT GCT GGT TCC      144
Asn Phe Val Ala Leu Gly Ala Pro Leu Ala Pro Arg Asp Ala Gly Ser
         35                  40                  45

CAA AGA CCA CGT AAA AAG GAA GAC AAT GTC TTA GTT GAG AGC CAT GAA      192
Gln Arg Pro Arg Lys Lys Glu Asp Asn Val Leu Val Glu Ser His Glu
     50                  55                  60

AAA TCC CTA GGC GAG GCA GAC AAG GCC GAT GTG AAT GTA TTA ACT AAA      240
Lys Ser Leu Gly Glu Ala Asp Lys Ala Asp Val Asn Val Leu Thr Lys
 65                  70                  75                  80

GCT AAA TCC CAG                                                      252
Ala Lys Ser Gln
```

( 2 ) INFORMATION FOR SEQ ID NO:58:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( i x ) FEATURE:
        ( A ) NAME/KEY: CDS
        ( B ) LOCATION: 1..252
        ( A ) NAME/KEY: mutation
        ( B ) LOCATION: 19...24
        ( C ) IDENTIFICATION METHOD: E ( x i ) SEQUENCE DESCRIPTION: SEQ ID NO:58:

```
TCT GTG TCC GAG ATT CAG CTG CTG CAT AAC CTT GGC AAA CAT TTG AAC       48
Ser Val Ser Glu Ile Gln Leu Leu His Asn Leu Gly Lys His Leu Asn
 1               5                  10                  15

TCC ATG GAG CGT GTA GAA TGG CTG CGT AAG AAG TTG CAG GAT GTG CAC       96
Ser Met Glu Arg Val Glu Trp Leu Arg Lys Lys Leu Gln Asp Val His
                20                  25                  30

AAT TTT GTT GCC TTA GGT GCC CCA TTG GCT CCT CGT GAT GCT GGT TCC      144
Asn Phe Val Ala Leu Gly Ala Pro Leu Ala Pro Arg Asp Ala Gly Ser
         35                  40                  45

CAA AGA CCA CGT AAA AAG GAA GAC AAT GTC TTA GTT GAG AGC CAT GAA      192
Gln Arg Pro Arg Lys Lys Glu Asp Asn Val Leu Val Glu Ser His Glu
     50                  55                  60
```

| AAA | TCC | CTA | GGC | GAG | GCA | GAC | AAG | GCC | GAT | GTG | AAT | GTA | TTA | ACT | AAA | 240 |
| Lys | Ser | Leu | Gly | Glu | Ala | Asp | Lys | Ala | Asp | Val | Asn | Val | Leu | Thr | Lys | |
| 65 | | | | 70 | | | | | 75 | | | | | | 80 | |

| GCT | AAA | TCC | CAG | 252 |
| Ala | Lys | Ser | Gln | |

( 2 ) INFORMATION FOR SEQ ID NO:59:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i v ) ANTI-SENSE: NO ( x i ) SEQUENCE DESCRIPTION: SEQ ID NO:59:

TATGTTACTC CATAACCTTG GCAAACATTT GAACTC    36

( 2 ) INFORMATION FOR SEQ ID NO:60:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid, synthetic DNA ( i v ) ANTI-SENSE: YES ( x i ) SEQUENCE DESCRIPTION: SEQ ID NO:60:

CATGGAGTTC AAATGTTTGC CAAGGTTATG GAGTAACA    38

( 2 ) INFORMATION FOR SEQ ID NO:61:

( i ) SEQUENCE CHARACTERISTICS:
        ( A ) LENGTH: 234 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( i x ) FEATURE:
        ( A ) NAME/KEY: CDS
        ( B ) LOCATION: 1..234
        ( A ) NAME/KEY: mutation
        ( B ) LOCATION: 4,6
        ( C ) IDENTIFICATION METHOD: E ( x i ) SEQUENCE DESCRIPTION: SEQ ID NO:61:

| TTA | CTC | CAT | AAC | CTT | GGC | AAA | CAT | TTG | AAC | TCC | ATG | GAG | CGT | GTA | GAA | 48 |
| Leu | Leu | His | Asn | Leu | Gly | Lys | His | Leu | Asn | Ser | Met | Glu | Arg | Val | Glu | |
| 1 | | | | 5 | | | | | 10 | | | | | 15 | | |

| TGG | CTG | CGT | AAG | AAG | TTG | CAG | GAT | GTG | CAC | AAT | TTT | GTT | GCC | TTA | GGT | 96 |
| Trp | Leu | Arg | Lys | Lys | Leu | Gln | Asp | Val | His | Asn | Phe | Val | Ala | Leu | Gly | |
| | | | 20 | | | | | 25 | | | | | 30 | | | |

| GCC | CCA | TTG | GCT | CCT | CGT | GAT | GCT | GGT | TCC | CAA | AGA | CCA | CGT | AAA | AAG | 144 |
| Ala | Pro | Leu | Ala | Pro | Arg | Asp | Ala | Gly | Ser | Gln | Arg | Pro | Arg | Lys | Lys | |
| | | 35 | | | | | 40 | | | | | 45 | | | | |

| GAA | GAC | AAT | GTC | TTA | GTT | GAG | AGC | CAT | GAA | AAA | TCC | CTA | GGC | GAG | GCA | 192 |
| Glu | Asp | Asn | Val | Leu | Val | Glu | Ser | His | Glu | Lys | Ser | Leu | Gly | Glu | Ala | |
| | 50 | | | | | 55 | | | | | 60 | | | | | |

| GAC | AAG | GCC | GAT | GTG | AAT | GTA | TTA | ACT | AAA | GCT | AAA | TCC | CAG | 234 |
| Asp | Lys | Ala | Asp | Val | Asn | Val | Leu | Thr | Lys | Ala | Lys | Ser | Gln | |
| 65 | | | | 70 | | | | | 75 | | | | | |

( 2 ) INFORMATION FOR SEQ ID NO:62:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( i x ) FEATURE:
        ( A ) NAME/KEY: CDS
        ( B ) LOCATION: 1..252
        ( A ) NAME/KEY: mutation
        ( B ) LOCATION: 19,21,22,51,52
        ( C ) IDENTIFICATION METHOD: E ( x i ) SEQUENCE DESCRIPTION: SEQ ID NO:62:

```
TCT  GTG  TCC  GAG  ATT  CAG  CTG  CTG  CAT  AAC  CTT  GGC  AAA  CAT  TTG  AAC         48
Ser  Val  Ser  Glu  Ile  Gln  Leu  Leu  His  Asn  Leu  Gly  Lys  His  Leu  Asn
 1                    5                   10                        15

TCG  CTG  GAG  CGT  GTA  GAA  TGG  CTG  CGT  AAG  AAG  TTG  CAG  GAT  GTG  CAC         96
Ser  Leu  Glu  Arg  Val  Glu  Trp  Leu  Arg  Lys  Lys  Leu  Gln  Asp  Val  His
               20                        25                   30

AAT  TTT  GTT  GCC  TTA  GGT  GCC  CCA  TTG  GCT  CCT  CGT  GAT  GCT  GGT  TCC        144
Asn  Phe  Val  Ala  Leu  Gly  Ala  Pro  Leu  Ala  Pro  Arg  Asp  Ala  Gly  Ser
          35                        40                        45

CAA  AGA  CCA  CGT  AAA  AAG  GAA  GAC  AAT  GTC  TTA  GTT  GAG  AGC  CAT  GAA        192
Gln  Arg  Pro  Arg  Lys  Lys  Glu  Asp  Asn  Val  Leu  Val  Glu  Ser  His  Glu
     50                             55                   60

AAA  TCC  CTA  GGC  GAG  GCA  GAC  AAG  GCC  GAT  GTG  AAT  GTA  TTA  ACT  AAA        240
Lys  Ser  Leu  Gly  Glu  Ala  Asp  Lys  Ala  Asp  Val  Asn  Val  Leu  Thr  Lys
 65                        70                   75                        80

GCT  AAA  TCC  CAG                                                                    252
Ala  Lys  Ser  Gln
```